US009902782B2

(12) United States Patent
Kamohara et al.

(10) Patent No.: US 9,902,782 B2
(45) Date of Patent: Feb. 27, 2018

(54) ANTI-HUMAN TIE-2 ANTIBODY

(71) Applicant: Astellas Pharma Inc., Chuo-ku, Tokyo (JP)

(72) Inventors: Masazumi Kamohara, Tokyo (JP); Shigenori Yagi, Tokyo (JP); Yoshinori Ishii, Tokyo (JP); Hiromi Nara, Tokyo (JP)

(73) Assignee: Astellas Pharma Inc., Tokyo (JP)

( * ) Notice: Subject to any disclaimer, the term of this patent is extended or adjusted under 35 U.S.C. 154(b) by 0 days.

(21) Appl. No.: 15/585,374

(22) Filed: May 3, 2017

(65) Prior Publication Data

US 2017/0253669 A1    Sep. 7, 2017

Related U.S. Application Data

(60) Division of application No. 15/134,803, filed on Apr. 21, 2016, now Pat. No. 9,683,051, which is a continuation of application No. PCT/JP2015/070089, filed on Jul. 14, 2015.

(30) Foreign Application Priority Data

Jul. 15, 2014    (JP) ................................ 2014-145135

(51) Int. Cl.
| | | |
|---|---|---|
| *C12N 5/07* | (2010.01) | |
| *C12N 5/10* | (2006.01) | |
| *C12N 15/09* | (2006.01) | |
| *C12N 15/63* | (2006.01) | |
| *C07K 16/18* | (2006.01) | |
| *C07K 16/28* | (2006.01) | |
| *A61K 39/395* | (2006.01) | |
| *C07K 16/40* | (2006.01) | |
| *A61K 39/00* | (2006.01) | |

(52) U.S. Cl.
CPC .......... *C07K 16/40* (2013.01); *A61K 39/3955* (2013.01); *C07K 16/2863* (2013.01); *C07K 16/2896* (2013.01); *C12N 15/63* (2013.01); *A61K 39/395* (2013.01); *A61K 2039/505* (2013.01); *C07K 16/28* (2013.01); *C07K 2317/24* (2013.01); *C07K 2317/33* (2013.01); *C07K 2317/34* (2013.01); *C07K 2317/35* (2013.01); *C07K 2317/40* (2013.01); *C07K 2317/51* (2013.01); *C07K 2317/515* (2013.01); *C07K 2317/52* (2013.01); *C07K 2317/55* (2013.01); *C07K 2317/565* (2013.01); *C07K 2317/64* (2013.01); *C07K 2317/76* (2013.01); *C07K 2317/92* (2013.01); *C07K 2319/00* (2013.01); *C12N 5/06* (2013.01); *C12N 15/09* (2013.01); *C12N 2510/02* (2013.01)

(58) Field of Classification Search
CPC .............. A61K 39/3955; A61K 39/395; A61K 38/177; A61K 39/39533; A61K 2300/00; A61K 2039/505; C07K 2317/76; C07K 2317/56; C07K 2317/565; C07K 2317/21; C07K 16/28; C07K 16/18; C07K 16/00; C07K 2317/75; C07K 16/2896; C07K 14/705

See application file for complete search history.

(56) References Cited

U.S. PATENT DOCUMENTS

| | | |
|---|---|---|
| 6,376,653 B1 | 4/2002 | Holmes |
| 2006/0057138 A1 | 3/2006 | Wood et al. |
| 2010/0233803 A1 | 9/2010 | Fandl et al. |
| 2013/0209492 A1 | 8/2013 | Thurston |

FOREIGN PATENT DOCUMENTS

| | | |
|---|---|---|
| EP | 2 281 845 A1 | 2/2011 |
| WO | WO 95/21866 A1 | 8/1995 |
| WO | WO 00/18437 A1 | 4/2000 |
| WO | WO 00/18804 A1 | 4/2000 |
| WO | WO-01/77342 A1 | 10/2001 |
| WO | WO-2012/047966 A2 | 4/2012 |
| WO | WO 2013/028442 A1 | 2/2013 |
| WO | WO 2014/020069 A1 | 2/2014 |

OTHER PUBLICATIONS

International Search Report dated Oct. 13, 2015, in PCT/JP2015/070089, with English translation.
Written Opinion dated Oct. 13, 2015, in PCT/JP2015/070089, with English translation.
Hwang et al., "Stimulation of angiogenesis and survival of endothelial cells by human monoclonal Tie2 receptor antibody," Biomaterials, 2015, 51:119-128.
Liu et al., "Heterogeneity of Monoclonal Antibodies," Journal of Pharmaceutical Sciences, Jul. 2008, 97(7):2426-2447.

(Continued)

*Primary Examiner* — Bridget E Bunner
(74) *Attorney, Agent, or Firm* — Foley & Lardner LLP

(57) ABSTRACT

Provided is an anti-human Tie2 antibody for preventing or treating diabetic macular edema, diabetic retinopathy, and critical limb ischemia by binding to a human Tie2 to activate the human Tie2. The present inventors have conducted investigations on an anti-human Tie2 antibody, and have thus provided an anti-human Tie2 antibody comprising four heavy chain variable regions and four light chain variable regions, in which the heavy chain variable region consists of the amino acid sequence of the amino acid numbers 1 to 122 of SEQ ID NO: 2, the light chain variable region consists of the amino acid sequence of the amino acid numbers 1 to 113 of SEQ ID NO: 4, the one heavy chain variable region and the one light chain variable region constitute one antigen-binding site, and the antibody comprises four antigen-binding sites.

8 Claims, 6 Drawing Sheets

(56) References Cited

OTHER PUBLICATIONS

Kumagai et al., "Chapter 1: High Functionalization of Antibody Domain by Mosaic Work and Development thereof to Medical Field," Frontier of Development of Antibody Medicine (Kotai Iyaku no Saizensen, $1^{st}$ print), Supervisor: Mitsuyoshi Ueda, CMC Publishing Co., Ltd. Jul. 20, 2007, 3-13, with English translation, 24 pages.

Office Action dated Oct. 3, 2017, in SG 11201700271R.

Moss, Andrew, "The angiopoietin: Tie 2 interaction: A potential target for future therapies in human vascular disease," Cytokine and Growth Factor Reviews, Jul. 6, 2013, vol. 24, No. 6, pp. 579-592.

Supplementary European Search Report dated Dec. 8, 2017, in EP 15822476.6.

SEQUENCE LISTING

<160> NUMBER OF SEQ ID NOS: 23

<210> SEQ ID NO 1
<211> LENGTH: 2037
<212> TYPE: DNA
<213> ORGANISM: Artificial Sequence
<220> FEATURE:
<223> OTHER INFORMATION: H-chain of anti-human Tie2 antibody
<220> FEATURE:
<221> NAME/KEY: CDS
<222> LOCATION: (1)..(2037)

<400> SEQUENCE: 1

```
gaa gtg cag ctg gtg gaa tct ggc ggc gga ctg gtg cag cct ggc gga      48
Glu Val Gln Leu Val Glu Ser Gly Gly Gly Leu Val Gln Pro Gly Gly
 1               5                  10                  15 tct ctg aga ctg tct tgt gcc gcc tcc ggc ttc acc ttc gac gac tac      96
Ser Leu Arg Leu Ser Cys Ala Ala Ser Gly Phe Thr Phe Asp Asp Tyr
             20                  25                  30 gct atg cac tgg gtg cga cag gcc cct ggc aag gga ctg gaa tgg gtg     144
Ala Met His Trp Val Arg Gln Ala Pro Gly Lys Gly Leu Glu Trp Val
         35                  40                  45 gcc ggc atc tcc tgg aac tcc ggc tct atc gtg tac gcc gac tcc gtg     192
Ala Gly Ile Ser Trp Asn Ser Gly Ser Ile Val Tyr Ala Asp Ser Val
     50                  55                  60 aag ggc cgg ttc acc atc tcc cgg gac aac tcc aag aac acc ctg tac     240
Lys Gly Arg Phe Thr Ile Ser Arg Asp Asn Ser Lys Asn Thr Leu Tyr
 65                  70                  75                  80 ctg cag atg aac tcc ctg cgg gcc gag gac acc gcc gtg tac tac tgc     288
Leu Gln Met Asn Ser Leu Arg Ala Glu Asp Thr Ala Val Tyr Tyr Cys
                 85                  90                  95 gct aag gac atc cgg gaa cag ctg gtg gaa gat gcc ttc gac atc tgg     336
Ala Lys Asp Ile Arg Glu Gln Leu Val Glu Asp Ala Phe Asp Ile Trp
            100                 105                 110 ggc cag ggc acc ctc gtg acc gtg tcc tct gct tct acc aag ggc ccc     384
Gly Gln Gly Thr Leu Val Thr Val Ser Ser Ala Ser Thr Lys Gly Pro
        115                 120                 125 tcc gtg ttc cct ctg gcc cct tcc agc aag tct acc tct ggc ggc aca     432
Ser Val Phe Pro Leu Ala Pro Ser Ser Lys Ser Thr Ser Gly Gly Thr
    130                 135                 140 gcc gct ctg ggc tgc ctc gtg aag gac tac ttc ccc gag ccc gtg aca     480
Ala Ala Leu Gly Cys Leu Val Lys Asp Tyr Phe Pro Glu Pro Val Thr
145                 150                 155                 160 gtg tct tgg aac tct ggc gcc ctg aca tct ggc gtg cac acc ttc cct     528
Val Ser Trp Asn Ser Gly Ala Leu Thr Ser Gly Val His Thr Phe Pro
                165                 170                 175 gct gtg ctg cag tcc tcc ggc ctg tac tcc ctg tcc tcc gtc gtg act     576
Ala Val Leu Gln Ser Ser Gly Leu Tyr Ser Leu Ser Ser Val Val Thr
            180                 185                 190 gtg ccc tcc agc tct ctg ggc acc cag acc tac atc tgc aac gtg aac     624
Val Pro Ser Ser Ser Leu Gly Thr Gln Thr Tyr Ile Cys Asn Val Asn
        195                 200                 205 cac aag ccc tcc aac acc aag gtg gac aag aag gtg gaa ccc aag tcc     672
His Lys Pro Ser Asn Thr Lys Val Asp Lys Lys Val Glu Pro Lys Ser
    210                 215                 220 tgc ggc agc gag gtg cag ctg gtg gaa agt ggg gga ggc ctg gtg cag     720
Cys Gly Ser Glu Val Gln Leu Val Glu Ser Gly Gly Gly Leu Val Gln
225                 230                 235                 240 cca ggt gga agc ctg aga ctg agc tgc gcc gct tct ggc ttt acc ttt     768
Pro Gly Gly Ser Leu Arg Leu Ser Cys Ala Ala Ser Gly Phe Thr Phe
                245                 250                 255
```

| | | |
|---|---|---|
| gat gat tat gcc atg cat tgg gtg cgc cag gct cca ggg aaa ggc ctg<br>Asp Asp Tyr Ala Met His Trp Val Arg Gln Ala Pro Gly Lys Gly Leu<br>260 265 270 | | 816 |
| gaa tgg gtg gca ggg atc agc tgg aac agc ggc agc atc gtg tat gct<br>Glu Trp Val Ala Gly Ile Ser Trp Asn Ser Gly Ser Ile Val Tyr Ala<br>275 280 285 | | 864 |
| gat agc gtg aag ggg cgc ttt aca atc agc aga gac aac agc aag aat<br>Asp Ser Val Lys Gly Arg Phe Thr Ile Ser Arg Asp Asn Ser Lys Asn<br>290 295 300 | | 912 |
| act ctg tac ctg cag atg aat agc ctg cgc gct gag gat aca gct gtg<br>Thr Leu Tyr Leu Gln Met Asn Ser Leu Arg Ala Glu Asp Thr Ala Val<br>305 310 315 320 | | 960 |
| tat tac tgt gcc aag gat att cgc gag cag ctg gtg gaa gat gct ttt<br>Tyr Tyr Cys Ala Lys Asp Ile Arg Glu Gln Leu Val Glu Asp Ala Phe<br>325 330 335 | | 1008 |
| gat att tgg ggg cag ggt aca ctc gtg aca gtg tct agc gcc tcc acc<br>Asp Ile Trp Gly Gln Gly Thr Leu Val Thr Val Ser Ser Ala Ser Thr<br>340 345 350 | | 1056 |
| aag ggc cca agc gtg ttc cca ctg gct ccc agc tcc aag agc acc tcc<br>Lys Gly Pro Ser Val Phe Pro Leu Ala Pro Ser Ser Lys Ser Thr Ser<br>355 360 365 | | 1104 |
| ggt gga act gct gcc ctg ggc tgt ctc gtg aaa gat tat ttt cct gag<br>Gly Gly Thr Ala Ala Leu Gly Cys Leu Val Lys Asp Tyr Phe Pro Glu<br>370 375 380 | | 1152 |
| cct gtg act gtg tcc tgg aat agc ggc gct ctg acc agc gga gtg cat<br>Pro Val Thr Val Ser Trp Asn Ser Gly Ala Leu Thr Ser Gly Val His<br>385 390 395 400 | | 1200 |
| acc ttt cca gcc gtg ctg cag agc agc ggc ctg tat agc ctg tcc agc<br>Thr Phe Pro Ala Val Leu Gln Ser Ser Gly Leu Tyr Ser Leu Ser Ser<br>405 410 415 | | 1248 |
| gtc gtg acc gtg cct tcc tct agc ctg gga aca cag aca tat atc tgt<br>Val Val Thr Val Pro Ser Ser Ser Leu Gly Thr Gln Thr Tyr Ile Cys<br>420 425 430 | | 1296 |
| aat gtg aat cat aag ccc agt aat acc aaa gtg gat aag aaa gtg gaa<br>Asn Val Asn His Lys Pro Ser Asn Thr Lys Val Asp Lys Lys Val Glu<br>435 440 445 | | 1344 |
| cct aag agc tgc gac aag acc cac acc tgt ccc cct tgt cct gcc cct<br>Pro Lys Ser Cys Asp Lys Thr His Thr Cys Pro Pro Cys Pro Ala Pro<br>450 455 460 | | 1392 |
| gaa gct gct ggc ggc cct tct gtg ttt ctg ttc ccc cca aag cct aag<br>Glu Ala Ala Gly Gly Pro Ser Val Phe Leu Phe Pro Pro Lys Pro Lys<br>465 470 475 480 | | 1440 |
| gac acc ctg atg atc tcc cgg acc ccc gaa gtg acc tgc gtg gtg gtg<br>Asp Thr Leu Met Ile Ser Arg Thr Pro Glu Val Thr Cys Val Val Val<br>485 490 495 | | 1488 |
| gat gtg tcc cac gag gac cct gaa gtg aag ttc aat tgg tac gtg gac<br>Asp Val Ser His Glu Asp Pro Glu Val Lys Phe Asn Trp Tyr Val Asp<br>500 505 510 | | 1536 |
| ggc gtg gaa gtg cac aac gcc aag acc aag cct aga gag gaa cag tac<br>Gly Val Glu Val His Asn Ala Lys Thr Lys Pro Arg Glu Glu Gln Tyr<br>515 520 525 | | 1584 |
| aac tcc acc tac cgg gtg gtg tcc gtg ctg aca gtg ctg cat cag gac<br>Asn Ser Thr Tyr Arg Val Val Ser Val Leu Thr Val Leu His Gln Asp<br>530 535 540 | | 1632 |
| tgg ctg aac ggc aaa gag tac aag tgc aag gtg tcc aac aag gcc ctg<br>Trp Leu Asn Gly Lys Glu Tyr Lys Cys Lys Val Ser Asn Lys Ala Leu<br>545 550 555 560 | | 1680 |
| ccc gcc tcc atc gaa aag acc atc tcc aag gcc aag ggc cag ccc cgg<br>Pro Ala Ser Ile Glu Lys Thr Ile Ser Lys Ala Lys Gly Gln Pro Arg<br>565 570 575 | | 1728 |

```
gaa ccc cag gtg tac aca ctg ccc cct agc agg gac gag ctg acc aag      1776
Glu Pro Gln Val Tyr Thr Leu Pro Pro Ser Arg Asp Glu Leu Thr Lys
            580                 585                 590 aac cag gtg tcc ctg acc tgt ctc gtg aag ggc ttc tac ccc tcc gat      1824
Asn Gln Val Ser Leu Thr Cys Leu Val Lys Gly Phe Tyr Pro Ser Asp
        595                 600                 605 atc gcc gtg gaa tgg gag tcc aac ggc cag cct gag aac aac tat aag      1872
Ile Ala Val Glu Trp Glu Ser Asn Gly Gln Pro Glu Asn Asn Tyr Lys
    610                 615                 620 acc acc ccc cct gtg ctg gac tcc gac ggc tca ttc ttt ctg tac tcc      1920
Thr Thr Pro Pro Val Leu Asp Ser Asp Gly Ser Phe Phe Leu Tyr Ser
625                 630                 635                 640 aag ctg acc gtg gac aag tcc cgg tgg cag cag ggc aac gtg ttc tcc      1968
Lys Leu Thr Val Asp Lys Ser Arg Trp Gln Gln Gly Asn Val Phe Ser
                645                 650                 655 tgc agc gtg atg cac gag gcc ctg cac aac cac tac acc cag aag tcc      2016
Cys Ser Val Met His Glu Ala Leu His Asn His Tyr Thr Gln Lys Ser
            660                 665                 670 ctg tcc ctg agc ccc ggc aaa                                          2037
Leu Ser Leu Ser Pro Gly Lys
        675

<210> SEQ ID NO 2
<211> LENGTH: 679
<212> TYPE: PRT
<213> ORGANISM: Artificial Sequence
<220> FEATURE:
<223> OTHER INFORMATION: Synthetic Construct

<400> SEQUENCE: 2

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ala Gly Ile Ser Trp Asn Ser Gly Ser Ile Val Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Ile Arg Glu Gln Leu Val Glu Asp Ala Phe Asp Ile Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Lys Val Glu Pro Lys Ser
```

-continued

```
            210                 215                 220
Cys Gly Ser Glu Val Gln Leu Val Glu Ser Gly Gly Leu Val Gln
225                 230                 235                 240

Pro Gly Gly Ser Leu Arg Leu Ser Cys Ala Ala Ser Gly Phe Thr Phe
                245                 250                 255

Asp Asp Tyr Ala Met His Trp Val Arg Gln Ala Pro Gly Lys Gly Leu
                260                 265                 270

Glu Trp Val Ala Gly Ile Ser Trp Asn Ser Gly Ser Ile Val Tyr Ala
            275                 280                 285

Asp Ser Val Lys Gly Arg Phe Thr Ile Ser Arg Asp Asn Ser Lys Asn
        290                 295                 300

Thr Leu Tyr Leu Gln Met Asn Ser Leu Arg Ala Glu Asp Thr Ala Val
305                 310                 315                 320

Tyr Tyr Cys Ala Lys Asp Ile Arg Glu Gln Leu Val Glu Asp Ala Phe
                325                 330                 335

Asp Ile Trp Gly Gln Gly Thr Leu Val Thr Val Ser Ser Ala Ser Thr
                340                 345                 350

Lys Gly Pro Ser Val Phe Pro Leu Ala Pro Ser Ser Lys Ser Thr Ser
            355                 360                 365

Gly Gly Thr Ala Ala Leu Gly Cys Leu Val Lys Asp Tyr Phe Pro Glu
        370                 375                 380

Pro Val Thr Val Ser Trp Asn Ser Gly Ala Leu Thr Ser Gly Val His
385                 390                 395                 400

Thr Phe Pro Ala Val Leu Gln Ser Ser Gly Leu Tyr Ser Leu Ser Ser
                405                 410                 415

Val Val Thr Val Pro Ser Ser Ser Leu Gly Thr Gln Thr Tyr Ile Cys
                420                 425                 430

Asn Val Asn His Lys Pro Ser Asn Thr Lys Val Asp Lys Lys Val Glu
            435                 440                 445

Pro Lys Ser Cys Asp Lys Thr His Thr Cys Pro Pro Cys Pro Ala Pro
        450                 455                 460

Glu Ala Ala Gly Gly Pro Ser Val Phe Leu Phe Pro Pro Lys Pro Lys
465                 470                 475                 480

Asp Thr Leu Met Ile Ser Arg Thr Pro Glu Val Thr Cys Val Val Val
                485                 490                 495

Asp Val Ser His Glu Asp Pro Glu Val Lys Phe Asn Trp Tyr Val Asp
                500                 505                 510

Gly Val Glu Val His Asn Ala Lys Thr Lys Pro Arg Glu Glu Gln Tyr
            515                 520                 525

Asn Ser Thr Tyr Arg Val Val Ser Val Leu Thr Val Leu His Gln Asp
        530                 535                 540

Trp Leu Asn Gly Lys Glu Tyr Lys Cys Lys Val Ser Asn Lys Ala Leu
545                 550                 555                 560

Pro Ala Ser Ile Glu Lys Thr Ile Ser Lys Ala Lys Gly Gln Pro Arg
                565                 570                 575

Glu Pro Gln Val Tyr Thr Leu Pro Pro Ser Arg Asp Glu Leu Thr Lys
                580                 585                 590

Asn Gln Val Ser Leu Thr Cys Leu Val Lys Gly Phe Tyr Pro Ser Asp
            595                 600                 605

Ile Ala Val Glu Trp Glu Ser Asn Gly Gln Pro Glu Asn Asn Tyr Lys
        610                 615                 620

Thr Thr Pro Pro Val Leu Asp Ser Asp Gly Ser Phe Phe Leu Tyr Ser
625                 630                 635                 640
```

```
Lys Leu Thr Val Asp Lys Ser Arg Trp Gln Gln Gly Asn Val Phe Ser
                645                 650                 655

Cys Ser Val Met His Glu Ala Leu His Asn His Tyr Thr Gln Lys Ser
            660                 665                 670

Leu Ser Leu Ser Pro Gly Lys
        675

<210> SEQ ID NO 3
<211> LENGTH: 657
<212> TYPE: DNA
<213> ORGANISM: Artificial Sequence
<220> FEATURE:
<223> OTHER INFORMATION: L-chain of anti-human Tie2 antibody
<220> FEATURE:
<221> NAME/KEY: CDS
<222> LOCATION: (1)..(657)

<400> SEQUENCE: 3
```

| | | | | | | | | | | | | | | | | |
|---|---|---|---|---|---|---|---|---|---|---|---|---|---|---|---|---|
| gac | ata | caa | atg | acc | cag | tct | cca | tcc | tca | ctt | agt | gcc | tct | gtt | ggc | 48 |
| Asp | Ile | Gln | Met | Thr | Gln | Ser | Pro | Ser | Ser | Leu | Ser | Ala | Ser | Val | Gly | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| gat | aga | gta | act | atc | aca | tgc | cgg | tcc | tcc | caa | tct | ctg | ctg | cat | tcc | 96 |
| Asp | Arg | Val | Thr | Ile | Thr | Cys | Arg | Ser | Ser | Gln | Ser | Leu | Leu | His | Ser | |
| | | 20 | | | | | 25 | | | | | 30 | | | | |

| | | | | | | | | | | | | | | | | |
|---|---|---|---|---|---|---|---|---|---|---|---|---|---|---|---|---|
| cac | cgc | tac | aac | tac | ctg | gac | tgg | tat | cag | cag | aaa | ccc | ggc | aaa | gct | 144 |
| His | Arg | Tyr | Asn | Tyr | Leu | Asp | Trp | Tyr | Gln | Gln | Lys | Pro | Gly | Lys | Ala | |
| | 35 | | | | | 40 | | | | | 45 | | | | | |

| | | | | | | | | | | | | | | | | |
|---|---|---|---|---|---|---|---|---|---|---|---|---|---|---|---|---|
| ccc | aag | ctc | ttg | att | tac | ctg | ggg | tct | aat | agg | gca | agc | ggt | gtc | cca | 192 |
| Pro | Lys | Leu | Leu | Ile | Tyr | Leu | Gly | Ser | Asn | Arg | Ala | Ser | Gly | Val | Pro | |
| 50 | | | | | 55 | | | | | 60 | | | | | | |

| | | | | | | | | | | | | | | | | |
|---|---|---|---|---|---|---|---|---|---|---|---|---|---|---|---|---|
| agt | cga | ttc | agc | gga | agc | ggg | agc | ggc | aca | gat | ttt | aca | ctc | act | atc | 240 |
| Ser | Arg | Phe | Ser | Gly | Ser | Gly | Ser | Gly | Thr | Asp | Phe | Thr | Leu | Thr | Ile | |
| 65 | | | | | 70 | | | | | 75 | | | | | 80 | |

| | | | | | | | | | | | | | | | | |
|---|---|---|---|---|---|---|---|---|---|---|---|---|---|---|---|---|
| agt | tca | gtg | cag | cct | gag | gac | ttc | gcc | acc | tat | tat | tgt | atg | cag | act | 288 |
| Ser | Ser | Val | Gln | Pro | Glu | Asp | Phe | Ala | Thr | Tyr | Tyr | Cys | Met | Gln | Thr | |
| | | | | 85 | | | | | 90 | | | | | 95 | | |

| | | | | | | | | | | | | | | | | |
|---|---|---|---|---|---|---|---|---|---|---|---|---|---|---|---|---|
| ctg | cag | acc | cct | ctg | acc | ttt | ggt | cag | gga | acc | aag | gtg | gaa | atc | aag | 336 |
| Leu | Gln | Thr | Pro | Leu | Thr | Phe | Gly | Gln | Gly | Thr | Lys | Val | Glu | Ile | Lys | |
| | | | 100 | | | | | 105 | | | | | 110 | | | |

| | | | | | | | | | | | | | | | | |
|---|---|---|---|---|---|---|---|---|---|---|---|---|---|---|---|---|
| cgt | acg | gtg | gct | gca | cca | tct | gtc | ttc | atc | ttc | ccg | cca | tct | gat | gag | 384 |
| Arg | Thr | Val | Ala | Ala | Pro | Ser | Val | Phe | Ile | Phe | Pro | Pro | Ser | Asp | Glu | |
| | | 115 | | | | | 120 | | | | | 125 | | | | |

| | | | | | | | | | | | | | | | | |
|---|---|---|---|---|---|---|---|---|---|---|---|---|---|---|---|---|
| cag | ttg | aaa | tct | gga | act | gcc | tct | gtt | gtg | tgc | ctg | ctg | aat | aac | ttc | 432 |
| Gln | Leu | Lys | Ser | Gly | Thr | Ala | Ser | Val | Val | Cys | Leu | Leu | Asn | Asn | Phe | |
| | 130 | | | | | 135 | | | | | 140 | | | | | |

| | | | | | | | | | | | | | | | | |
|---|---|---|---|---|---|---|---|---|---|---|---|---|---|---|---|---|
| tat | ccc | aga | gag | gcc | aaa | gta | cag | tgg | aag | gtg | gat | aac | gcc | ctc | caa | 480 |
| Tyr | Pro | Arg | Glu | Ala | Lys | Val | Gln | Trp | Lys | Val | Asp | Asn | Ala | Leu | Gln | |
| 145 | | | | | 150 | | | | | 155 | | | | | 160 | |

| | | | | | | | | | | | | | | | | |
|---|---|---|---|---|---|---|---|---|---|---|---|---|---|---|---|---|
| tcg | ggt | aac | tcc | cag | gag | agt | gtc | aca | gag | cag | gac | agc | aag | gac | agc | 528 |
| Ser | Gly | Asn | Ser | Gln | Glu | Ser | Val | Thr | Glu | Gln | Asp | Ser | Lys | Asp | Ser | |
| | | | | 165 | | | | | 170 | | | | | 175 | | |

| | | | | | | | | | | | | | | | | |
|---|---|---|---|---|---|---|---|---|---|---|---|---|---|---|---|---|
| acc | tac | agc | ctg | agc | agc | acc | ctg | acg | ctg | agc | aaa | gca | gac | tac | gag | 576 |
| Thr | Tyr | Ser | Leu | Ser | Ser | Thr | Leu | Thr | Leu | Ser | Lys | Ala | Asp | Tyr | Glu | |
| | | | 180 | | | | | 185 | | | | | 190 | | | |

| | | | | | | | | | | | | | | | | |
|---|---|---|---|---|---|---|---|---|---|---|---|---|---|---|---|---|
| aaa | cac | aaa | gtc | tac | gcc | tgc | gaa | gtc | acc | cat | cag | ggc | ctg | agc | tcg | 624 |
| Lys | His | Lys | Val | Tyr | Ala | Cys | Glu | Val | Thr | His | Gln | Gly | Leu | Ser | Ser | |
| | | 195 | | | | | 200 | | | | | 205 | | | | |

| | | | | | | | | | |
|---|---|---|---|---|---|---|---|---|---|
| ccc | gtc | aca | aag | agc | ttc | aac | agg | gga | gag | tgt | 657 |
| Pro | Val | Thr | Lys | Ser | Phe | Asn | Arg | Gly | Glu | Cys | |
| | 210 | | | | | 215 | | | | | |

<210> SEQ ID NO 4
<211> LENGTH: 219
<212> TYPE: PRT
<213> ORGANISM: Artificial Sequence
<220> FEATURE:
<223> OTHER INFORMATION: Synthetic Construct

<400> SEQUENCE: 4

```
Asp Ile Gln Met Thr Gln Ser Pro Ser Leu Ser Ala Ser Val Gly
1               5                  10                  15

Asp Arg Val Thr Ile Thr Cys Arg Ser Ser Gln Ser Leu Leu His Ser
            20                  25                  30

His Arg Tyr Asn Tyr Leu Asp Trp Tyr Gln Gln Lys Pro Gly Lys Ala
        35                  40                  45

Pro Lys Leu Leu Ile Tyr Leu Gly Ser Asn Arg Ala Ser Gly Val Pro
    50                  55                  60

Ser Arg Phe Ser Gly Ser Gly Ser Gly Thr Asp Phe Thr Leu Thr Ile
65                  70                  75                  80

Ser Ser Val Gln Pro Glu Asp Phe Ala Thr Tyr Tyr Cys Met Gln Thr
                85                  90                  95

Leu Gln Thr Pro Leu Thr Phe Gly Gln Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215
```

<210> SEQ ID NO 5
<211> LENGTH: 2037
<212> TYPE: DNA
<213> ORGANISM: Artificial Sequence
<220> FEATURE:
<223> OTHER INFORMATION: H-chain of anti-human Tie2 antibody
<220> FEATURE:
<221> NAME/KEY: CDS
<222> LOCATION: (1)..(2037)

<400> SEQUENCE: 5

```
gaa gtg cag ctg gtg gaa tct ggc ggc gga ctg gtg cag cct ggc gga    48
Glu Val Gln Leu Val Glu Ser Gly Gly Gly Leu Val Gln Pro Gly Gly
1               5                  10                  15 tct ctg aga ctg tct tgt gcc gcc tcc ggc ttc acc ttc gac gac tac    96
Ser Leu Arg Leu Ser Cys Ala Ala Ser Gly Phe Thr Phe Asp Asp Tyr
            20                  25                  30 gct atg cac tgg gtg cga cag gcc cct ggc aag gga ctg gaa tgg gtg    144
Ala Met His Trp Val Arg Gln Ala Pro Gly Lys Gly Leu Glu Trp Val
        35                  40                  45 gcc ggc atc tcc tgg aac tcc ggc tct atc gtg tac gcc gac tcc gtg    192
Ala Gly Ile Ser Trp Asn Ser Gly Ser Ile Val Tyr Ala Asp Ser Val
```

```
            50                  55                  60
aag ggc cgg ttc acc atc tcc cgg gac aac tcc aag aac acc ctg tac        240
Lys Gly Arg Phe Thr Ile Ser Arg Asp Asn Ser Lys Asn Thr Leu Tyr
 65                  70                  75                  80 ctg cag atg aac tcc ctg cgg gcc gag gac acc gcc gtg tac tac tgc        288
Leu Gln Met Asn Ser Leu Arg Ala Glu Asp Thr Ala Val Tyr Tyr Cys
                     85                  90                  95 gct aag gac atc cgg gaa cag ctg gtg gaa gat gcc ttc gac atc tgg        336
Ala Lys Asp Ile Arg Glu Gln Leu Val Glu Asp Ala Phe Asp Ile Trp
                100                 105                 110 ggc cag ggc acc ctc gtg acc gtg tcc tct gct tct acc aag ggc ccc        384
Gly Gln Gly Thr Leu Val Thr Val Ser Ser Ala Ser Thr Lys Gly Pro
            115                 120                 125 tcc gtg ttc cct ctg gcc cct tcc agc aag tct acc tct ggc ggc aca        432
Ser Val Phe Pro Leu Ala Pro Ser Ser Lys Ser Thr Ser Gly Gly Thr
        130                 135                 140 gcc gct ctg ggc tgc ctc gtg aag gac tac ttc ccc gag ccc gtg aca        480
Ala Ala Leu Gly Cys Leu Val Lys Asp Tyr Phe Pro Glu Pro Val Thr
145                 150                 155                 160 gtg tct tgg aac tct ggc gcc ctg aca tct ggc gtg cac acc ttc cct        528
Val Ser Trp Asn Ser Gly Ala Leu Thr Ser Gly Val His Thr Phe Pro
                    165                 170                 175 gct gtg ctg cag tcc tcc ggc ctg tac tcc ctg tcc gtc gtg act            576
Ala Val Leu Gln Ser Ser Gly Leu Tyr Ser Leu Ser Val Val Thr
                180                 185                 190 gtg ccc tcc agc tct ctg ggc acc cag acc tac atc tgc aac gtg aac        624
Val Pro Ser Ser Ser Leu Gly Thr Gln Thr Tyr Ile Cys Asn Val Asn
            195                 200                 205 cac aag ccc tcc aac acc aag gtg gac aag aag gtg gaa ccc aag tcc        672
His Lys Pro Ser Asn Thr Lys Val Asp Lys Lys Val Glu Pro Lys Ser
        210                 215                 220 tgc ggc agc gag gtg cag ctg gtg gaa agt ggg gga ggc ctg gtg cag        720
Cys Gly Ser Glu Val Gln Leu Val Glu Ser Gly Gly Gly Leu Val Gln
225                 230                 235                 240 cca ggt gga agc ctg aga ctg agc tgc gcc gct tct ggc ttt acc ttt        768
Pro Gly Gly Ser Leu Arg Leu Ser Cys Ala Ala Ser Gly Phe Thr Phe
                    245                 250                 255 gat gat tat gcc atg cat tgg gtg cgc cag gct cca ggg aaa ggc ctg        816
Asp Asp Tyr Ala Met His Trp Val Arg Gln Ala Pro Gly Lys Gly Leu
                260                 265                 270 gaa tgg gtg gca ggg atc agc tgg aac agc ggc agc atc gtg tat gct        864
Glu Trp Val Ala Gly Ile Ser Trp Asn Ser Gly Ser Ile Val Tyr Ala
            275                 280                 285 gat agc gtg aag ggg cgc ttt aca atc agc aga gac aac agc aag aat        912
Asp Ser Val Lys Gly Arg Phe Thr Ile Ser Arg Asp Asn Ser Lys Asn
        290                 295                 300 act ctg tac ctg cag atg aat agc ctg cgc gct gag gat aca gct gtg        960
Thr Leu Tyr Leu Gln Met Asn Ser Leu Arg Ala Glu Asp Thr Ala Val
305                 310                 315                 320 tat tac tgt gcc aag gat att cgc gag cag ctg gtg gaa gat gct ttt       1008
Tyr Tyr Cys Ala Lys Asp Ile Arg Glu Gln Leu Val Glu Asp Ala Phe
                    325                 330                 335 gat att tgg ggg cag ggt aca ctc gtg aca gtg tct agc gcc tcc acc       1056
Asp Ile Trp Gly Gln Gly Thr Leu Val Thr Val Ser Ser Ala Ser Thr
                340                 345                 350 aag ggc cca agc gtg ttc cca ctg gct ccc agc tcc aag agc acc tcc       1104
Lys Gly Pro Ser Val Phe Pro Leu Ala Pro Ser Ser Lys Ser Thr Ser
            355                 360                 365 ggt gga act gct gcc ctg ggc tgt ctc gtg aaa gat tat ttt cct gag       1152
```

|  |  |  |  |  |  |  |  |  |  |  |  |  |  |  |  |
|---|---|---|---|---|---|---|---|---|---|---|---|---|---|---|---|
| Gly | Gly | Thr | Ala | Ala | Leu | Gly | Cys | Leu | Val | Lys | Asp | Tyr | Phe | Pro | Glu |
|  | 370 |  |  |  | 375 |  |  |  | 380 |  |  |  |  |  |  |

| cct | gtg | act | gtg | tcc | tgg | aat | agc | ggc | gct | ctg | acc | agc | gga | gtg | cat | 1200 |
|---|---|---|---|---|---|---|---|---|---|---|---|---|---|---|---|---|
| Pro | Val | Thr | Val | Ser | Trp | Asn | Ser | Gly | Ala | Leu | Thr | Ser | Gly | Val | His |  |
| 385 |  |  |  |  | 390 |  |  |  |  | 395 |  |  |  |  | 400 |  |

| acc | ttt | cca | gcc | gtg | ctg | cag | agc | agc | ggc | ctg | tat | agc | ctg | tcc | agc | 1248 |
|---|---|---|---|---|---|---|---|---|---|---|---|---|---|---|---|---|
| Thr | Phe | Pro | Ala | Val | Leu | Gln | Ser | Ser | Gly | Leu | Tyr | Ser | Leu | Ser | Ser |  |
|  |  |  |  | 405 |  |  |  |  | 410 |  |  |  |  | 415 |  |  |

| gtc | gtg | acc | gtg | cct | tcc | tct | agc | ctg | gga | aca | cag | aca | tat | atc | tgt | 1296 |
|---|---|---|---|---|---|---|---|---|---|---|---|---|---|---|---|---|
| Val | Val | Thr | Val | Pro | Ser | Ser | Ser | Leu | Gly | Thr | Gln | Thr | Tyr | Ile | Cys |  |
|  |  |  | 420 |  |  |  |  | 425 |  |  |  |  | 430 |  |  |  |

| aat | gtg | aat | cat | aag | ccc | agt | aat | acc | aaa | gtg | gat | aag | aaa | gtg | gaa | 1344 |
|---|---|---|---|---|---|---|---|---|---|---|---|---|---|---|---|---|
| Asn | Val | Asn | His | Lys | Pro | Ser | Asn | Thr | Lys | Val | Asp | Lys | Lys | Val | Glu |  |
|  |  |  |  | 435 |  |  |  |  | 440 |  |  |  |  | 445 |  |  |

| cct | aag | agc | tgc | gac | aag | acc | cac | acc | tgt | ccc | cct | tgt | cct | gcc | cct | 1392 |
|---|---|---|---|---|---|---|---|---|---|---|---|---|---|---|---|---|
| Pro | Lys | Ser | Cys | Asp | Lys | Thr | His | Thr | Cys | Pro | Pro | Cys | Pro | Ala | Pro |  |
|  | 450 |  |  |  |  | 455 |  |  |  |  | 460 |  |  |  |  |  |

| gaa | gct | gct | ggc | ggc | cct | tct | gtg | ttt | ctg | ttc | ccc | cca | aag | cct | aag | 1440 |
|---|---|---|---|---|---|---|---|---|---|---|---|---|---|---|---|---|
| Glu | Ala | Ala | Gly | Gly | Pro | Ser | Val | Phe | Leu | Phe | Pro | Pro | Lys | Pro | Lys |  |
| 465 |  |  |  |  | 470 |  |  |  |  | 475 |  |  |  |  | 480 |  |

| gac | acc | ctg | atg | gcc | tcc | cgg | acc | ccc | gaa | gtg | acc | tgc | gtg | gtg | gtg | 1488 |
|---|---|---|---|---|---|---|---|---|---|---|---|---|---|---|---|---|
| Asp | Thr | Leu | Met | Ala | Ser | Arg | Thr | Pro | Glu | Val | Thr | Cys | Val | Val | Val |  |
|  |  |  |  | 485 |  |  |  |  | 490 |  |  |  |  | 495 |  |  |

| gat | gtg | tcc | cac | gag | gac | cct | gaa | gtg | aag | ttc | aat | tgg | tac | gtg | gac | 1536 |
|---|---|---|---|---|---|---|---|---|---|---|---|---|---|---|---|---|
| Asp | Val | Ser | His | Glu | Asp | Pro | Glu | Val | Lys | Phe | Asn | Trp | Tyr | Val | Asp |  |
|  |  |  | 500 |  |  |  |  | 505 |  |  |  |  | 510 |  |  |  |

| ggc | gtg | gaa | gtg | cac | aac | gcc | aag | acc | aag | cct | aga | gag | gaa | cag | tac | 1584 |
|---|---|---|---|---|---|---|---|---|---|---|---|---|---|---|---|---|
| Gly | Val | Glu | Val | His | Asn | Ala | Lys | Thr | Lys | Pro | Arg | Glu | Glu | Gln | Tyr |  |
|  |  | 515 |  |  |  |  | 520 |  |  |  |  | 525 |  |  |  |  |

| aac | tcc | acc | tac | cgg | gtg | gtg | tcc | gtg | ctg | aca | gtg | ctg | cat | cag | gac | 1632 |
|---|---|---|---|---|---|---|---|---|---|---|---|---|---|---|---|---|
| Asn | Ser | Thr | Tyr | Arg | Val | Val | Ser | Val | Leu | Thr | Val | Leu | His | Gln | Asp |  |
|  | 530 |  |  |  |  | 535 |  |  |  |  | 540 |  |  |  |  |  |

| tgg | ctg | aac | ggc | aaa | gag | tac | aag | tgc | aag | gtg | tcc | aac | aag | gcc | ctg | 1680 |
|---|---|---|---|---|---|---|---|---|---|---|---|---|---|---|---|---|
| Trp | Leu | Asn | Gly | Lys | Glu | Tyr | Lys | Cys | Lys | Val | Ser | Asn | Lys | Ala | Leu |  |
| 545 |  |  |  |  | 550 |  |  |  |  | 555 |  |  |  |  | 560 |  |

| ccc | gcc | tcc | atc | gaa | aag | acc | atc | tcc | aag | gcc | aag | ggc | cag | ccc | cgg | 1728 |
|---|---|---|---|---|---|---|---|---|---|---|---|---|---|---|---|---|
| Pro | Ala | Ser | Ile | Glu | Lys | Thr | Ile | Ser | Lys | Ala | Lys | Gly | Gln | Pro | Arg |  |
|  |  |  |  | 565 |  |  |  |  | 570 |  |  |  |  | 575 |  |  |

| gaa | ccc | cag | gtg | tac | aca | ctg | ccc | cct | agc | agg | gac | gag | ctg | acc | aag | 1776 |
|---|---|---|---|---|---|---|---|---|---|---|---|---|---|---|---|---|
| Glu | Pro | Gln | Val | Tyr | Thr | Leu | Pro | Pro | Ser | Arg | Asp | Glu | Leu | Thr | Lys |  |
|  |  |  | 580 |  |  |  |  | 585 |  |  |  |  | 590 |  |  |  |

| aac | cag | gtg | tcc | ctg | acc | tgt | ctc | gtg | aag | ggc | ttc | tac | ccc | tcc | gat | 1824 |
|---|---|---|---|---|---|---|---|---|---|---|---|---|---|---|---|---|
| Asn | Gln | Val | Ser | Leu | Thr | Cys | Leu | Val | Lys | Gly | Phe | Tyr | Pro | Ser | Asp |  |
|  | 595 |  |  |  |  | 600 |  |  |  |  | 605 |  |  |  |  |  |

| atc | gcc | gtg | gaa | tgg | gag | tcc | aac | ggc | cag | cct | gag | aac | aac | tat | aag | 1872 |
|---|---|---|---|---|---|---|---|---|---|---|---|---|---|---|---|---|
| Ile | Ala | Val | Glu | Trp | Glu | Ser | Asn | Gly | Gln | Pro | Glu | Asn | Asn | Tyr | Lys |  |
| 610 |  |  |  |  | 615 |  |  |  |  | 620 |  |  |  |  |  |  |

| acc | acc | ccc | cct | gtg | ctg | gac | tcc | gac | ggc | tca | ttt | ttt | ctg | tac | tcc | 1920 |
|---|---|---|---|---|---|---|---|---|---|---|---|---|---|---|---|---|
| Thr | Thr | Pro | Pro | Val | Leu | Asp | Ser | Asp | Gly | Ser | Phe | Phe | Leu | Tyr | Ser |  |
| 625 |  |  |  |  | 630 |  |  |  |  | 635 |  |  |  |  | 640 |  |

| aag | ctg | acc | gtg | gac | aag | tcc | cgg | tgg | cag | cag | ggc | aac | gtg | ttc | tcc | 1968 |
|---|---|---|---|---|---|---|---|---|---|---|---|---|---|---|---|---|
| Lys | Leu | Thr | Val | Asp | Lys | Ser | Arg | Trp | Gln | Gln | Gly | Asn | Val | Phe | Ser |  |
|  |  |  |  | 645 |  |  |  |  | 650 |  |  |  |  | 655 |  |  |

| tgc | agc | gtg | atg | cac | gag | gcc | ctg | cac | aac | cac | tac | acc | cag | aag | tcc | 2016 |
|---|---|---|---|---|---|---|---|---|---|---|---|---|---|---|---|---|
| Cys | Ser | Val | Met | His | Glu | Ala | Leu | His | Asn | His | Tyr | Thr | Gln | Lys | Ser |  |
|  |  |  | 660 |  |  |  |  | 665 |  |  |  |  | 670 |  |  |  |

| ctg | tcc | ctg | agc | ccc | ggc | aaa |  |  |  |  |  |  |  |  |  | 2037 |
|---|---|---|---|---|---|---|---|---|---|---|---|---|---|---|---|---|
| Leu | Ser | Leu | Ser | Pro | Gly | Lys |  |  |  |  |  |  |  |  |  |  |
|  |  |  | 675 |  |  |  |  |  |  |  |  |  |  |  |  |  |

```
<210> SEQ ID NO 6
<211> LENGTH: 679
<212> TYPE: PRT
<213> ORGANISM: Artificial Sequence
<220> FEATURE:
<223> OTHER INFORMATION: Synthetic Construct

<400> SEQUENCE: 6

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ala Gly Ile Ser Trp Asn Ser Gly Ser Ile Val Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Ile Arg Glu Gln Leu Val Glu Asp Ala Phe Asp Ile Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Lys Val Glu Pro Lys Ser
    210                 215                 220

Cys Gly Ser Glu Val Gln Leu Val Glu Ser Gly Gly Gly Leu Val Gln
225                 230                 235                 240

Pro Gly Gly Ser Leu Arg Leu Ser Cys Ala Ala Ser Gly Phe Thr Phe
                245                 250                 255

Asp Asp Tyr Ala Met His Trp Val Arg Gln Ala Pro Gly Lys Gly Leu
            260                 265                 270

Glu Trp Val Ala Gly Ile Ser Trp Asn Ser Gly Ser Ile Val Tyr Ala
        275                 280                 285

Asp Ser Val Lys Gly Arg Phe Thr Ile Ser Arg Asp Asn Ser Lys Asn
    290                 295                 300

Thr Leu Tyr Leu Gln Met Asn Ser Leu Arg Ala Glu Asp Thr Ala Val
305                 310                 315                 320

Tyr Tyr Cys Ala Lys Asp Ile Arg Glu Gln Leu Val Glu Asp Ala Phe
                325                 330                 335

Asp Ile Trp Gly Gln Gly Thr Leu Val Thr Val Ser Ser Ala Ser Thr
            340                 345                 350

Lys Gly Pro Ser Val Phe Pro Leu Ala Pro Ser Ser Lys Ser Thr Ser
        355                 360                 365
```

```
Gly Gly Thr Ala Ala Leu Gly Cys Leu Val Lys Asp Tyr Phe Pro Glu
    370                 375                 380

Pro Val Thr Val Ser Trp Asn Ser Gly Ala Leu Thr Ser Gly Val His
385                 390                 395                 400

Thr Phe Pro Ala Val Leu Gln Ser Ser Gly Leu Tyr Ser Leu Ser Ser
                405                 410                 415

Val Val Thr Val Pro Ser Ser Ser Leu Gly Thr Gln Thr Tyr Ile Cys
            420                 425                 430

Asn Val Asn His Lys Pro Ser Asn Thr Lys Val Asp Lys Lys Val Glu
        435                 440                 445

Pro Lys Ser Cys Asp Lys Thr His Thr Cys Pro Pro Cys Pro Ala Pro
450                 455                 460

Glu Ala Ala Gly Gly Pro Ser Val Phe Leu Phe Pro Pro Lys Pro Lys
465                 470                 475                 480

Asp Thr Leu Met Ala Ser Arg Thr Pro Glu Val Thr Cys Val Val Val
                485                 490                 495

Asp Val Ser His Glu Asp Pro Glu Val Lys Phe Asn Trp Tyr Val Asp
            500                 505                 510

Gly Val Glu Val His Asn Ala Lys Thr Lys Pro Arg Glu Glu Gln Tyr
        515                 520                 525

Asn Ser Thr Tyr Arg Val Val Ser Val Leu Thr Val Leu His Gln Asp
530                 535                 540

Trp Leu Asn Gly Lys Glu Tyr Lys Cys Lys Val Ser Asn Lys Ala Leu
545                 550                 555                 560

Pro Ala Ser Ile Glu Lys Thr Ile Ser Lys Ala Lys Gly Gln Pro Arg
                565                 570                 575

Glu Pro Gln Val Tyr Thr Leu Pro Pro Ser Arg Asp Glu Leu Thr Lys
            580                 585                 590

Asn Gln Val Ser Leu Thr Cys Leu Val Lys Gly Phe Tyr Pro Ser Asp
        595                 600                 605

Ile Ala Val Glu Trp Glu Ser Asn Gly Gln Pro Glu Asn Asn Tyr Lys
610                 615                 620

Thr Thr Pro Pro Val Leu Asp Ser Asp Gly Ser Phe Phe Leu Tyr Ser
625                 630                 635                 640

Lys Leu Thr Val Asp Lys Ser Arg Trp Gln Gln Gly Asn Val Phe Ser
                645                 650                 655

Cys Ser Val Met His Glu Ala Leu His Asn His Tyr Thr Gln Lys Ser
            660                 665                 670

Leu Ser Leu Ser Pro Gly Lys
        675

<210> SEQ ID NO 7
<211> LENGTH: 2037
<212> TYPE: DNA
<213> ORGANISM: Artificial Sequence
<220> FEATURE:
<223> OTHER INFORMATION: H-chain of anti-human Tie2 antibody
<220> FEATURE:
<221> NAME/KEY: CDS
<222> LOCATION: (1)..(2037)

<400> SEQUENCE: 7 gag gtg cag ctg gtg gaa tcc ggc gga ggc ctg gtg cag cct ggc ggc      48
Glu Val Gln Leu Val Glu Ser Gly Gly Gly Leu Val Gln Pro Gly Gly
1               5                   10                  15 tct ctg aga ctg tcc tgt gcc gcc tcc ggc ttc acc ttc gac gac tac      96
Ser Leu Arg Leu Ser Cys Ala Ala Ser Gly Phe Thr Phe Asp Asp Tyr
```

```
                20                      25                      30
gcc atg cac tgg gtc cga cag gcc cct ggc aag ggc ctg gaa tgg gtg    144
Ala Met His Trp Val Arg Gln Ala Pro Gly Lys Gly Leu Glu Trp Val
         35                      40                      45 gcc ggc atc tcc tgg aac tcc ggc tcc atc gtg tac gcc gac tcc gtg    192
Ala Gly Ile Ser Trp Asn Ser Gly Ser Ile Val Tyr Ala Asp Ser Val
 50                      55                      60 aag ggc cgg ttc acc atc tcc cgg gac aac tcc aag aac acc ctg tac    240
Lys Gly Arg Phe Thr Ile Ser Arg Asp Asn Ser Lys Asn Thr Leu Tyr
 65                      70                      75                      80 ctg cag atg aac tcc ctg cgg gcc gag gac acc gcc gtg tac tac tgc    288
Leu Gln Met Asn Ser Leu Arg Ala Glu Asp Thr Ala Val Tyr Tyr Cys
                 85                      90                      95 gcc aag gac atc aga gag cag ctg gtc gag gac gcc ttc gac atc tgg    336
Ala Lys Asp Ile Arg Glu Gln Leu Val Glu Asp Ala Phe Asp Ile Trp
            100                     105                     110 ggc cag ggc acc ctg gtc acc gtg tcc tca gcc tcc acc aag ggc cca    384
Gly Gln Gly Thr Leu Val Thr Val Ser Ser Ala Ser Thr Lys Gly Pro
       115                     120                     125 tcg gtc ttc ccc ctg gca ccc tcc tcc aag agc acc tct ggg ggc aca    432
Ser Val Phe Pro Leu Ala Pro Ser Ser Lys Ser Thr Ser Gly Gly Thr
130                     135                     140 gcg gcc ctg ggc tgc ctg gtc aag gac tac ttc ccc gaa ccg gtg acg    480
Ala Ala Leu Gly Cys Leu Val Lys Asp Tyr Phe Pro Glu Pro Val Thr
145                     150                     155                     160 gtg tcg tgg aac tca ggc gcc ctg acc agc ggc gtg cac acc ttc ccg    528
Val Ser Trp Asn Ser Gly Ala Leu Thr Ser Gly Val His Thr Phe Pro
                    165                     170                     175 gct gtc cta cag tcc tca gga ctc tac tcc ctt agt agc gtg gtg acc    576
Ala Val Leu Gln Ser Ser Gly Leu Tyr Ser Leu Ser Ser Val Val Thr
               180                     185                     190 gtg ccc tcc agc agc ttg ggc acc cag acc tac atc tgc aac gtg aat    624
Val Pro Ser Ser Ser Leu Gly Thr Gln Thr Tyr Ile Cys Asn Val Asn
          195                     200                     205 cac aag ccc agc aac acc aag gtg gac aag aaa gtt gag ccc aaa tct    672
His Lys Pro Ser Asn Thr Lys Val Asp Lys Lys Val Glu Pro Lys Ser
     210                     215                     220 tgt gga tcc gag gtg cag ctg gtg gaa tcc ggc gga ggc ctg gtg cag    720
Cys Gly Ser Glu Val Gln Leu Val Glu Ser Gly Gly Gly Leu Val Gln
225                     230                     235                     240 cct ggc ggc tct ctg aga ctg tcc tgt gcc gcc tcc ggc ttc acc ttc    768
Pro Gly Gly Ser Leu Arg Leu Ser Cys Ala Ala Ser Gly Phe Thr Phe
                    245                     250                     255 gac gac tac gcc atg cac tgg gtc cga cag gcc cct ggc aag ggc ctg    816
Asp Asp Tyr Ala Met His Trp Val Arg Gln Ala Pro Gly Lys Gly Leu
               260                     265                     270 gaa tgg gtg gcc ggc atc tcc tgg aac tcc ggc tcc atc gtg tac gcc    864
Glu Trp Val Ala Gly Ile Ser Trp Asn Ser Gly Ser Ile Val Tyr Ala
          275                     280                     285 gac tcc gtg aag ggc cgg ttc acc atc tcc cgg gac aac tcc aag aac    912
Asp Ser Val Lys Gly Arg Phe Thr Ile Ser Arg Asp Asn Ser Lys Asn
     290                     295                     300 acc ctg tac ctg cag atg aac tcc ctg cgg gcc gag gac acc gcc gtg    960
Thr Leu Tyr Leu Gln Met Asn Ser Leu Arg Ala Glu Asp Thr Ala Val
305                     310                     315                     320 tac tac tgc gcc aag gac atc aga gag cag ctg gtc gag gac gcc ttc    1008
Tyr Tyr Cys Ala Lys Asp Ile Arg Glu Gln Leu Val Glu Asp Ala Phe
                    325                     330                     335 gac atc tgg ggc cag ggc acc ctg gtc acc gtg tcc tca gcc tcc acc    1056
```

```
Asp Ile Trp Gly Gln Gly Thr Leu Val Thr Val Ser Ser Ala Ser Thr
            340                 345                 350 aag ggc cca tcg gtc ttc ccc ctg gca ccc tcc tcc aag agc acc tct    1104
Lys Gly Pro Ser Val Phe Pro Leu Ala Pro Ser Ser Lys Ser Thr Ser
            355                 360                 365 ggg ggc aca gcg gcc ctg ggc tgc ctg gtc aag gac tac ttc ccc gaa    1152
Gly Gly Thr Ala Ala Leu Gly Cys Leu Val Lys Asp Tyr Phe Pro Glu
        370                 375                 380 ccg gtg acg gtg tcg tgg aac tca ggc gcc ctg acc agc ggc gtg cac    1200
Pro Val Thr Val Ser Trp Asn Ser Gly Ala Leu Thr Ser Gly Val His
385                 390                 395                 400 acc ttc ccg gct gtc cta cag tcc tca gga ctc tac tcc ctt agt agc    1248
Thr Phe Pro Ala Val Leu Gln Ser Ser Gly Leu Tyr Ser Leu Ser Ser
                405                 410                 415 gtg gtg acc gtg ccc tcc agc agc ttg ggc acc cag acc tac atc tgc    1296
Val Val Thr Val Pro Ser Ser Ser Leu Gly Thr Gln Thr Tyr Ile Cys
            420                 425                 430 aac gtg aat cac aag ccc agc aac acc aag gtg gac aag aaa gtt gag    1344
Asn Val Asn His Lys Pro Ser Asn Thr Lys Val Asp Lys Lys Val Glu
            435                 440                 445 ccc aaa tct tgt gac aaa act cac aca tgc cca ccg tgc cca gca cct    1392
Pro Lys Ser Cys Asp Lys Thr His Thr Cys Pro Pro Cys Pro Ala Pro
450                 455                 460 gaa ctc ctg ggg gga ccg tca gtc ttc ctc ttc ccc cca aaa ccc aag    1440
Glu Leu Leu Gly Gly Pro Ser Val Phe Leu Phe Pro Pro Lys Pro Lys
465                 470                 475                 480 gac acc ctc atg atc tcc cgg acc cct gag gtc aca tgc gtg gtg gtg    1488
Asp Thr Leu Met Ile Ser Arg Thr Pro Glu Val Thr Cys Val Val Val
                485                 490                 495 gac gtg agc cac gaa gac cct gag gtc aag ttc aac tgg tac gtg gac    1536
Asp Val Ser His Glu Asp Pro Glu Val Lys Phe Asn Trp Tyr Val Asp
            500                 505                 510 ggc gtg gag gtg cat aat gcc aag aca aag ccg cgg gag gag cag tac    1584
Gly Val Glu Val His Asn Ala Lys Thr Lys Pro Arg Glu Glu Gln Tyr
            515                 520                 525 aac agc acg tac cgt gtg gtc agc gtc ctc acc gtc ctg cac cag gac    1632
Asn Ser Thr Tyr Arg Val Val Ser Val Leu Thr Val Leu His Gln Asp
530                 535                 540 tgg ctg aat ggc aag gag tac aag tgc aag gtc tcc aac aaa gcc ctc    1680
Trp Leu Asn Gly Lys Glu Tyr Lys Cys Lys Val Ser Asn Lys Ala Leu
545                 550                 555                 560 cca gcc ccc atc gag aaa acc atc tcc aaa gcc aaa ggg cag ccc cga    1728
Pro Ala Pro Ile Glu Lys Thr Ile Ser Lys Ala Lys Gly Gln Pro Arg
                565                 570                 575 gaa cca cag gtg tac acc ctg ccc cca tcc cgg gat gag ctg acc aag    1776
Glu Pro Gln Val Tyr Thr Leu Pro Pro Ser Arg Asp Glu Leu Thr Lys
            580                 585                 590 aac cag gtc agc ctg acc tgc ctg gtc aaa ggc ttc tat ccc agc gac    1824
Asn Gln Val Ser Leu Thr Cys Leu Val Lys Gly Phe Tyr Pro Ser Asp
            595                 600                 605 atc gcc gtg gag tgg gag agc aat ggg cag ccg gag aac aac tac aag    1872
Ile Ala Val Glu Trp Glu Ser Asn Gly Gln Pro Glu Asn Asn Tyr Lys
        610                 615                 620 acc acg cct ccc gtg ctg gac tcc gac ggc tcc ttc ttc ctc tac agc    1920
Thr Thr Pro Pro Val Leu Asp Ser Asp Gly Ser Phe Phe Leu Tyr Ser
625                 630                 635                 640 aag ctc acc gtg gac aag agc agg tgg cag cag ggg aac gtc ttc tca    1968
Lys Leu Thr Val Asp Lys Ser Arg Trp Gln Gln Gly Asn Val Phe Ser
                645                 650                 655
```

```
tgc tcc gtg atg cat gag gct ctg cac aac cac tac acg cag aag agc    2016
Cys Ser Val Met His Glu Ala Leu His Asn His Tyr Thr Gln Lys Ser
            660                 665                 670 ctc tcc ctg tct ccg ggt aaa                                         2037
Leu Ser Leu Ser Pro Gly Lys
        675

<210> SEQ ID NO 8
<211> LENGTH: 679
<212> TYPE: PRT
<213> ORGANISM: Artificial Sequence
<220> FEATURE:
<223> OTHER INFORMATION: Synthetic Construct

<400> SEQUENCE: 8

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ala Gly Ile Ser Trp Asn Ser Gly Ser Ile Val Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Ile Arg Glu Gln Leu Val Glu Asp Ala Phe Asp Ile Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Val Glu Pro Lys Ser
    210                 215                 220

Cys Gly Ser Glu Val Gln Leu Val Glu Ser Gly Gly Gly Leu Val Gln
225                 230                 235                 240

Pro Gly Gly Ser Leu Arg Leu Ser Cys Ala Ala Ser Gly Phe Thr Phe
                245                 250                 255

Asp Asp Tyr Ala Met His Trp Val Arg Gln Ala Pro Gly Lys Gly Leu
            260                 265                 270

Glu Trp Val Ala Gly Ile Ser Trp Asn Ser Gly Ser Ile Val Tyr Ala
        275                 280                 285

Asp Ser Val Lys Gly Arg Phe Thr Ile Ser Arg Asp Asn Ser Lys Asn
    290                 295                 300

Thr Leu Tyr Leu Gln Met Asn Ser Leu Arg Ala Glu Asp Thr Ala Val
305                 310                 315                 320

Tyr Tyr Cys Ala Lys Asp Ile Arg Glu Gln Leu Val Glu Asp Ala Phe
```

```
            325                 330                 335
Asp Ile Trp Gly Gln Gly Thr Leu Val Thr Val Ser Ser Ala Ser Thr
            340                 345                 350
Lys Gly Pro Ser Val Phe Pro Leu Ala Pro Ser Ser Lys Ser Thr Ser
        355                 360                 365
Gly Gly Thr Ala Ala Leu Gly Cys Leu Val Lys Asp Tyr Phe Pro Glu
    370                 375                 380
Pro Val Thr Val Ser Trp Asn Ser Gly Ala Leu Thr Ser Gly Val His
385                 390                 395                 400
Thr Phe Pro Ala Val Leu Gln Ser Ser Gly Leu Tyr Ser Leu Ser Ser
                405                 410                 415
Val Val Thr Val Pro Ser Ser Leu Gly Thr Gln Thr Tyr Ile Cys
            420                 425                 430
Asn Val Asn His Lys Pro Ser Asn Thr Lys Val Asp Lys Lys Val Glu
            435                 440                 445
Pro Lys Ser Cys Asp Lys Thr His Thr Cys Pro Pro Cys Pro Ala Pro
        450                 455                 460
Glu Leu Leu Gly Gly Pro Ser Val Phe Leu Phe Pro Pro Lys Pro Lys
465                 470                 475                 480
Asp Thr Leu Met Ile Ser Arg Thr Pro Glu Val Thr Cys Val Val Val
                485                 490                 495
Asp Val Ser His Glu Asp Pro Glu Val Lys Phe Asn Trp Tyr Val Asp
            500                 505                 510
Gly Val Glu Val His Asn Ala Lys Thr Lys Pro Arg Glu Glu Gln Tyr
        515                 520                 525
Asn Ser Thr Tyr Arg Val Val Ser Val Leu Thr Val Leu His Gln Asp
    530                 535                 540
Trp Leu Asn Gly Lys Glu Tyr Lys Cys Lys Val Ser Asn Lys Ala Leu
545                 550                 555                 560
Pro Ala Pro Ile Glu Lys Thr Ile Ser Lys Ala Lys Gly Gln Pro Arg
                565                 570                 575
Glu Pro Gln Val Tyr Thr Leu Pro Pro Ser Arg Asp Glu Leu Thr Lys
            580                 585                 590
Asn Gln Val Ser Leu Thr Cys Leu Val Lys Gly Phe Tyr Pro Ser Asp
        595                 600                 605
Ile Ala Val Glu Trp Glu Ser Asn Gly Gln Pro Glu Asn Asn Tyr Lys
    610                 615                 620
Thr Thr Pro Pro Val Leu Asp Ser Asp Gly Ser Phe Phe Leu Tyr Ser
625                 630                 635                 640
Lys Leu Thr Val Asp Lys Ser Arg Trp Gln Gln Gly Asn Val Phe Ser
                645                 650                 655
Cys Ser Val Met His Glu Ala Leu His Asn His Tyr Thr Gln Lys Ser
            660                 665                 670
Leu Ser Leu Ser Pro Gly Lys
            675

<210> SEQ ID NO 9
<211> LENGTH: 2028
<212> TYPE: DNA
<213> ORGANISM: Artificial Sequence
<220> FEATURE:
<223> OTHER INFORMATION: H-chain of anti-human Tie2 antibody
<220> FEATURE:
<221> NAME/KEY: CDS
<222> LOCATION: (1)..(2028)
```

-continued

<400> SEQUENCE: 9

```
gag gtg cag ctg gtg gaa tcc ggc gga ggc ctg gtg cag cct ggc ggc      48
Glu Val Gln Leu Val Glu Ser Gly Gly Gly Leu Val Gln Pro Gly Gly
1               5                   10                  15 tct ctg aga ctg tcc tgt gcc gcc tcc ggc ttc acc ttc gac gac tac      96
Ser Leu Arg Leu Ser Cys Ala Ala Ser Gly Phe Thr Phe Asp Asp Tyr
            20                  25                  30 gcc atg cac tgg gtc cga cag gcc cct ggc aag ggc ctg gaa tgg gtg     144
Ala Met His Trp Val Arg Gln Ala Pro Gly Lys Gly Leu Glu Trp Val
        35                  40                  45 gcc ggc atc tcc tgg aac tcc ggc tcc atc gtg tac gcc gac tcc gtg     192
Ala Gly Ile Ser Trp Asn Ser Gly Ser Ile Val Tyr Ala Asp Ser Val
    50                  55                  60 aag ggc cgg ttc acc atc tcc cgg gac aac tcc aag aac acc ctg tac     240
Lys Gly Arg Phe Thr Ile Ser Arg Asp Asn Ser Lys Asn Thr Leu Tyr
65                  70                  75                  80 ctg cag atg aac tcc ctg cgg gcc gag gac acc gcc gtg tac tac tgc     288
Leu Gln Met Asn Ser Leu Arg Ala Glu Asp Thr Ala Val Tyr Tyr Cys
                85                  90                  95 gcc aag gac atc aga gag cag ctg gtc gag gac gcc ttc gac atc tgg     336
Ala Lys Asp Ile Arg Glu Gln Leu Val Glu Asp Ala Phe Asp Ile Trp
            100                 105                 110 ggc cag ggc acc ctg gtc acc gtg tcc tca gcc tcc acc aag ggc cca     384
Gly Gln Gly Thr Leu Val Thr Val Ser Ser Ala Ser Thr Lys Gly Pro
        115                 120                 125 tcg gtc ttc ccc ctg gca ccc tcc tcc aag agc acc tct ggg ggc aca     432
Ser Val Phe Pro Leu Ala Pro Ser Ser Lys Ser Thr Ser Gly Gly Thr
    130                 135                 140 gcg gcc ctg ggc tgc ctg gtc aag gac tac ttc ccc gaa ccg gtg acg     480
Ala Ala Leu Gly Cys Leu Val Lys Asp Tyr Phe Pro Glu Pro Val Thr
145                 150                 155                 160 gtg tcg tgg aac tca ggc gcc ctg acc agc ggc gtg cac acc ttc ccg     528
Val Ser Trp Asn Ser Gly Ala Leu Thr Ser Gly Val His Thr Phe Pro
                165                 170                 175 gct gtc cta cag tcc tca gga ctc tac tcc ctt agt agc gtg gtg acc     576
Ala Val Leu Gln Ser Ser Gly Leu Tyr Ser Leu Ser Ser Val Val Thr
            180                 185                 190 gtg ccc tcc agc agc ttg ggc acc cag acc tac atc tgc aac gtg aat     624
Val Pro Ser Ser Ser Leu Gly Thr Gln Thr Tyr Ile Cys Asn Val Asn
        195                 200                 205 cac aag ccc agc aac acc aag gtg gac aag aaa gtt gag ccc aaa tct     672
His Lys Pro Ser Asn Thr Lys Val Asp Lys Lys Val Glu Pro Lys Ser
    210                 215                 220 tgt gga tcc gag gtg cag ctg gtg gaa tcc ggc gga ggc ctg gtg cag     720
Cys Gly Ser Glu Val Gln Leu Val Glu Ser Gly Gly Gly Leu Val Gln
225                 230                 235                 240 cct ggc ggc tct ctg aga ctg tcc tgt gcc gcc tcc ggc ttc acc ttc     768
Pro Gly Gly Ser Leu Arg Leu Ser Cys Ala Ala Ser Gly Phe Thr Phe
                245                 250                 255 gac gac tac gcc atg cac tgg gtc cga cag gcc cct ggc aag ggc ctg     816
Asp Asp Tyr Ala Met His Trp Val Arg Gln Ala Pro Gly Lys Gly Leu
            260                 265                 270 gaa tgg gtg gcc ggc atc tcc tgg aac tcc ggc tcc atc gtg tac gcc     864
Glu Trp Val Ala Gly Ile Ser Trp Asn Ser Gly Ser Ile Val Tyr Ala
        275                 280                 285 gac tcc gtg aag ggc cgg ttc acc atc tcc cgg gac aac tcc aag aac     912
Asp Ser Val Lys Gly Arg Phe Thr Ile Ser Arg Asp Asn Ser Lys Asn
    290                 295                 300 acc ctg tac ctg cag atg aac tcc ctg cgg gcc gag gac acc gcc gtg     960
```

```
Thr Leu Tyr Leu Gln Met Asn Ser Leu Arg Ala Glu Asp Thr Ala Val
305                 310                 315                 320 tac tac tgc gcc aag gac atc aga gag cag ctg gtc gag gac gcc ttc      1008
Tyr Tyr Cys Ala Lys Asp Ile Arg Glu Gln Leu Val Glu Asp Ala Phe
                325                 330                 335 gac atc tgg ggc cag ggc acc ctg gtc acc gtg tcc tca gcc agc acc      1056
Asp Ile Trp Gly Gln Gly Thr Leu Val Thr Val Ser Ser Ala Ser Thr
            340                 345                 350 aag ggg ccc tct gtg ttt ccc ctt gcc cct tgc agt agg tct acc agc      1104
Lys Gly Pro Ser Val Phe Pro Leu Ala Pro Cys Ser Arg Ser Thr Ser
        355                 360                 365 gaa agt act gcc gcc ctt ggc tgt ctg gtg aaa gat tat ttt cct gaa      1152
Glu Ser Thr Ala Ala Leu Gly Cys Leu Val Lys Asp Tyr Phe Pro Glu
    370                 375                 380 cct gtc acc gtg tcc tgg aac tcc ggt gct ttg act tct ggc gtt cat      1200
Pro Val Thr Val Ser Trp Asn Ser Gly Ala Leu Thr Ser Gly Val His
385                 390                 395                 400 act ttt cct gca gtc ctg caa agt tct ggc ctg tac agc ctt agc tcc      1248
Thr Phe Pro Ala Val Leu Gln Ser Ser Gly Leu Tyr Ser Leu Ser Ser
                405                 410                 415 gtg gta act gtg cct tcc tct tct ctg ggt acc aaa acc tat acc tgc      1296
Val Val Thr Val Pro Ser Ser Ser Leu Gly Thr Lys Thr Tyr Thr Cys
            420                 425                 430 aat gtg gac cac aaa cct tct aat act aag gtc gac aag agg gtg gag      1344
Asn Val Asp His Lys Pro Ser Asn Thr Lys Val Asp Lys Arg Val Glu
        435                 440                 445 tct aag tac gga cca cct tgt cct cca tgc ccc gcc ccc gag ttc gag      1392
Ser Lys Tyr Gly Pro Pro Cys Pro Pro Cys Pro Ala Pro Glu Phe Glu
    450                 455                 460 ggc ggt cct agt gtg ttc ctg ttc cct cca aag ccc aag gac acc ttg      1440
Gly Gly Pro Ser Val Phe Leu Phe Pro Pro Lys Pro Lys Asp Thr Leu
465                 470                 475                 480 atg ata agc agg act cct gag gtg aca tgt gtg gtt gta gac gtc tct      1488
Met Ile Ser Arg Thr Pro Glu Val Thr Cys Val Val Val Asp Val Ser
                485                 490                 495 cag gag gat ccc gaa gtg cag ttt aat tgg tac gtg gat gga gtc gag      1536
Gln Glu Asp Pro Glu Val Gln Phe Asn Trp Tyr Val Asp Gly Val Glu
            500                 505                 510 gtg cac aac gcc aaa acc aaa ccc cgc gag gag caa ttc aac tcc acc      1584
Val His Asn Ala Lys Thr Lys Pro Arg Glu Glu Gln Phe Asn Ser Thr
        515                 520                 525 tat cgc gtg gtg tct gtc ctg acc gtc ctg cac caa gat tgg ctg aac      1632
Tyr Arg Val Val Ser Val Leu Thr Val Leu His Gln Asp Trp Leu Asn
    530                 535                 540 gga aaa gaa tat aag tgt aaa gta agc aat aag ggc ctg cct tca tcc      1680
Gly Lys Glu Tyr Lys Cys Lys Val Ser Asn Lys Gly Leu Pro Ser Ser
545                 550                 555                 560 att gag aag aca atc agc aag gca aag ggc cag cct aga gaa ccc caa      1728
Ile Glu Lys Thr Ile Ser Lys Ala Lys Gly Gln Pro Arg Glu Pro Gln
                565                 570                 575 gtg tac acc ctc cca ccc tct cag gag gaa atg acc aag aat cag gtt      1776
Val Tyr Thr Leu Pro Pro Ser Gln Glu Glu Met Thr Lys Asn Gln Val
            580                 585                 590 agc ctt act tgt ctc gta aag ggg ttc tac cct agc gac att gct gtc      1824
Ser Leu Thr Cys Leu Val Lys Gly Phe Tyr Pro Ser Asp Ile Ala Val
        595                 600                 605 gag tgg gaa agc aat gga cag cct gag aat aac tat aaa acc act ccc      1872
Glu Trp Glu Ser Asn Gly Gln Pro Glu Asn Asn Tyr Lys Thr Thr Pro
    610                 615                 620
```

```
cca gtg ctt gac tca gat ggc tct ttt ttc ctt tac tcc cgc ttg aca      1920
Pro Val Leu Asp Ser Asp Gly Ser Phe Phe Leu Tyr Ser Arg Leu Thr
625                 630                 635                 640 gtc gac aag agt aga tgg caa gag ggg aac gtg ttc agc tgc agt gtt      1968
Val Asp Lys Ser Arg Trp Gln Glu Gly Asn Val Phe Ser Cys Ser Val
                645                 650                 655 atg cac gag gca ctc cat aac cat tat act cag aaa tcc ttg agc ctg      2016
Met His Glu Ala Leu His Asn His Tyr Thr Gln Lys Ser Leu Ser Leu
            660                 665                 670 tcc ctt gga aag                                                      2028
Ser Leu Gly Lys
        675
```

<210> SEQ ID NO 10
<211> LENGTH: 676
<212> TYPE: PRT
<213> ORGANISM: Artificial Sequence
<220> FEATURE:
<223> OTHER INFORMATION: Synthetic Construct

<400> SEQUENCE: 10

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ala Gly Ile Ser Trp Asn Ser Gly Ser Ile Val Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Ile Arg Glu Gln Leu Val Glu Asp Ala Phe Asp Ile Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Lys Val Glu Pro Lys Ser
    210                 215                 220

Cys Gly Ser Glu Val Gln Leu Val Glu Ser Gly Gly Gly Leu Val Gln
225                 230                 235                 240

Pro Gly Gly Ser Leu Arg Leu Ser Cys Ala Ala Ser Gly Phe Thr Phe
                245                 250                 255

Asp Asp Tyr Ala Met His Trp Val Arg Gln Ala Pro Gly Lys Gly Leu
            260                 265                 270

Glu Trp Val Ala Gly Ile Ser Trp Asn Ser Gly Ser Ile Val Tyr Ala
        275                 280                 285
```

```
Asp Ser Val Lys Gly Arg Phe Thr Ile Ser Arg Asp Asn Ser Lys Asn
            290                 295                 300

Thr Leu Tyr Leu Gln Met Asn Ser Leu Arg Ala Glu Asp Thr Ala Val
305                 310                 315                 320

Tyr Tyr Cys Ala Lys Asp Ile Arg Glu Gln Leu Val Glu Asp Ala Phe
                325                 330                 335

Asp Ile Trp Gly Gln Gly Thr Leu Val Thr Val Ser Ser Ala Ser Thr
            340                 345                 350

Lys Gly Pro Ser Val Phe Pro Leu Ala Pro Cys Ser Arg Ser Thr Ser
                355                 360                 365

Glu Ser Thr Ala Ala Leu Gly Cys Leu Val Lys Asp Tyr Phe Pro Glu
370                 375                 380

Pro Val Thr Val Ser Trp Asn Ser Gly Ala Leu Thr Ser Gly Val His
385                 390                 395                 400

Thr Phe Pro Ala Val Leu Gln Ser Ser Gly Leu Tyr Ser Leu Ser Ser
                405                 410                 415

Val Val Thr Val Pro Ser Ser Ser Leu Gly Thr Lys Thr Tyr Thr Cys
                420                 425                 430

Asn Val Asp His Lys Pro Ser Asn Thr Lys Val Asp Lys Arg Val Glu
            435                 440                 445

Ser Lys Tyr Gly Pro Pro Cys Pro Pro Cys Pro Ala Pro Glu Phe Glu
450                 455                 460

Gly Gly Pro Ser Val Phe Leu Phe Pro Pro Lys Pro Lys Asp Thr Leu
465                 470                 475                 480

Met Ile Ser Arg Thr Pro Glu Val Thr Cys Val Val Val Asp Val Ser
                485                 490                 495

Gln Glu Asp Pro Glu Val Gln Phe Asn Trp Tyr Val Asp Gly Val Glu
            500                 505                 510

Val His Asn Ala Lys Thr Lys Pro Arg Glu Glu Gln Phe Asn Ser Thr
        515                 520                 525

Tyr Arg Val Val Ser Val Leu Thr Val Leu His Gln Asp Trp Leu Asn
            530                 535                 540

Gly Lys Glu Tyr Lys Cys Lys Val Ser Asn Lys Gly Leu Pro Ser Ser
545                 550                 555                 560

Ile Glu Lys Thr Ile Ser Lys Ala Lys Gly Gln Pro Arg Glu Pro Gln
                565                 570                 575

Val Tyr Thr Leu Pro Pro Ser Gln Glu Glu Met Thr Lys Asn Gln Val
            580                 585                 590

Ser Leu Thr Cys Leu Val Lys Gly Phe Tyr Pro Ser Asp Ile Ala Val
                595                 600                 605

Glu Trp Glu Ser Asn Gly Gln Pro Glu Asn Asn Tyr Lys Thr Thr Pro
            610                 615                 620

Pro Val Leu Asp Ser Asp Gly Ser Phe Phe Leu Tyr Ser Arg Leu Thr
625                 630                 635                 640

Val Asp Lys Ser Arg Trp Gln Glu Gly Asn Val Phe Ser Cys Ser Val
                645                 650                 655

Met His Glu Ala Leu His Asn His Tyr Thr Gln Lys Ser Leu Ser Leu
            660                 665                 670

Ser Leu Gly Lys
            675

<210> SEQ ID NO 11
<211> LENGTH: 1356
```

```
<212> TYPE: DNA
<213> ORGANISM: Artificial Sequence
<220> FEATURE:
<223> OTHER INFORMATION: H-chain of anti-human Tie2 antibody
<220> FEATURE:
<221> NAME/KEY: CDS
<222> LOCATION: (1)..(1356)

<400> SEQUENCE: 11 gag gtg cag ctg gtg gaa tcc gga gga ggc ctg gtg cag cct ggc ggc      48
Glu Val Gln Leu Val Glu Ser Gly Gly Gly Leu Val Gln Pro Gly Gly
1               5                   10                  15 tct ctg aga ctg tcc tgt gcc gcc tcc ggc ttc acc ttc gac gac tac      96
Ser Leu Arg Leu Ser Cys Ala Ala Ser Gly Phe Thr Phe Asp Asp Tyr
            20                  25                  30 gcc atg cac tgg gtc cga cag gcc cct ggc aag ggc ctg gaa tgg gtg     144
Ala Met His Trp Val Arg Gln Ala Pro Gly Lys Gly Leu Glu Trp Val
        35                  40                  45 gcc ggc atc tcc tgg aac tcc ggc tcc atc gtg tac gcc gac tcc gtg     192
Ala Gly Ile Ser Trp Asn Ser Gly Ser Ile Val Tyr Ala Asp Ser Val
    50                  55                  60 aag ggc cgg ttc acc atc tcc cgg gac aac tcc aag aac acc ctg tac     240
Lys Gly Arg Phe Thr Ile Ser Arg Asp Asn Ser Lys Asn Thr Leu Tyr
65                  70                  75                  80 ctg cag atg aac tcc ctg cgg gcc gag gac acc gcc gtg tac tac tgc     288
Leu Gln Met Asn Ser Leu Arg Ala Glu Asp Thr Ala Val Tyr Tyr Cys
                85                  90                  95 gcc aag gac atc aga gag cag ctg gtc gag gac gcc ttc gac atc tgg     336
Ala Lys Asp Ile Arg Glu Gln Leu Val Glu Asp Ala Phe Asp Ile Trp
            100                 105                 110 ggc cag ggc acc ctg gtc acc gtg tcc tca gcc tcc acc aag ggc cca     384
Gly Gln Gly Thr Leu Val Thr Val Ser Ser Ala Ser Thr Lys Gly Pro
        115                 120                 125 tcg gtc ttc ccc ctg gca ccc tcc tcc aag agc acc tct ggg ggc aca     432
Ser Val Phe Pro Leu Ala Pro Ser Ser Lys Ser Thr Ser Gly Gly Thr
    130                 135                 140 gcg gcc ctg ggc tgc ctg gtc aag gac tac ttc ccc gaa ccg gtg acg     480
Ala Ala Leu Gly Cys Leu Val Lys Asp Tyr Phe Pro Glu Pro Val Thr
145                 150                 155                 160 gtg tcg tgg aac tca ggc gcc ctg acc agc ggc gtg cac acc ttc ccg     528
Val Ser Trp Asn Ser Gly Ala Leu Thr Ser Gly Val His Thr Phe Pro
                165                 170                 175 gct gtc cta cag tcc tca gga ctc tac tcc ctt agt agc gtg gtg acc     576
Ala Val Leu Gln Ser Ser Gly Leu Tyr Ser Leu Ser Ser Val Val Thr
            180                 185                 190 gtg ccc tcc agc agc ttg ggc acc cag acc tac atc tgc aac gtg aat     624
Val Pro Ser Ser Ser Leu Gly Thr Gln Thr Tyr Ile Cys Asn Val Asn
        195                 200                 205 cac aag ccc agc aac acc aag gtg gac aag aaa gtt gag ccc aaa tct     672
His Lys Pro Ser Asn Thr Lys Val Asp Lys Lys Val Glu Pro Lys Ser
    210                 215                 220 tgt gac aaa act cac aca tgc cca ccg tgc cca gca cct gaa ctc ctg     720
Cys Asp Lys Thr His Thr Cys Pro Pro Cys Pro Ala Pro Glu Leu Leu
225                 230                 235                 240 ggg gga ccg tca gtc ttc ctc ttc ccc cca aaa ccc aag gac acc ctc     768
Gly Gly Pro Ser Val Phe Leu Phe Pro Pro Lys Pro Lys Asp Thr Leu
                245                 250                 255 atg atc tcc cgg acc cct gag gtc aca tgc gtg gtg gtg gac gtg agc     816
Met Ile Ser Arg Thr Pro Glu Val Thr Cys Val Val Val Asp Val Ser
            260                 265                 270 cac gaa gac cct gag gtc aag ttc aac tgg tac gtg gac ggc gtg gag     864
```

```
His Glu Asp Pro Glu Val Lys Phe Asn Trp Tyr Val Asp Gly Val Glu
        275                 280                 285 gtg cat aat gcc aag aca aag ccg cgg gag gag cag tac aac agc acg    912
Val His Asn Ala Lys Thr Lys Pro Arg Glu Glu Gln Tyr Asn Ser Thr
290                 295                 300 tac cgt gtg gtc agc gtc ctc acc gtc ctg cac cag gac tgg ctg aat    960
Tyr Arg Val Val Ser Val Leu Thr Val Leu His Gln Asp Trp Leu Asn
305                 310                 315                 320 ggc aag gag tac aag tgc aag gtc tcc aac aaa gcc ctc cca gcc ccc   1008
Gly Lys Glu Tyr Lys Cys Lys Val Ser Asn Lys Ala Leu Pro Ala Pro
            325                 330                 335 atc gag aaa acc atc tcc aaa gcc aaa ggg cag ccc cga gaa cca cag   1056
Ile Glu Lys Thr Ile Ser Lys Ala Lys Gly Gln Pro Arg Glu Pro Gln
        340                 345                 350 gtg tac acc ctg ccc cca tcc cgg gat gag ctg acc aag aac cag gtc   1104
Val Tyr Thr Leu Pro Pro Ser Arg Asp Glu Leu Thr Lys Asn Gln Val
            355                 360                 365 agc ctg acc tgc ctg gtc aaa ggc ttc tat ccc agc gac atc gcc gtg   1152
Ser Leu Thr Cys Leu Val Lys Gly Phe Tyr Pro Ser Asp Ile Ala Val
370                 375                 380 gag tgg gag agc aat ggg cag ccg gag aac aac tac aag acc acg cct   1200
Glu Trp Glu Ser Asn Gly Gln Pro Glu Asn Asn Tyr Lys Thr Thr Pro
385                 390                 395                 400 ccc gtg ctg gac tcc gac ggc tcc ttc ttc ctc tac agc aag ctc acc   1248
Pro Val Leu Asp Ser Asp Gly Ser Phe Phe Leu Tyr Ser Lys Leu Thr
            405                 410                 415 gtg gac aag agc agg tgg cag cag ggg aac gtc ttc tca tgc tcc gtg   1296
Val Asp Lys Ser Arg Trp Gln Gln Gly Asn Val Phe Ser Cys Ser Val
        420                 425                 430 atg cat gag gct ctg cac aac cac tac acg cag aag agc ctc tcc ctg   1344
Met His Glu Ala Leu His Asn His Tyr Thr Gln Lys Ser Leu Ser Leu
            435                 440                 445 tct ccg ggt aaa                                                    1356
Ser Pro Gly Lys
        450

<210> SEQ ID NO 12
<211> LENGTH: 452
<212> TYPE: PRT
<213> ORGANISM: Artificial Sequence
<220> FEATURE:
<223> OTHER INFORMATION: Synthetic Construct

<400> SEQUENCE: 12

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ala Gly Ile Ser Trp Asn Ser Gly Ser Ile Val Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Ile Arg Glu Gln Leu Val Glu Asp Ala Phe Asp Ile Trp
            100                 105                 110

Gly Gln Gly Thr Leu Val Thr Val Ser Ser Ala Ser Thr Lys Gly Pro
```

```
                115                 120                 125
Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Lys Val Glu Pro Lys Ser
    210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Asp Glu Leu Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly Lys
    450

<210> SEQ ID NO 13
<211> LENGTH: 7
<212> TYPE: PRT
<213> ORGANISM: Artificial Sequence
<220> FEATURE:
<223> OTHER INFORMATION: linker

<400> SEQUENCE: 13

Glu Pro Lys Ser Cys Gly Ser
1               5
```

-continued

```
<210> SEQ ID NO 14
<211> LENGTH: 14
<212> TYPE: PRT
<213> ORGANISM: Artificial Sequence
<220> FEATURE:
<223> OTHER INFORMATION: linker

<400> SEQUENCE: 14

Glu Leu Lys Thr Pro Leu Gly Asp Thr Thr His Thr Gly Ser
1               5                   10

<210> SEQ ID NO 15
<211> LENGTH: 22
<212> TYPE: PRT
<213> ORGANISM: Artificial Sequence
<220> FEATURE:
<223> OTHER INFORMATION: linker

<400> SEQUENCE: 15

Glu Leu Lys Thr Pro Leu Gly Asp Thr Thr His Thr Gly Gly Gly Gly
1               5                   10                  15

Ser Gly Gly Gly Gly Ser
            20

<210> SEQ ID NO 16
<211> LENGTH: 32
<212> TYPE: PRT
<213> ORGANISM: Artificial Sequence
<220> FEATURE:
<223> OTHER INFORMATION: linker

<400> SEQUENCE: 16

Glu Leu Lys Thr Pro Leu Gly Asp Thr Thr His Thr Gly Gly Gly Gly
1               5                   10                  15

Ser Gly Gly Gly Gly Ser Gly Gly Gly Gly Ser Gly Gly Gly Gly Ser
            20                  25                  30

<210> SEQ ID NO 17
<211> LENGTH: 42
<212> TYPE: PRT
<213> ORGANISM: Artificial Sequence
<220> FEATURE:
<223> OTHER INFORMATION: linker

<400> SEQUENCE: 17

Glu Leu Lys Thr Pro Leu Gly Asp Thr Thr His Thr Gly Gly Gly Gly
1               5                   10                  15

Ser Gly Gly Gly Gly Ser Gly Gly Gly Gly Ser Gly Gly Gly Gly Ser
            20                  25                  30

Gly Gly Gly Gly Ser Gly Gly Gly Gly Ser
        35                  40

<210> SEQ ID NO 18
<211> LENGTH: 52
<212> TYPE: PRT
<213> ORGANISM: Artificial Sequence
<220> FEATURE:
<223> OTHER INFORMATION: linker

<400> SEQUENCE: 18

Glu Leu Lys Thr Pro Leu Gly Asp Thr Thr His Thr Gly Gly Gly Gly
1               5                   10                  15

Ser Gly Gly Gly Gly Ser Gly Gly Gly Gly Ser Gly Gly Gly Gly Ser
            20                  25                  30
```

Gly Gly Gly Gly Ser Gly Gly Gly Ser Gly Gly Gly Ser Gly
            35                  40                  45

Gly Gly Gly Ser
    50

<210> SEQ ID NO 19
<211> LENGTH: 62
<212> TYPE: PRT
<213> ORGANISM: Artificial Sequence
<220> FEATURE:
<223> OTHER INFORMATION: linker

<400> SEQUENCE: 19

Glu Leu Lys Thr Pro Leu Gly Asp Thr Thr His Thr Gly Gly Gly
1               5                   10                  15

Ser Gly Gly Gly Ser Gly Gly Gly Ser Gly Gly Gly Ser
            20                  25                  30

Gly Gly Gly Ser Gly Gly Gly Ser Gly Gly Gly Ser Gly
            35                  40                  45

Gly Gly Ser Gly Gly Gly Ser Gly Gly Gly Ser
    50                  55                  60

<210> SEQ ID NO 20
<211> LENGTH: 64
<212> TYPE: PRT
<213> ORGANISM: Artificial Sequence
<220> FEATURE:
<223> OTHER INFORMATION: linker

<400> SEQUENCE: 20

Glu Leu Lys Thr Pro Leu Gly Asp Thr Thr His Thr Ser Pro Arg Ser
1               5                   10                  15

Pro Glu Pro Lys Ser Ser Asp Thr Pro Pro Ser Pro Arg Ser Pro
            20                  25                  30

Glu Pro Lys Ser Ser Asp Thr Pro Pro Ser Pro Arg Ser Pro Glu
            35                  40                  45

Pro Lys Ser Ser Asp Thr Pro Pro Ser Pro Arg Ser Pro Gly Ser
    50                  55                  60

<210> SEQ ID NO 21
<211> LENGTH: 3369
<212> TYPE: DNA
<213> ORGANISM: Homo sapiens

<400> SEQUENCE: 21
atggactctt tagccagctt agttctctgt ggagtcagct tgctcctttc tggaactgtg      60
gaaggtgcca tggacttgat cttgatcaat tccctacctc ttgtatctga tgctgaaaca     120
tctctcacct gcattgcctc tgggtggcgc ccccatgagc ccatcaccat aggaagggac     180
tttgaagcct taatgaacca gcaccaggat ccgctggaag ttactcaaga tgtgaccaga     240
gaatgggcta aaaagttgtt ttggaagaga gaaaaggcta gtaagatcaa tggtgcttat     300
ttctgtgaag gcgagttcg aggagaggca atcaggatac gaaccatgaa gatgcgtcaa     360
caagcttcct cctaccagc tactttaact atgactgtgg acaagggaga taacgtgaac     420
atatctttca aaaggtatt gactaaagaa gaagatgcag tgatttacaa aaatggttcc     480
ttcatccatt cagtgccccg gcatgaagta cctgatattc tagaagtaca cctgcctcat     540
gctcagcccc aggatgctgg agtgtactcg gccaggtata taggaggaaa cctcttcacc     600
tcggccttca ccaggctgat agtccggaga tgtgaagccc agaagtgggg acctgaatgc     660

```
aaccatctct gtactgcttg tatgaacaat ggtgtctgcc atgaagatac tggagaatgc    720
atttgccctc ctgggtttat gggaaggacg tgtgagaagg cttgtgaact gcacacgttt    780
ggcagaactt gtaaagaaag gtgcagtgga caagagggat gcaagtctta tgtgttctgt    840
ctccctgacc cctatgggtg ttcctgtgcc acaggctgga agggtctgca gtgcaatgaa    900
gcatgccacc ctggttttta cgggccagat tgtaagctta ggtgcagctg caacaatggg    960
gagatgtgtg atcgcttcca aggatgtctc tgctctccag gatggcaggg gctccagtgt   1020
gagagagaag gcataccgag gatgaccccca agatagtgg atttgccaga tcatatagaa   1080
```

```
gtgcgctgga tggccatcga gtcactgaat tacagtgtgt acacaaccaa cagtgatgta    3060
tggtcctatg gtgtgttact atgggagatt gttagcttag gaggcacacc ctactgcgga    3120
atgacttgtg cagaactcta cgagaagctg ccccagggct acagactgga gaagcccctg    3180
aactgtgatg atgaggtgta tgatctaatg agacaatgct ggcgggagaa gccttatgag    3240
aggccatcat ttgcccagat attggtgtcc ttaaacagaa tgttagagga gcgaaagacc    3300
tacgtgaata ccacgcttta tgagaagttt acttatgcag gaattgactg ttctgctgaa    3360
gaagcggcc                                                            3369
```

<210> SEQ ID NO 22
<211> LENGTH: 6
<212> TYPE: PRT
<213> ORGANISM: Artificial Sequence
<220> FEATURE:
<223> OTHER INFORMATION: thrombin cleavage site

<400> SEQUENCE: 22

Leu Val Pro Arg Gly Ser
1               5

<210> SEQ ID NO 23
<211> LENGTH: 231
<212> TYPE: PRT
<213> ORGANISM: Homo sapiens

<400> SEQUENCE: 23

Pro Lys Ser Cys Asp Lys Thr His Thr Cys Pro Pro Cys Pro Ala Pro
1               5                   10                  15

Glu Leu Leu Gly Gly Pro Ser Val Phe Leu Phe Pro Pro Lys Pro Lys
                20                  25                  30

Asp Thr Leu Met Ile Ser Arg Thr Pro Glu Val Thr Cys Val Val Val
            35                  40                  45

Asp Val Ser His Glu Asp Pro Glu Val Lys Phe Asn Trp Tyr Val Asp
        50                  55                  60

Gly Val Glu Val His Asn Ala Lys Thr Lys Pro Arg Glu Glu Gln Tyr
65                  70                  75                  80

Asn Ser Thr Tyr Arg Val Val Ser Val Leu Thr Val Leu His Gln Asp
                85                  90                  95

Trp Leu Asn Gly Lys Glu Tyr Lys Cys Lys Val Ser Asn Lys Ala Leu
            100                 105                 110

Pro Ala Pro Ile Glu Lys Thr Ile Ser Lys Ala Lys Gly Gln Pro Arg
        115                 120                 125

Glu Pro Gln Val Tyr Thr Leu Pro Pro Ser Arg Asp Glu Leu Thr Lys
    130                 135                 140

Asn Gln Val Ser Leu Thr Cys Leu Val Lys Gly Phe Tyr Pro Ser Asp
145                 150                 155                 160

Ile Ala Val Glu Trp Glu Ser Asn Gly Gln Pro Glu Asn Asn Tyr Lys
                165                 170                 175

Thr Thr Pro Pro Val Leu Asp Ser Asp Gly Ser Phe Phe Leu Tyr Ser
            180                 185                 190

Lys Leu Thr Val Asp Lys Ser Arg Trp Gln Gln Gly Asn Val Phe Ser
        195                 200                 205

```
Cys Ser Val Met His Glu Ala Leu His Asn His Tyr Thr Gln Lys Ser
    210                 215                 220

Leu Ser Leu Ser Pro Gly Lys
225                 230
```

ANTI-HUMAN TIE-2 ANTIBODY

CROSS-REFERENCE TO RELATED APPLICATIONS

This application is a Divisional of U.S. application Ser. No. 15/134,803, filed Apr. 21, 2016, which is a Continuation Application of PCT/JP2015/070089, filed Jul. 14, 2015, which claims priority from Japanese application JP 2014-145135, filed Jul. 15, 2014, the entire contents of which are incorporated herein by reference.

The instant application contains a Sequence Listing which has been submitted in ASCII format via EFS-WEB and is hereby incorporated by reference in its entirety. Said ASCII copy, created on Apr. 28, 2017, is named sequence.txt and is 89 KB.

TECHNICAL FIELD

The present invention relates to a novel anti-human Tie-2 antibody.

BACKGROUND ART

A tyrosine kinase with Ig and EGF homology domains 2 (Tie2) is a receptor type tyrosine kinase. Tie2 is mainly known to be expressed in vascular endothelial cells. As the ligand, Angiopoietin-1 (Ang-1) and Angiopoietin-2 (Ang-2), which are multimer type secreted glycoproteins, are known.

Ang-1 functions as an agonist for Tie2. It has been found that when Tie2 binds to Ang-1, it is autophosphorylated by forming a multimer and transmits a signal into a cell, thereby promoting an anti-apoptotic action of vascular endothelial cells, vascular stabilization via a permeation inhibitory action of blood vessels, maturation and remodeling (Cell, 1996, Vol. 87, pp. 1171-1180; Genes Dev., 1994, Vol. 8, pp. 1897-1909; Science, 1999, Vol. 286, pp. 2511-2514; and Nat. Struct. Biol., 2003, Vol. 10, pp. 38-44). Further, it has also been known that Ang-1 exerts vasodilating and blood flow-enhancing actions by the production of nitric oxide through Tie2 activation (Pharmacol. Res., 2014, Vol. 80, pp. 43-51). In addition, it is believed that Ang-1 contributes to the stabilization of blood vessels by inhibiting the internalization of vascular endothelial cadherin through Tie2 activation (Dev. Cell, 2008, Vol. 14, pp. 25-36). On the other hand, it is believed that Ang-2 is capable of activating Tie2 on vascular endothelial cells, but its activation is believed to be partial, as compared to Ang-1 (Mol. Cell Biol., 2009, Vol. 29, pp. 2011-2022). Ang-2 binds to the same site of Tie2 with substantially the same affinity as Ang-1, and as a result, it has been suggested that Ang-2 functions as an endogenous Tie2 antagonist from the viewpoint that the activation of Tie2 by Ang-1 is replaced by partial activation of Ang-2 (Science, 1997, Vol. 277, pp. 55-60).

An increase in the concentration of Ang-2 in the blood has been reported in a disease induced by vascular vulnerability which is considered to be one of the causes of the disease, such as diabetes, diabetic retinopathy, sepsis, and acute renal failure (Atherosclerosis, 2005, Vol. 180, pp. 113-118; Br. J. Ophthalmol., 2004, Vol. 88, pp. 1543-1546; Critical Care, 2009, Vol. 13, p. 207; and Intensive Care Med., 2010, Vol. 36, pp. 462-470).

Regarding relevance to diabetic retinopathy and diabetic macular edema, it has been reported that the concentration of Ang-2 in the blood plasma or the vitreous humor of patients has risen (Br. J. Ophthalmol., 2004, Vol. 88, pp. 1543-1546; and Br. J. Ophthalmol., 2005, Vol. 89, pp. 480-483). Further, in the retinal blood vessel of patients with diabetic retinopathy, the loss of pericytes which are the main Ang-1 producing cells (Cell, 1996, Vol. 87, pp. 1161-1169) has also been known to be one of the characteristic lesions (Retina, 2013, Fifth edition, pp. 925-939). Diabetic macular edema is known for involving the thickening of the macular area as one of the conditions thereof, but it has also been reported that in patients with an increase in the intraocular Ang-1 concentration due to vitreous removal surgery, the thickening of the macular area is decreased (Br. J. Ophthalmol., 2005, Vol. 89, pp. 480-483). Further, from the viewpoints that in retinal edema mouse models with the loss of pericytes in the retinal blood vessels, retinal edema and retinal bleeding are observed, and the pathology onset is inhibited by the intravitreal administration of Ang-1 (J. Clin. Invest., 2002, Vol. 110, pp. 1619-1628), and that in a test using a mouse model with diabetic retinopathy, vascular endothelial cell disorders in the retina are inhibited by the administration of an adenovirus containing a gene encoding Ang-1 (Am. J. Pathol., 2002, Vol. 160, pp. 1683-1693), it has been suggested that Ang-1 has an action of improving the conditions. Meanwhile, it has been reported that in genetically modified mice having Ang-2 specifically over-expressed in the retina, retinal cell damage is increased (Acta. Diabetol. 2010, Vol. 47, pp. 59-64).

It has been reported that with regard to critical limb ischemia, the amount of Ang-2 in the blood plasma increases in patients with peripheral arterial diseases, and the amount of Ang-2 expressed in the ischemic limb muscles or the skin tissues in patients with critical limb ischemia is high (J. Am. Coll. Cardial., 2008, Vol. 52, pp. 387-393; and Int. Angiol., 2011, Vol. 30, pp. 25-34). Moreover, in a test using a rat model with hindlimb ischemia, blood flow recovery and anti-apoptotic effect in the ischemic limb is promoted by the administration of a viral vector containing a gene encoding Ang-1 (Angiogenesis, 2009, Vol. 12, pp. 243-249). From the viewpoint that it has been reported that mature blood vessels covered by the smooth muscle cells are increased in the border zone of infarcted area by the administration of a virus containing a gene encoding Ang-1 in a coronary artery ligation model of a db/db mouse as an animal model with type 2 diabetes (Diabetes, 2008, Vol. 57, pp. 3335-3343), an effect of promoting the maturation of unstable neovascular vessels can be expected by the activation of Tie2 signals.

As an antibody showing an agonistic action on a human Tie2, a murine monoclonal antibody 15B8 (Patent Document 1) has been reported. It has been reported that 15B8 binds to the human Tie2 to induce an anti-apoptotic action in a human vascular endothelial cell HUVEC (Patent Document 1)

RELATED ART

Patent Document

[Patent Document 1] WO 2000/018804

DISCLOSURE OF INVENTION

Problems to be Solved by the Invention

An object of the present invention is to provide an anti-human Tie2 antibody for preventing or treating diabetic macular edema, diabetic retinopathy, or critical limb ischemia by binding to a human Tie2 to activate the human Tie2.

Means for Solving the Problems

The present inventors have repeatedly conducted substantial and inventive studies in preparation of an anti-human Tie2 antibody, and as a result, they have found that a tetravalent anti-human Tie2 antibody comprising a heavy chain variable region consisting of the amino acid sequence of the amino acid numbers 1 to 122 of SEQ ID NO: 2 and a light chain variable region consisting of the amino acid sequence of the amino acid numbers 1 to 113 of SEQ ID NO: 4 is prepared (Examples 1 to 8), and thus, the anti-human Tie2 antibody binds to the human Tie2 (Example 12), induces the anti-apoptotic action in a human Tie2-expressing BaF3 cell (Examples 9 and 11), and inhibits the vascular hyperpermeability in a rat model with vascular hyperpermeability (Examples 10 and 13). As a result, they have provided such an anti-human Tie2 antibody, thereby completing the present invention.

That is, the present invention may include the following invention as a material or a method which is medically or industrially applicable.

[1] An anti-human Tie2 antibody or an antigen-binding fragment thereof, comprising four heavy chain variable regions and four light chain variable regions, wherein the heavy chain variable region comprises CDR1 consisting of the amino acid sequence of the amino acid numbers 31 to 35 of SEQ ID NO: 2, CDR2 consisting of the amino acid sequence of the amino acid numbers 50 to 66 of SEQ ID NO: 2, and CDR3 consisting of the amino acid sequence of the amino acid numbers 99 to 111 of SEQ ID NO: 2;

the light chain variable region comprises CDR1 consisting of the amino acid sequence of the amino acid numbers 24 to 39 of SEQ ID NO: 4, CDR2 consisting of the amino acid sequence of the amino acid numbers 55 to 61 of SEQ ID NO: 4, and CDR3 consisting of the amino acid sequence of the amino acid numbers 94 to 102 of SEQ ID NO: 4; and the one heavy chain variable region and the one light chain variable region constitute one antigen-binding site, and the antibody or the antigen-binding fragment thereof comprises four antigen-binding sites.

[2] The anti-human Tie2 antibody or the antigen-binding fragment thereof of [1], selected from (1) or (2) below:

(1) an anti-human Tie2 antibody or an antigen-binding fragment thereof, comprising four heavy chain variable regions and four light chain variable regions, in which the heavy chain variable region consists of the amino acid sequence of the amino acid numbers 1 to 122 of SEQ ID NO: 2, the light chain variable region consists of the amino acid sequence of the amino acid numbers 1 to 113 of SEQ ID NO: 4, and the one heavy chain variable region and the one light chain variable region constitute one antigen-binding site, and the antibody or the antigen-binding fragment thereof comprises four antigen-binding sites; and (2) an anti-human Tie2 antibody or an antigen-binding fragment thereof which is an antibody or an antigen-binding fragment thereof derived from posttranslational modification of the anti-human Tie2 antibody or the antigen-binding fragment thereof of (1).

[3] The anti-human Tie2 antibody of [1], wherein the antibody comprises two heavy chains and four light chains;

each heavy chain comprises two structures consisting of a heavy chain variable region comprising CDR1 consisting of the amino acid sequence of the amino acid numbers 31 to 35 of SEQ ID NO: 2, CDR2 consisting of the amino acid sequence of the amino acid numbers 50 to 66 of SEQ ID NO: 2, and CDR3 consisting of the amino acid sequence of the amino acid numbers 99 to 111 of SEQ ID NO: 2 and a CH1 region, a CH2 region, and a CH3 region, and the carboxy terminus (C terminus) of one of the structures is linked to the amino terminus (N terminus) of the other structure through a linker; and each light chain comprises a light chain variable region comprising CDR1 consisting of the amino acid sequence of the amino acid numbers 24 to 39 of SEQ ID NO: 4, CDR2 consisting of the amino acid sequence of the amino acid numbers 55 to 61 of SEQ ID NO: 4, and CDR3 consisting of the amino acid sequence of the amino acid numbers 94 to 102 of SEQ ID NO: 4, and a light chain constant region.

[4] The anti-human Tie2 antibody of [3], selected from (1) or (2) below:

(1) an anti-human Tie2 antibody comprising two heavy chains and four light chains, in which each heavy chain comprises two structures consisting of a heavy chain variable region consisting of the amino acid sequence of the amino acid numbers 1 to 122 of SEQ ID NO: 2 and a CH1 region, a CH2 region, and a CH3 region, and the C terminus of one of the structures is linked to the N terminus of the other structure through a linker; and each light chain comprises a light chain variable region consisting of the amino acid sequence of the amino acid numbers 1 to 113 of SEQ ID NO: 4, and a light chain constant region; and (2) an anti-human Tie2 antibody, which is an antibody derived from posttranslational modification of the anti-human Tie2 antibody of (1).

[5] The anti-human Tie2 antibody of [4], wherein the anti-human Tie2 antibody comprises two heavy chains and four light chains;

each heavy chain comprises two structures consisting of a heavy chain variable region consisting of the amino acid sequence of the amino acid numbers 1 to 122 of SEQ ID NO: 2 and a CH1 region, a CH2 region, and a CH3 region, and the C terminus of one of the structures is linked to the N terminus of the other structure through a linker; and each light chain comprises a light chain variable region consisting of the amino acid sequence of the amino acid numbers 1 to 113 of SEQ ID NO: 4, and a light chain constant region.

[6] An anti-human Tie2 antibody which is an antibody derived from posttranslational modification of the anti-human Tie2 antibody of [5].

[7] The anti-human Tie2 antibody of [6], wherein the posttranslational modification is pyroglutamylation at the N terminus of the heavy chain variable region and/or deletion of lysine at the C terminus of the heavy chain.

[8] The anti-human Tie2 antibody of any one of [3] to [7], comprising a heavy chain constant region which is a human Igγ1 constant region or a human Igγ4 constant region.

[9] The anti-human Tie2 antibody of [8], in which the human Igγ1 constant region is a human Igγ1 constant region having amino acid variations of L234A, L235A, and P331S, or a human Igγ1 constant region having amino acid variations of L234A, L235A, P331S, and I253A.

[10] The anti-human Tie2 antibody of [8], in which the human Igγ4 constant region is a human Igγ4 constant region having amino acid variations of S228P and L235E.

[11] The anti-human Tie2 antibody of any one of [3] to [7], comprising a light chain constant region which is a human Igκ constant region.

[12] The anti-human Tie2 antibody of any one of [3] to [7], comprising a heavy chain constant region which is a human Igγ1 constant region or a human Igγ4 constant region and a light chain constant region which is a human Igκ constant region.

[13] The anti-human Tie2 antibody of [12], in which the human Igγ1 constant region is a human Igγ1 constant region having amino acid variations of L234A, L235A, and P331S, or a human Igγ1 constant region having amino acid variations of L234A, L235A, P331S, and I253A.

[14] The anti-human Tie2 antibody of [12], in which the human Igγ4 constant region is a human Igγ4 constant region having amino acid variations of S228P and L235E.

[15] The anti-human Tie2 antibody of any one of [3] to [7], in which the linker is a peptide linker comprising 5 to 70 amino acids.

[16] The anti-human Tie2 antibody of [15], in which the linker comprises the amino acid sequence of a hinge region or a portion thereof.

[17] The anti-human Tie2 antibody of [16], in which the linker comprises the amino acid sequence shown by SEQ ID NO: 13.

[18] The anti-human Tie2 antibody of [4], comprising two heavy chains consisting of the amino acid sequence shown by SEQ ID NO: 2 and four light chains consisting of the amino acid sequence shown by SEQ ID NO: 4.

[19] The anti-human Tie2 antibody of [4], comprising two heavy chains consisting of the amino acid sequence shown by SEQ ID NO: 6 and four light chains consisting of the amino acid sequence shown by SEQ ID NO: 4.

[20] The anti-human Tie2 antibody of [4], comprising two heavy chains consisting of the amino acid sequence shown by SEQ ID NO: 10 and four light chains consisting of the amino acid sequence shown by SEQ ID NO: 4.

[21] An anti-human Tie2 antibody which is an antibody derived from posttranslational modification of the anti-human Tie2 antibody of any one of [18] to [20]

[22] The anti-human Tie2 antibody of [21], wherein the posttranslational modification is pyroglutamylation at the N terminus of the heavy chain variable region and/or deletion of lysine at the C terminus of the heavy chain.

[23] The anti-human Tie2 antibody of [21], comprising two heavy chains consisting of the amino acid sequence of the amino acid numbers 1 to 678 of SEQ ID NO: 2 and four light chains consisting of the amino acid sequence shown by SEQ ID NO: 4.

[24] A tetravalent anti-human Tie2 antibody or an antigen-binding fragment thereof, binding to the same human Tie2 epitope as the anti-human Tie2 antibody of [18] or [23].

[25] The tetravalent anti-human Tie2 antibody or the antigen-binding fragment thereof of [24], wherein the human Tie2 epitope is the human Tie2 epitope containing the amino acid of the amino acid numbers 192, 195 and 197 of Accession No. NP 000450.2.

[26] A polynucleotide comprising a base sequence encoding the heavy chain variable region of the anti-human Tie2 antibody or the antigen-binding fragment thereof of [2].

[27] A polynucleotide comprising a base sequence encoding the light chain variable region of the anti-human Tie2 antibody or the antigen-binding fragment thereof of [2].

[28] A polynucleotide comprising a base sequence encoding the heavy chain of the anti-human Tie2 antibody of any one of [18] to [20].

[29] A polynucleotide comprising a base sequence encoding the light chain of the anti-human Tie2 antibody of any one of [18] to [20].

[30] An expression vector comprising the polynucleotide of [26] and/or [27].

[31] An expression vector comprising the polynucleotide of [28] and/or [29].

[32] A host cell transformed with the expression vector of [30], which is selected from the group consisting of (a) to (d) below:

(a) a host cell transformed with an expression vector comprising a polynucleotide comprising a base sequence encoding the heavy chain variable region of the anti-human Tie2 antibody or the antigen-binding fragment thereof of [2], and a polynucleotide comprising a base sequence encoding the light chain variable region of the antibody or an antigen-binding fragment thereof;

(b) a host cell transformed with an expression vector comprising a polynucleotide comprising a base sequence encoding the heavy chain variable region of the anti-human Tie2 antibody or the antigen-biding fragment thereof of [2] and an expression vector comprising a polynucleotide comprising a base sequence encoding the light chain variable region of the antibody or an antigen-binding fragment thereof;

(c) a host cell transformed with an expression vector comprising a polynucleotide comprising a base sequence encoding the heavy chain variable region of the anti-human Tie2 antibody or the antigen-binding fragment thereof of [2]; and (d) a host cell transformed with an expression vector comprising a polynucleotide comprising a base sequence encoding the light chain variable region of the anti-human Tie2 antibody or the antigen-binding fragment thereof of [2].

[33] A host cell transformed with the expression vector of [31], selected from the group consisting of (a) to (d) below:

(a) a host cell transformed with an expression vector comprising a polynucleotide comprising a base sequence encoding the heavy chain of the anti-human Tie2 antibody of any one of [18] to [20] and a polynucleotide comprising a base sequence encoding the light chain of the antibody;

(b) a host cell transformed with an expression vector comprising a polynucleotide comprising a base sequence encoding the heavy chain of the anti-human Tie2 antibody of any one of [18] to [20] and an expression vector comprising a polynucleotide comprising a base sequence encoding the light chain of the antibody;

(c) a host cell transformed with an expression vector comprising a polynucleotide comprising a base sequence encoding the heavy chain of the anti-human Tie2 antibody of any one of [18] to [20]; and (d) a host cell transformed with an expression vector comprising a polynucleotide comprising a base sequence encoding the light chain of the anti-human Tie2 antibody of any one of [18] to [20].

[34] A method for producing an anti-human Tie2 antibody or an antigen-binding fragment thereof, comprising culturing host cell(s) selected from the group consisting of (a) to (c) below to express a tetravalent anti-human Tie2 antibody or an antigen-binding fragment thereof:

(a) a host cell transformed with an expression vector comprising a polynucleotide comprising a base sequence encoding the heavy chain variable region of the anti-human Tie2 antibody or the antigen-binding fragment thereof of [2] and a polynucleotide comprising a base sequence encoding the light chain variable region of the antibody or the antigen-binding fragment thereof;

(b) a host cell transformed with an expression vector comprising a polynucleotide comprising a base sequence encoding the heavy chain variable region of the anti-human Tie2 antibody or the antigen-binding fragment thereof of [2] and an expression vector comprising a polynucleotide comprising a base sequence encoding the light chain variable region of the antibody or the antigen-binding fragment thereof, and (c) a host cell transformed with an expression vector comprising a polynucleotide comprising a base sequence encoding the heavy chain variable region of the anti-human Tie2 antibody or the antigen-binding fragment thereof of [2] and a host cell transformed with an expression vector comprising a polynucleotide comprising a base sequence encoding the light chain variable region of the antibody or the antigen-binding fragment thereof.

[35] A method for producing an anti-human Tie2 antibody, comprising culturing host cell(s) selected from the group consisting of (a) to (c) below to express an anti-human Tie2 antibody:

(a) a host cell transformed with an expression vector comprising a polynucleotide comprising a base sequence encoding the heavy chain of the anti-human Tie2 antibody of any one of [18] to [20] and a polynucleotide comprising a base sequence encoding the light chain of the antibody;

(b) a host cell transformed with an expression vector comprising a polynucleotide comprising a base sequence encoding the heavy chain of the anti-human Tie2 antibody of any one of [18] to [20] and an expression vector comprising a polynucleotide comprising a base sequence encoding the light chain of the antibody; and (c) a host cell transformed with an expression vector comprising a polynucleotide comprising a base sequence encoding the heavy chain of the anti-human Tie2 antibody of any one of [18] to [20] and a host cell transformed with an expression vector comprising a polynucleotide comprising a base sequence encoding the light chain of the anti-human Tie2 antibody.

[36] An anti-human Tie2 antibody or an antigen-binding fragment thereof, produced by the method of [34].

[37] An anti-human Tie2 antibody produced by the method of [35].

[38] A pharmaceutical composition comprising the anti-human Tie2 antibody or the antigen-binding fragment thereof of any one of [1] to [23], [36], and [37], and a pharmaceutically acceptable excipient.

[39] A pharmaceutical composition comprising the anti-human Tie2 antibody of [5], the anti-human Tie2 antibody of [6], and a pharmaceutically acceptable excipient.

[40] A pharmaceutical composition comprising the anti-human Tie2 antibody of [18], the anti-human Tie2 antibody of [23], and a pharmaceutically acceptable excipient.

[41] The pharmaceutical composition of any one of [38] to [40], which is a pharmaceutical composition for preventing or treating diabetic macular edema, diabetic retinopathy, or critical limb ischemia.

[42] A method for preventing or treating diabetic macular edema, diabetic retinopathy, or critical limb ischemia, comprising administering a therapeutically effective amount of the anti-human Tie2 antibody or the antigen-binding fragment thereof of any one of [1] to [23], [36], and [37].

[43] The anti-human Tie2 antibody or the antigen-binding fragment thereof of any one of [1] to [23], [36], and [37], for preventing or treating diabetic macular edema, diabetic retinopathy, or critical limb ischemia.

[44] Use of the anti-human Tie2 antibody or the antigen-binding fragment thereof of any one of [1] to [23], [36], and [37] for manufacture of a pharmaceutical composition for preventing or treating diabetic macular edema, diabetic retinopathy, or critical limb ischemia.

The anti-human Tie-2 antibody or the antigen-binding fragment thereof includes a fusion of the antibody with another peptide or protein, and a modification having a modifying agent bound thereto.

Effects of the Invention

The anti-human Tie2 antibody of the present invention can be used as an agent for preventing or treating diabetic macular edema, diabetic retinopathy, or critical limb ischemia by binding to a human Tie2 to activate the human Tie2.

EMBODIMENTS FOR CARRYING OUT THE INVENTION

Figure 1:
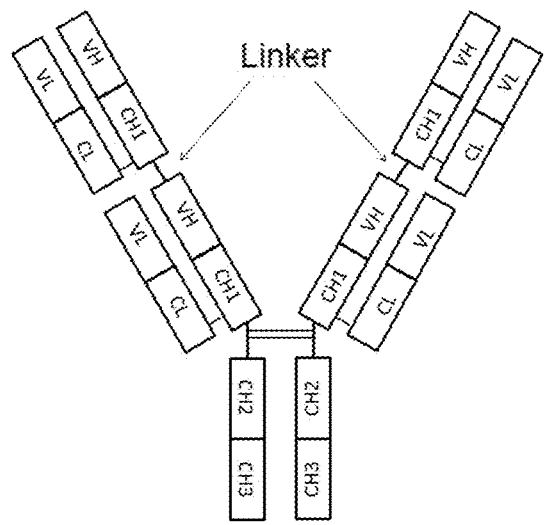
FIG. 1 shows an example of the format of a tetravalent anti-human Tie2 antibody of the present invention.

Hereinafter, the present invention will be described in detail.

There are five classes of IgG IgM, IgA, IgD, and IgE in an antibody. The basic structure of an antibody molecule is configured of heavy chains having a molecular weight of 50000 to 70000 and light chains having a molecular weight of 20000 to 30000 in each of the classes in common. Heavy chain usually consists of a polypeptide chain comprising approximately 440 amino acids, has a distinctive structure for each of the classes, and is referred to as Igγ, Igμ, Igα, and Igδ corresponding to IgG IgM, IgA, IgD, and IgE, respectively. Further, four subclasses of IgG1, IgG2, IgG3, and IgG4 are present in IgG; and the heavy chains respectively corresponding thereto are referred to as Igγ1, Igγ2, Igγ3, and Igγ4. Light chain usually consists of a polypeptide chain comprising approximately 220 amino acids, two types of which, type L and type K are known, and are referred to as Igλ and Igκ. In a peptide configuration of the basic structure of antibody molecules, two homologous heavy chains and two homologous light chains are bound by disulfide bonds (S—S bond) and non-covalent bonds, and the molecular weight thereof is 150000 to 190000. Two kinds of light chains can be paired with any heavy chain.

With regard to intrachain S—S bonds, four of the S—S bonds are present in the heavy chain (five in Igµ and Igε) and two of them are present in the light chain; one loop is formed per 100 to 110 amino acid residues, and this steric structure is similar among the loops and are referred to as a structural unit or a domain. The domain located at the amino-terminal side (N terminal side) in both of the heavy chain and the light chain, whose amino acid sequence is not constant even in a case of a sample from the same class (sub class) of the same kind of animal is referred to as a variable region, and respective domains are referred to as a heavy chain variable region and a light chain variable region. The amino acid sequence of the carboxy-terminal side (C terminal side) from the variable region is nearly constant in each class or subclass and is referred to as a constant region.

An antigen binding site of an antibody is configured of heavy chain variable region (VH) and the light chain variable region (VL), and the binding specificity depends on the amino acid sequence of this site. On the other hand, biological activities such as binding to complements and various cells reflect differences in the constant region structures among each class Ig. It is understood that the variability of variable regions of the light chains and the heavy chains is mostly limited to three small hypervariable regions present in both chains and these regions are referred to as complementarity determining regions (CDR: CDR1, CDR2, and CDR3 from the N terminal side). The remaining portion of the variable region is referred to as a framework region (FR) and is relatively constant.

With regard to the constant region, the heavy chain constant region consists of three regions, which are each called a CH1 region, a CH2 region, and a CH3 region in order from the variable region side. The light chain constant region consists of one region. A peptide sequence called a hinge region is present between the CH1 region and the CH2 region. The hinge region contributes to the mobility of a structure consisting of the heavy chain variable region and the CH1 region.

Further, various kinds of antigen-binding fragments comprising VH and VL of an antibody have antigen binding activity. For example, a single-chain variable region fragment (scFv), Fab, Fab', and F(ab')$_2$ are exemplified as typical antigen-binding fragments. A Fab is a monovalent antigen-binding fragment which is constituted with a light-chain and a heavy-chain fragment comprising a VH, a CH1 region, and a portion of the hinge region. A Fab' is a monovalent antigen-binding fragment which is constituted with a light-chain and a heavy-chain fragment comprising a VH, a CH1 region, and a portion of the hinge region, and cysteine residues constituting the inter-heavy-chain S—S bond are comprised in the portion of the hinge region. A F(ab')$_2$ is a bivalent antigen-binding fragment having a dimeric structure in which two Fab' fragments bind to each other via the inter-heavy-chain S—S bond in the hinge region. An scFv is a monovalent antigen-binding fragment which is constituted with a VH and VL connected with a linker peptide.

An antibody having two or more antigen-binding sites is referred to as a multivalent antibody. Among these, an antibody having four antigen-binding sites is referred to as a tetravalent antibody. For the tetravalent antibody, various formats (structures) have been reported (Nat. Rev. Immunol. 2010, Vol. 10, pp. 301-316; J. Immunol., 2003, Vol. 170, pp. 4854-4861; Mol. Immunol., 2000, Vol. 37, pp. 1067-1077; Biochem. J., 2007, Vol. 406, pp. 237-246; and J. Immunol. Methods, 2003, Vol. 279, pp. 219-232). For example, a tetravalent antibody in which the N terminals of a heavy chain variable region and a light chain variable region of a bivalent antibody are each linked to the C terminals of the heavy chain variable region and the light chain variable region through a linker; a tetravalent antibody comprising two heavy chains and four light chains, in which each heavy chain comprises two structures consisting of a heavy chain variable region and a CH1 region; a tetravalent antibody in which the C terminals of scFv are bonded to each streptavidin of a tetrameric streptavidin one by one; a tetravalent antibody in which the C terminals of scFv are bonded to each p53 of a tetrameric p53 one by one; and a tetravalent antibody in which the N terminals of a CH3 region are linked to the C terminals of a dimeric scFv through a linker have been reported.

<Anti-Human Tie2 Antibody of the Present Invention>

The anti-human Tie2 antibody or the antigen-binding fragment thereof of the present invention includes an anti-human Tie2 antibody or an antigen-binding fragment thereof, having the following characteristics.

An anti-human Tie2 antibody or an antigen-binding fragment thereof, comprising four heavy chain variable regions and four light chain variable regions, in which the heavy chain variable region consists of the amino acid sequence of the amino acid numbers 1 to 122 of SEQ ID NO: 2, the light chain variable region consists of the amino acid sequence of the amino acid numbers 1 to 113 of SEQ ID NO: 4, and the one heavy chain variable region and the one light chain variable region constitute one antigen-binding site, and the antibody or the antigen-binding fragment thereof comprises four antigen-binding sites.

The anti-human Tie2 antibody or the antigen-binding fragment thereof of the present invention is not particularly limited as long as it is a tetravalent antibody, and various formats of tetravalent antibodies described in, for example, Nat. Rev. Immunol. 2010, Vol. 10, pp. 301-316, J. Immunol., 2003, Vol. 170, pp. 4854-4861; Mol. Immunol., 2000, Vol. 37, pp. 1067-1077; Biochem. J., 2007, Vol. 406, pp. 237-246; J. Immunol. Methods, 2003, Vol. 279, pp. 219-232; and the like can be used for the anti-human Tie2 antibody or the antigen-binding fragment thereof of the present invention.

Preferably, the anti-human Tie2 antibody of the present invention comprises two heavy chains and four light chains, each heavy chain comprises two structures consisting of a heavy chain variable region consisting of the amino acid sequence of the amino acid numbers 1 to 122 of SEQ ID NO: 2 and a CH1 region, a CH2 region, and a CH3 region, and the C terminus of one of the structures is linked to the N terminus of the other structure through a linker, and each light chain comprises a light chain variable region consisting of the amino acid sequence of the amino acid numbers 1 to 113 of SEQ ID NO: 4, and a light chain constant region.

Hereinafter, a tetravalent antibody in the format is referred to as a tandem antibody, and an example thereof is shown in FIG. 1.

In the case where the anti-human Tie2 antibody of the present invention is a tandem antibody, a constant region (for example, a constant region of Igγ1, Igγ2, Igγ3 or Igγ4 as a heavy chain constant region, and a constant region of Igλ or Igκ as a light chain constant region) in any subclass can be selected as the constant region. The heavy chain constant region (including a CH1 region, a CH2 region, and a CH3 region) is preferably a human Igγ1 constant region or a human Igγ4 constant region. The light chain constant region is preferably a human Igκ constant region.

In the case where a human Igγ1 constant region is used as the heavy chain constant region of the anti-human Tie2 antibody of the present invention, examples of the CH1 region, the CH2 region, and the CH3 region of the human Igγ1 constant region comprise a CH1 region consisting of the amino acid sequence of the amino acid numbers 350 to 447 of SEQ ID NO: 8, a CH2 region consisting of the amino acid sequence of the amino acid numbers 463 to 572 of SEQ ID NO: 8, and a CH3 region consisting of the amino acid sequence of the amino acid numbers 573 to 679 of SEQ ID NO: 8.

In the case where a human Igγ1 constant region is used as the heavy chain constant region of the anti-human Tie2 antibody of the present invention, a human Igγ1 constant region having introduction of amino acid variation, such as L234A (having substitution of leucine at the amino acid 234th position with alanine according to an EU index such as Kabat), L235A (having substitution of leucine at the amino acid 235th position with alanine according to an EU index such as Kabat), and P331S (having substitution of proline at the amino acid 331st position with serine according to an EU index such as Kabat) can also be used in order to reduce the antibody-dependent cellular cytotoxicity or the complement-dependent cytotoxicity activity of an antibody (Mol. Immunol., 1992, Vol. 29, No. 5, pp. 633-639). Further, from the viewpoint of pharmacokinetics, a human Igγ1 constant region to which amino acid variations has been introduced, such as I253A (having substitution of isoleucine at the amino acid 253th position with alanine according to an EU index such as Kabat) can also be used in order to attain a rapid loss in the blood (J. Immunol., 1997, Vol. 158, pp. 2211-2217). The residue numbers with respect to the introduction of amino acid variation in the constant region of the antibody used in the present specification are in accordance with an EU index (Kabat et al., 1991, Sequences of Proteins of Immunological Interest, 5th Ed., United States Public Health Service, National Institute of Health, Bethesda).

In the case where a human Igγ1 constant region is used as the heavy chain constant region of the anti-human Tie2 antibody of the present invention, the human Igγ1 constant region is preferably a human Igγ1 constant region having amino acid variations of L234A, L235A, and P331S, or L234A, L235A, P331S and I253A. Examples of the CH1 region, the CH2 region, and CH3 region of the human Igγ1 constant region having amino acid variations of L234A, L235A, and P331S comprise a CH1 region consisting of the amino acid sequence of the amino acid numbers 350 to 447 of SEQ ID NO: 2, a CH2 region consisting of the amino acid sequence of the amino acid numbers 463 to 572 of SEQ ID NO: 2, and a CH3 region consisting of the amino acid sequence of the amino acid numbers 573 to 679 of SEQ ID NO: 2. Examples of the CH1 region, the CH2 region, and the CH3 region of the human Igγ1 constant region having amino acid variations of L234A, L235A, P331S, and I253A comprise a CH1 region consisting of the amino acid sequence of the amino acid numbers 350 to 447 of SEQ ID NO: 6, a CH2 region consisting of the amino acid sequence of the amino acid numbers 463 to 572 of SEQ ID NO: 6, and a CH3 region consisting of the amino acid sequence of the amino acid numbers 573 to 679 of SEQ ID NO: 6.

In the case where a human Igγ4 constant region is used as the heavy chain constant region of the anti-human Tie2 antibody of the present invention, a human Igγ4 constant region having introduction of amino acid variations such as S228P (having substitution of serine at the amino acid 228th position with proline according to an EU index such as Kabat) and L235E (having substitution of leucine at the amino acid 235st position with glutamic acid according to an EU index such as Kabat) can also be used in order to inhibit Fab arm exchange (Drug Metab. Dispos., 2010, Vol. 38, No. 1, pp. 84-91).

In the case where a human Igγ4 constant region is used as the heavy chain constant region of the anti-human Tie2 antibody of the present invention, the human Igγ4 constant region is preferably a human Igγ4 constant region having amino acid variations of S228P and L235E. Examples of the CH1 region, the CH2 region, and the CH3 region of the human Igγ4 constant region having amino acid variations of S228P and L235E comprise a CH1 region consisting of the amino acid sequence of the amino acid numbers 350 to 447 of SEQ ID NO: 10, a CH2 region consisting of the amino acid sequence of the amino acid numbers 460 to 569 of SEQ ID NO: 10, and a CH3 region consisting of the amino acid sequence of the amino acid numbers 570 to 676 of SEQ ID NO: 10.

Examples of the human Igκ constant region include a human Igκ constant region consisting of the amino acid sequence of the amino acid numbers 114 to 219 of SEQ ID NO: 4.

Preferably, in the case where the anti-human Tie2 antibody of the present invention is a tandem antibody, the heavy chain constant region is a human Igγ1 constant region or a human Igγ4 constant region, and the light chain constant region is a human Igκ constant region. In the case where the heavy chain constant region is a human Igγ1 constant region, the human Igγ1 constant region is preferably a human Igγ1 constant region having amino acid variations of L234A, L235A, and P331S, or a human Igγ1 constant region having amino acid variations of L234A, L235A, P331S, and I253A. In the case where the heavy chain constant region is a human Igγ4 constant region, the human Igγ4 constant region is preferably a human Igγ4 constant region having amino acid variations of S228P and L235E.

In the case where the anti-human Tie2 antibody of the present invention is a tandem antibody, as a linker that links the structures consisting of a heavy chain variable region and a CH1 region, any peptide (peptide linker) can be used as long as the antibody has such a function. The length of the peptide linker and the amino acid sequence can be appropriately selected by a person skilled in the art. The peptide linker preferably has 5 to 70 amino acids in length. The peptide linker preferably comprises the amino acid sequence of a hinge region or a portion thereof. The hinge region means a region that exists between the CH1 region and the CH2 region of an antibody, and examples of the hinge region to be used comprise a hinge region of IgG1 or IgG3. A portion of the hinge region means a region having at least 5 successive amino acids in the hinge region, and preferably means a region having at least 5 successive amino acids from the N terminus of the hinge region. Examples of a part of the hinge region include a region having 5 successive amino acids from the N terminal (consisting of the amino acid sequence of the amino acid numbers 1 to 5 of SEQ ID NO: 13) in the case of the hinge region of IgG1 and a region having 12 successive amino acids from the N terminal (consisting of the amino acid sequence of the amino acid numbers 1 to 12 of SEQ ID NO: 14) in the case of the hinge region of IgG3. In one embodiment, the linker comprises the amino acid sequence of a region having at least 5 successive amino acids from the N terminus of the hinge region and comprises amino acid sequence GlySer at the C terminus of the linker. Examples of such a linker comprise a peptide linker consisting of the amino acid sequence shown by any one of SEQ ID NOS: 13 to 20, and the linker preferably consists of the amino acid sequence shown by SEQ ID NO: 13.

In one embodiment, the anti-human Tie2 antibody of the present invention is an anti-human Tie2 antibody having any one of the following characteristics i) to iv).

i) An anti-human Tie2 antibody comprising two heavy chains consisting of the amino acid sequence shown by SEQ ID NO: 2 and four light chains consisting of the amino acid sequence shown by SEQ ID NO: 4.

ii) An anti-human Tie2 antibody comprising two heavy chains consisting of the amino acid sequence shown by SEQ ID NO: 6 and four light chains consisting of the amino acid sequence shown by SEQ ID NO: 4.

iii) An anti-human Tie2 antibody comprising two heavy chains consisting of the amino acid sequence shown by SEQ ID NO: 8 and four light chains consisting of the amino acid sequence shown by SEQ ID NO: 4.

iv) An anti-human Tie2 antibody comprising two heavy chains consisting of the amino acid sequence shown by SEQ ID NO: 10 and four light chains consisting of the amino acid sequence shown by SEQ ID NO: 4.

It is known that when an antibody is expressed in cells, the antibody is modified after translation. Examples of the posttranslational modification include cleavage of lysine at the C terminal of the heavy chain by a carboxypeptidase; modification of glutamine or glutamic acid at the N terminal of the heavy chain and the light chain to pyroglutamic acid by pyroglutamylation; glycosylation; oxidation; deamidation; and glycation, and it is known that such posttranslational modifications occur in various antibodies (Journal of Pharmaceutical Sciences, 2008, Vol. 97, p. 2426-2447).

The anti-human Tie2 antibody or the antigen-binding fragment thereof of the present invention includes an anti-human Tie2 antibody or an antigen-binding fragment thereof, which has undergone posttranslational modification. Examples of the anti-human Tie2 antibody or the antigen-binding fragment thereof of the present invention, which undergoes posttranslational modification, include anti-human Tie2 antibodies or antigen-binding fragments thereof, which have undergone pyroglutamylation at the N terminal of
the heavy chain variable region and/or deletion of lysine at the C terminal of the heavy chain. It is known in the field that such posttranslational modification due to pyroglutamylation at the N terminal and deletion of lysine at the C terminal does not have any influence on the activity of the antibody (Analytical Biochemistry, 2006, Vol. 348, p. 24-39).

In one embodiment, the anti-human Tie2 antibody of the present invention is an anti-human Tie2 antibody having any one of the following characteristics (1) to (4).

(1) An anti-human Tie2 antibody comprising two heavy chains consisting of the amino acid sequence in which glutamic acid of the amino acid number 1 of SEQ ID NO: 2 is modified to pyroglutamic acid and/or lysine of the amino acid number 679 of SEQ ID NO: 2 is deleted and four light chains consisting of the amino acid sequence shown by SEQ ID NO: 4.

(2) An anti-human Tie2 antibody comprising two heavy chains consisting of the amino acid sequence in which glutamic acid of the amino acid number 1 of SEQ ID NO: 6 is modified to pyroglutamic acid and/or lysine of the amino acid number 679 of SEQ ID NO: 6 is deleted and four light chains consisting of the amino acid sequence shown by SEQ ID NO: 4.

(3) An anti-human Tie2 antibody comprising two heavy chains consisting of the amino acid sequence in which glutamic acid of the amino acid number 1 of SEQ ID NO: 8 is modified to pyroglutamic acid and/or lysine of the amino acid number 679 of SEQ ID NO: 8 is deleted and four light chains consisting of the amino acid sequence shown by SEQ ID NO: 4.

(4) An anti-human Tie2 antibody comprising two heavy chains consisting of the amino acid sequence in which glutamic acid of the amino acid number 1 of SEQ ID NO: 10 is modified to pyroglutamic acid and/or lysine of the amino acid number 676 of SEQ ID NO: 10 is deleted and four light chains consisting of the amino acid sequence shown by SEQ ID NO: 4.

In one embodiment, the anti-human Tie2 antibody of the present invention is an anti-human Tie2 antibody having the following characteristics.

An anti-human Tie2 antibody comprising two heavy chains consisting of the amino acid sequence of the amino acid numbers 1 to 678 of SEQ ID NO: 2 and four light chains consisting of the amino acid sequence shown by SEQ ID NO: 4.

The present invention further includes an anti-human Tie2 antibody or an antigen-binding fragment thereof, having the following characteristics.

An anti-human Tie2 antibody or an antigen-binding fragment thereof, comprising four heavy chain variable regions and four light chain variable regions, in which the heavy chain variable region comprises CDR1 consisting of the amino acid sequence of the amino acid numbers 31 to 35 of SEQ ID NO: 2, CDR2 consisting of the amino acid sequence of the amino acid numbers 50 to 66 of SEQ ID NO: 2, and CDR3 consisting of the amino acid sequence of the amino acid numbers 99 to 111 of SEQ ID NO: 2, the light chain variable region comprises CDR1 consisting of the amino acid sequence of the amino acid numbers 24 to 39 of SEQ ID NO: 4, CDR2 consisting of the amino acid sequence of the amino acid numbers 55 to 61 of SEQ ID NO: 4, and CDR3 consisting of the amino acid sequence of the amino acid numbers 94 to 102 of SEQ ID NO: 4, and the one heavy chain variable region and the one light chain variable region constitute one antigen-binding site, and the antibody or the antigen-binding fragment thereof comprises four antigen-binding sites.

In addition, the present invention further includes an anti-human Tie2 antibody having the following characteristics.

An anti-human Tie2 antibody comprising two heavy chains and four light chains, in which each heavy chain comprises two structures consisting of a heavy chain variable region comprising CDR1 consisting of the amino acid sequence of the amino acid numbers 31 to 35 of SEQ ID NO: 2, CDR2 consisting of the amino acid sequence of the amino acid numbers 50 to 66 of SEQ ID NO: 2, and CDR3 consisting of the amino acid sequence of the amino acid numbers 99 to 111 of SEQ ID NO: 2 and a CH1 region, a CH2 region, and a CH3 region, and the carboxy terminus of one of the structures is linked to the amino terminus of the other structure through a linker, and each light chain comprises a light chain variable region comprising CDR1 consisting of the amino acid sequence of the amino acid numbers 24 to 39 of SEQ ID NO: 4, CDR2 consisting of the amino acid sequence of the amino acid numbers 55 to 61 of SEQ ID NO: 4, and CDR3 consisting of the amino acid sequence of the amino acid numbers 94 to 102 of SEQ ID NO: 4, and a light chain constant region.

The anti-human Tie2 antibody of the present invention is an antibody that binds to a human Tie2. Whether the antibody binds to the human Tie2 (Accession No. NP_000450.2) can be confirmed by using a known binding activity measurement method. Examples of the binding activity measurement method include a method of Enzyme-Linked ImmunoSorbent Assay (ELISA) or the like. In a case of using the ELISA, in an exemplary method, a protein formed by fusion of the human Tie2 with a human Fc is immobilized on an ELISA plate, and a test antibody is added thereto to be reacted. A secondary antibody such as a biotin-labeled anti-IgG antibody is reacted with the resultant, washed, and then reacted with streptavidin to which an enzyme such as an alkaline phosphatase is bound. After washing, it is possible to confirm whether the test antibody binds to the human Tie2 by carrying out activity measurement using an activity-detecting reagent (for example, in the case of the alkaline phosphatase, Chemiluminescent Ultra Sensitive AP Microwell and/or Membrane Substrate (450 nm) (BioFX, APU4-0100-01) or the like)). As a specific method for evaluating the activity, the same method as the one described in Example 12 as described later, for example, can be used.

The anti-human Tie2 antibody of the present invention further includes an antibody binding to Tie2 derived from other animals (for example, monkey Tie2) in addition to binding to a human Tie2 as long as it is an antibody binding to a human Tie2.

Preferably, the anti-human Tie2 antibody of the present invention binds to a human Tie2, and further, has anti-apoptotic activity with respect to a human Tie2-expressing cell. As a specific method for evaluating whether the antibody has anti-apoptotic activity with respect to a human Tie2-expressing cell, for example, the same method as the one described in Example 4 as described later can be used.

The anti-human Tie2 antibody or the antigen-binding fragment thereof of the present invention includes a tetravalent anti-human Tie2 antibody or an antigen-binding fragment thereof which binds to the same human Tie2 epitope as the anti-human Tie2 antibody comprising two heavy chains consisting of the amino acid sequence shown by SEQ ID NO: 2 and four light chains consisting of the amino acid sequence shown by SEQ ID NO: 4, or as the anti-human Tie2 antibody comprising two heavy chains consisting of the amino acid sequence of the amino acid numbers 1 to 678 of SEQ ID NO: 2 and four light chains consisting of the amino acid sequence shown by SEQ ID NO: 4. Here, the epitope refers to an antigen site recognized by an antibody.

The anti-human Tie2 antibody or the antigen-binding fragment thereof of the present invention includes a tetravalent anti-human Tie2 antibody or an antigen-binding fragment thereof, which binds to an epitope comprising at least one amino acid of the amino acids of the amino acid numbers 192, 195 and 197 of a human Tie2 (Accession No. NP_000450.2).

Moreover, the anti-human Tie2 antibody or the antigen-binding fragment thereof of the present invention includes a tetravalent anti-human Tie2 antibody or an antigen-binding fragment thereof, which binds to an epitope comprising the amino acids of the amino acid numbers 192, 195 and 197 of a human Tie2 (Accession No. NP_000450.2).

The tetravalent anti-human Tie2 antibody or the antigen-binding fragment thereof, which binds to the same human Tie2 epitope as the anti-human Tie2 antibody comprising two heavy chains consisting of the amino acid sequence shown by SEQ ID NO: 2 and four light chains consisting of the amino acid sequence shown by SEQ ID NO: 4, or as the anti-human Tie2 antibody comprising two heavy chains consisting of the amino acid sequence of the amino acid numbers 1 to 678 of SEQ ID NO: 2 and four light chains consisting of the amino acid sequence shown by SEQ ID NO: 4 can be acquired by using a known method for determining an epitope. Examples of the method for determining an epitope include hydrogen/deuterium exchange mass spectrometry, X-ray crystal structure analysis, ELISA and a surface plasmon resonance phenomenon using an amino acid substitution mutant of a human Tie2, a partial peptide of human Tie2, or the like, and the like.

It is possible to check whether the test antibody binds to the same human Tie2 epitope as the anti-human Tie2 antibody comprising two heavy chains consisting of the amino acid sequence shown by SEQ ID NO: 2 and four light chains consisting of the amino acid sequence shown by SEQ ID NO: 4, or as the anti-human Tie2 antibody comprising two heavy chains consisting of the amino acid sequence of the amino acid numbers 1 to 678 of SEQ ID NO: 2 and four light chains consisting of the amino acid sequence shown by SEQ ID NO: 4 by using the well-known method for determining an epitope as described above. In the case of using hydrogen/deuterium exchange mass spectrometry, a human Tie2 with deuterium substitution in the absence of a test antibody and a human Tie2 with deuterium substitution in the presence of a test antibody are each decomposed by peptides, and the amount of molecules of each peptide is measured to calculate the ratio of deuterium substitution. The human Tie2 epitope of the test antibody can be determined from the difference in the ratios of deuterium substitution of the human Tie2 according to the presence or absence of the test antibody. In the case of using ELISA, a point mutant of a human Tie2 is prepared. The mutant human Tie2 is immobilized and a test antibody is added thereto to undergo a reaction. After the reaction, a secondary antibody such as a biotin-labeled anti-human kappa light chain antibody is reacted and washed. Thereafter, an alkaline phosphatase-labeled streptavidin (Thermo Fisher Scientific, 21324) is reacted therewith and washed. Further, it is possible to identify whether or not the test antibody binds to the mutant human Tie2 by carrying out activity measurement using Chemiluminescent Ultra Sensitive AP Microwell and/or Membrane Substrate (450 nm), or the like. It is possible to determine an epitope of the test antibody by evaluating the binding activity to various types of mutant human Tie2. In the case where the epitope of the test antibody comprises at least one amino acid in the epitope of the anti-human Tie2 antibody comprising two heavy chains consisting of the amino acid sequence shown by SEQ ID NO: 2 and four light chains consisting of the amino acid sequence shown by SEQ ID NO: 4, or the anti-human Tie2 antibody comprising two heavy chains consisting of the amino acid sequence of the amino acid numbers 1 to 678 of SEQ ID NO: 2 and four light chains consisting of the amino acid sequence shown by SEQ ID NO: 4, it can be determined that the test antibody binds to the same human Tie2 epitope as the anti-human Tie2 antibody comprising two heavy chains consisting of the amino acid sequence shown by SEQ ID NO: 2 and four light chains consisting of the amino acid sequence shown by SEQ ID NO: 4, or as the anti-human Tie2 antibody comprising a heavy chain consisting of the amino acid sequence of the amino acid numbers 1 to 678 of SEQ ID NO: 2 and a light chain consisting of the amino acid sequence shown by SEQ ID NO: 4.

The anti-human Tie2 antibody or the antigen-binding fragment thereof of the present invention can be easily prepared by a person skilled in the art, using a method known in the art, based on the sequence information of the heavy chain variable region and the light chain variable region of the antibody of the present invention, as disclosed in the present specification. The anti-human Tie2 antibody or the antigen-binding fragment thereof of the present invention is not particularly limited, but can be produced in accordance with the method described in <Method for Producing Anti-Human Tie2 Antibody of the Present Invention and Anti-Human Tie2 Antibody Produced by the Method> as described later, for example.

The anti-human Tie2 antibody or the antigen-binding fragment thereof of the present invention is further purified as needed, and formulated according to a conventional method. It may be used for the prevention or the treatment of blood vessel-related diseases such as diabetic retinopathy, diabetic macular edema, sepsis, acute hepatic disorders, acute renal disorders, acute pulmonary disorders, systemic inflammatory reaction syndrome, peripheral arterial occlusive disease, or critical limb ischemia.

<Polynucleotide of the Present Invention>

The polynucleotide of the present invention includes a polynucleotide comprising a base sequence encoding the heavy chain variable region of the anti-human Tie2 antibody or the antigen-binding fragment thereof of the present invention and a polynucleotide comprising a base sequence encoding the light chain variable region of the anti-human Tie2 antibody or the antigen-binding fragment thereof of the present invention.

In one embodiment, the polynucleotide comprising a base sequence encoding the heavy chain variable region of the anti-human Tie2 antibody or the antigen-binding fragment thereof of the present invention is a polynucleotide comprising a base sequence encoding the heavy chain variable region consisting of the amino acid sequence of the amino acid numbers 1 to 122 of SEQ ID NO: 2.

Examples of the polynucleotide comprising a base sequence encoding the heavy chain variable region shown by the amino acid sequence of the amino acid numbers 1 to 122 of SEQ ID NO: 2 include a polynucleotide comprising the base sequence of the base numbers 1 to 366 of SEQ ID NO: 1.

In a preferred embodiment, the polynucleotide comprising a base sequence encoding the heavy chain variable region of the anti-human Tie2 antibody or the antigen-binding fragment thereof of the present invention is a polynucleotide comprising a base sequence encoding the heavy chain consisting of the amino acid sequence shown by SEQ ID NO: 2, a polynucleotide comprising a base sequence encoding the heavy chain consisting of the amino acid sequence shown by SEQ ID NO: 6, a polynucleotide comprising a base sequence encoding the heavy chain consisting of the amino acid sequence shown by SEQ ID NO: 8, or a polynucleotide comprising a base sequence encoding the heavy chain consisting of the amino acid sequence shown by SEQ ID NO: 10.

Examples of the polynucleotide comprising a base sequence encoding the heavy chain consisting of the amino acid sequence shown by SEQ ID NO: 2 include a polynucleotide comprising the base sequence shown by SEQ ID NO: 1. Examples of the polynucleotide comprising a base sequence encoding the heavy chain consisting of the amino acid sequence shown by SEQ ID NO: 6 include a polynucleotide comprising the base sequence shown by SEQ ID NO: 5. Examples of the polynucleotide comprising a base sequence encoding the heavy chain consisting of the amino acid sequence shown by SEQ ID NO: 8 include a polynucleotide comprising the base sequence shown by SEQ ID NO: 7. Examples of the polynucleotide comprising a base sequence encoding the heavy chain consisting of the amino acid sequence shown by SEQ ID NO: 10 include a polynucleotide comprising the base sequence shown by SEQ ID NO: 9.

In one embodiment, the polynucleotide comprising a base sequence encoding the light chain variable region of the anti-human Tie2 antibody or the antigen-binding fragment thereof of the present invention is a polynucleotide comprising a base sequence encoding the light chain variable region consisting of the amino acid sequence of the amino acid numbers 1 to 113 of SEQ ID NO: 4.

Examples of the polynucleotide comprising a base sequence encoding the light chain variable region shown by the amino acid sequence of the amino acid numbers 1 to 113 of SEQ ID NO: 4 include a polynucleotide comprising the base sequence of the base numbers 1 to 339 of SEQ ID NO: 3.

In a preferred embodiment, the polynucleotide comprising a base sequence encoding the light chain variable region of the anti-human Tie2 antibody or the antigen-binding fragment thereof of the present invention is a polynucleotide comprising a base sequence encoding the light chain consisting of the amino acid sequence shown by SEQ ID NO: 4.

Examples of the polynucleotide comprising a base sequence encoding the light chain consisting of the amino acid sequence shown by SEQ ID NO: 4 include a polynucleotide comprising a base sequence shown by SEQ ID NO: 3.

The polynucleotide of the present invention can be easily prepared by a person skilled in the art using a known method in the field based on the base sequence. For example, the polynucleotide of the present invention can be synthesized using a known gene synthesis method in the field. As the gene synthesis method, various methods such as a synthesis method of antibody genes described in WO90/07861 known by a person skilled in the art can be used. Further, once the polynucleotide of the present invention is acquired, it is possible to acquire other polynucleotides of the present invention by introducing a variation into a predetermined site of the polynucleotide. As such a method for introducing the variation, various methods known to a person skilled in the art, such as a site-specific mutagenesis method (Current Protocols in Molecular Biology edit., 1987, John Wiley & Sons Section 8.1-8.5), can be used.

<Expression Vector of the Present Invention>

The expression vector of the present invention includes the polynucleotide comprising a base sequence encoding the heavy chain variable region of the anti-human Tie2 antibody or the antigen-binding fragment thereof of the present invention and/or the polynucleotide comprising a base sequence encoding the light chain variable region of the anti-human Tie2 antibody or the antigen-binding fragment thereof of the present invention. Tetravalent antibodies in various formats and methods for producing the same are well-known in the art, and the expression vector of the present invention can be easily established by a person skilled in the art according to such production methods or the formats of the tetravalent antibodies to be expressed.

Preferred examples of the expression vector of the present invention include an expression vector comprising a polynucleotide comprising a base sequence encoding the heavy chain of the anti-human Tie2 antibody of the present invention, an expression vector comprising a polynucleotide comprising a base sequence encoding the light chain of the anti-human Tie2 antibody of the present invention, and an expression vector comprising a polynucleotide comprising a base sequence encoding the heavy chain of the anti-human Tie2 antibody of the present invention and a polynucleotide comprising a base sequence encoding the light chain of the antibody.

The expression vector used to express the polynucleotide of the present invention are not particularly limited as long as a polynucleotide comprising the base sequence encoding the heavy chain variable region of the anti-human Tie2 antibody or the antigen-biding fragment thereof of the present invention and/or a polynucleotide comprising the base sequence encoding the light chain variable region of the anti-human Tie2 antibody or the antigen-biding fragment thereof of the present invention can be expressed in various host cells of eukaryotic cells (for example, animal cells, insect cells, plant cells, and yeast) and/or prokaryotic cells (for example, *Escherichia coli*), and the polypeptides encoded by these can be produced. Examples of the expression vector include plasmid vectors, viral vectors (for example, adenovirus, adeno-associated virus, Sendai virus or retrovirus), and the like. Preferably pEE6.4 or pEE12.4 (Lonza, Inc.) can be used. Further, antibody genes can be expressed by using expression vectors comprising human Ig constant region genes in advance such as AG-γ1 or AG-κ (for example, see WO94/20632).

The expression vector of the present invention may comprise a promoter that is operably linked to the polynucleotide of the present invention. Examples of the promoter for expressing the polynucleotide of the invention with animal cells include a virus-derived promoter such as CMV, RSV, or SV40, an actin promoter, an EF (elongation factor) la promoter, and a heat shock promoter. Examples of promoters for expression by bacteria (for example, *Escherichia*) include a trp promoter, a lac promoter, λPL promoter, and tac promoter. Further, examples of promoters for expression by yeast include a GAL1 promoter, a GAL10 promoter, a PHO5 promoter, a PGK promoter, a GAP promoter, and an ADH promoter.

In the case of using an animal cell, an insect cell, or yeast as the host cell, the expression vector of the present invention may comprise initiation codon and termination codon. In this case, the expression vector of the present invention may comprise an enhancer sequence, an untranslated region on the 5' side and the 3' side of genes encoding the antibody of the present invention or the heavy chain variable region or the light chain variable region, a secretory signal sequence, a splicing junction, a polyadenylation site, or a replicable unit. When *Escherichia coli* is used as the host cell, the expression vector of the present invention may comprise an initiation codon, a termination codon, a terminator region, and a replicable unit. In this case, the expression vector of the present invention may comprise a selection marker (for example, tetracycline resistant genes, ampicillin resistant genes, kanamycin resistant genes, neomycin resistant genes, or dihydrofolate reductase genes) which is generally used according to the necessity.

<Transformed Host Cell of the Present Invention>

The transformed host cell of the present invention includes a host cell transformed with the expression vector of the present invention which is selected from the group consisting of (a) to (d) below:

(a) a host cell transformed with an expression vector comprising a polynucleotide comprising a base sequence encoding the heavy chain variable region of the anti-human Tie2 antibody or the antigen-binding fragment thereof of the present invention, and a polynucleotide comprising a base sequence encoding the light chain variable region of the antibody or the antigen-binding fragment thereof;

(b) a host cell transformed with an expression vector comprising a polynucleotide comprising a base sequence encoding the heavy chain variable region of the anti-human Tie2 antibody or the antigen-binding fragment thereof of the present invention and an expression vector comprising a polynucleotide comprising a base sequence encoding the light chain variable region of the antibody or the antigen-binding fragment thereof;

(c) a host cell transformed with an expression vector comprising a polynucleotide comprising a base sequence encoding the heavy chain variable region of the anti-human Tie2 antibody or the antigen-binding fragment thereof of the present invention; and (d) a host cell transformed with an expression vector comprising a polynucleotide comprising a base sequence encoding the light chain variable region of the anti-human Tie2 antibody or the antigen-binding fragment thereof of the present invention.

In one embodiment, the transformed host cell of the present invention is a host cell transformed with the expression vector of the present invention, which is selected from the group consisting of (a) to (d) below:

(a) a host cell transformed with an expression vector comprising a polynucleotide comprising a base sequence encoding the heavy chain of the anti-human Tie2 antibody of the present invention and a polynucleotide comprising a base sequence encoding the light chain of the antibody;

(b) a host cell transformed with an expression vector comprising a polynucleotide comprising a base sequence encoding the heavy chain of the anti-human Tie2 antibody of the present invention and an expression vector comprising a polynucleotide comprising a base sequence encoding the light chain of the antibody;

(c) a host cell transformed with an expression vector comprising a polynucleotide comprising a base sequence encoding the heavy chain of the anti-human Tie2 antibody of the present invention; and (d) a host cell transformed with an expression vector comprising a polynucleotide comprising a base sequence encoding the light chain of the anti-human Tie2 antibody of the present invention.

Preferred examples of the transformed host cell of the present invention include a host cell transformed with an expression vector comprising a polynucleotide comprising a base sequence encoding the heavy chain of the anti-human Tie2 antibody of the present invention and a polynucleotide comprising a base sequence encoding the light chain of the antibody, and a host cell transformed with an expression vector comprising a polynucleotide comprising a base sequence encoding the heavy chain of the anti-human Tie2 antibody of the present invention and an expression vector comprising a polynucleotide comprising a base sequence encoding the light chain of the antibody.

The transformed host cell is not particularly limited as long as the host cell is appropriate for the expression vector being used, transformed with the expression vector, and can express the antibody. Examples of the transformed host cell include various cells such as natural cells or artificially established cells which are generally used in the field of the present invention (for example, animal cells (for example, CHO-K1SV cells), insect cells (for example, Sf9), bacteria (for example, *Escherichia*), yeast (for example, *Saccharomyces* or *Pichia*) or the like). Preferably cultured cells such as CHO cells (CHO-K1SV cells, CHO-DG 44 cells, or the like) 293 cells, or NS0 cells can be used.

A method of transforming the host cell is not particularly limited, but, for example, a calcium phosphate method or an electroporation method can be used.

<Method for Producing Anti-Human Tie2 Antibody of the Present Invention and Anti-Human Tie2 Antibody Produced by the Method>

Examples of the method for producing the anti-human Tie2 antibody or the antigen-binding fragment thereof of the present invention include a method for producing an anti-human Tie2 antibody or a antigen-binding fragment thereof, comprising culturing host cell(s) selected from the group consisting of (a) to (c) below to express a tetravalent anti-human Tie2 antibody or an antigen-binding fragment thereof:

(a) a host cell transformed with an expression vector comprising a polynucleotide comprising a base sequence encoding the heavy chain variable region of the anti-human Tie2 antibody or the antigen-binding fragment thereof of the present invention and a polynucleotide comprising a base sequence encoding the light chain variable region of the antibody or the antigen-binding fragment thereof;

(b) a host cell transformed with an expression vector comprising a polynucleotide comprising a base sequence encoding the heavy chain variable region of the anti-human Tie2 antibody or the antigen-binding fragment thereof of the present invention and an expression vector comprising a polynucleotide comprising a base sequence encoding the light chain variable region of the antibody or the antigen-binding fragment thereof; and (c) a host cell transformed with an expression vector comprising a polynucleotide comprising a base sequence encoding the heavy chain variable region of the anti-human Tie2 antibody or the antigen-binding fragment thereof of the present invention and a host cell transformed with an expression vector comprising a polynucleotide comprising a base sequence encoding the light chain variable region of the antibody or the antigen-binding fragment thereof.

In one embodiment, examples of the method for producing the anti-human Tie2 antibody of the present invention include a method for producing an anti-human Tie2 antibody, comprising culturing host cell(s) selected from the group consisting of (a) to (c) below to express an anti-human Tie2 antibody:

(a) a host cell transformed with an expression vector comprising a polynucleotide comprising a base sequence encoding the heavy chain of the anti-human Tie2 antibody of the present invention and a polynucleotide comprising a base sequence encoding the light chain of the antibody;

(b) a host cell transformed with an expression vector comprising a polynucleotide comprising a base sequence encoding the heavy chain of the anti-human Tie2 antibody of the present invention and an expression vector comprising a polynucleotide comprising a base sequence encoding the light chain of the antibody; and (c) a host cell transformed with an expression vector comprising a polynucleotide comprising a base sequence encoding the heavy chain of the anti-human Tie2 antibody of the present invention and a host cell transformed with an expression vector comprising a polynucleotide comprising a base sequence encoding the light chain of the antibody.

The method for producing the anti-human Tie2 antibody of the present invention is not particularly limited as long as it comprises a step of culturing the transformed host cells of the present invention to express the anti-human Tie2 antibody. Examples of the preferred host cells for use in the method include the preferred transformed host cells of the present invention as described above.

The transformed host cell can be cultured by known methods. Culture conditions, for example, the temperature, pH of culture medium, and the culture time are appropriately selected. In a case where the host cell is an animal cell, examples of the culture medium include MEM culture medium supplemented with approximately 5% to 20% of fetal bovine serum (Science, 1959, Vol. 130, No. 3373, p. 432 to 7), DMEM culture medium (Virology, 1959, Vol. 8, p. 396), and RPMI1640 culture medium (J. Am. Mde. Assoc., 1967, Vol. 199, p. 519), a 199 culture medium (Exp. Biol. Med., 1950, Vol. 73, p. 1 to 8). The pH of the culture medium is preferably approximately 6 to 8, and the culture is generally carried out at approximately 30° C. to 40° C. for approximately 15 hours to 72 hours while air ventilating and stirring if necessary. In a case where the host cell is an insect cell, as the culture medium, for example, Grace's culture medium (Proc. Natl. Acad. Sci. USA, 1985, Vol. 82, p. 8404) supplemented with fetal bovine serum can be used. The pH of the culture medium is preferably approximately 5 to 8, and the culture is generally carried out at approximately 20° C. to 40° C. for approximately 15 hours to 100 hours while air ventilating and stirring if necessary. In a case where the host cell is *Escherichia coli* or yeast, as the culture medium, for example, liquid culture medium supplemented with a source of nutrients is appropriate. It is preferable that the nutrient culture medium contain a carbon source, an inorganic nitrogen source, or an organic nitrogen source necessary for the growth of the transformed host cell. Examples of the carbon source include glucose, dextran, soluble starch, and sucrose and examples of the inorganic nitrogen source or the organic nitrogen source include ammonium salts, nitrate salts, amino acids, corn steep liquor, peptone, casein, meat extract, soybean meal, and potato extract. Other nutrients (for example, inorganic salts (for example, calcium chloride, sodium dihydrogen phosphate, and magnesium chloride), vitamins), and antibiotics (for example, tetracycline, neomycin, ampicillin, and kanamycin) may be contained as desired. The pH of the culture medium is preferably approximately 5 to 8. In a case where the host cell is *Escherichia coli*, preferred examples of the culture medium include LB culture medium and M9 culture medium (Mol. Clo., Cold Spring Harbor Laboratory, Vol. 3, A2.2). The culture is generally carried out at approximately 14° C. to 39° C. for approximately 3 hours to 24 hours while air ventilating and stirring if necessary. In a case where the host cell is yeast, as the culture medium, for example, Burkholder minimal medium (Proc. Natl. Acad, Sci, USA, 1980, Vol. 77, p. 4505) can be used. The culture is generally carried out at approximately 20° C. to 35° C. for approximately 14 hours to 144 hours while air ventilating and stirring if necessary. By carrying out the culture in the above-described manner, it is possible to express the anti-human Tie2 antibody or the antigen-binding fragment thereof of the present invention.

The method of producing the anti-human Tie2 antibody or the antigen-binding fragment thereof of the present invention may comprise recovering, preferably isolating or purifying the anti-human Tie2 antibody or the antigen-binding fragment thereof from the transformed host cell in addition to culturing the transformed host cell of the present invention to express the anti-human Tie2 antibody or the antigen-binding fragment thereof. Examples of the isolation or purification method include methods using solubility such as salting-out and the solvent precipitation method, methods using the difference in molecular weight such as dialysis, ultrafiltration, and gel filtration, methods using an electric charge such as ion exchange chromatography and hydroxylapatite chromatography, methods using specific affinity such as affinity chromatography, methods using the difference in hydrophobicity such as reverse phase high performance liquid chromatography, and methods using the difference in the isoelectric point such as isoelectric focusing phoresis. Preferably, the antibody accumulated in a culture supernatant can be purified by various chromatographies, for example, column chromatography using Protein A column or Protein G column.

The anti-human Tie2 antibody or the antigen-binding fragment thereof of the present invention also includes an anti-human Tie2 antibody or an antigen-binding fragment thereof produced by the method for producing the anti-human Tie2 antibody or the antigen-binding fragment thereof of the present invention.

<Pharmaceutical Composition of the Present Invention>

The pharmaceutical compositions of the present invention include a pharmaceutical composition comprising the anti-human Tie2 antibody or the antigen-binding fragment thereof of the present invention and pharmaceutically acceptable excipients. The pharmaceutical composition of the present invention can be prepared by a method being generally used with excipients being generally used in the field, that is, excipients for medicine or carriers for medicine. Examples of dosage forms of the pharmaceutical compositions include parenteral drug such as an injection drug and a drip infusion drug, and these can be administered by intravenous administration, subcutaneous administration, intraocular administration, or the like. In drug preparation, excipients, carriers, and additives in accordance with the dosage forms can be used within the pharmaceutically acceptable range.

The pharmaceutical compositions of the present invention may comprise plural kinds of anti-human Tie2 antibodies or antigen-binding fragments thereof of the present invention. For example, the present invention includes a pharmaceutical composition comprising an antibody or an antigen-binding fragment thereof, which does not undergo posttranslational modification and an antibody or an antigen-binding fragment thereof derived from posttranslational modification of the antibody or the antigen-binding fragment thereof.

In one embodiment, the pharmaceutical composition of the present invention comprising an anti-human Tie2 antibody or an antigen-binding fragment thereof, includes a pharmaceutical composition as described below.

A pharmaceutical composition comprising an anti-human Tie2 antibody or an antigen-binding fragment thereof, in which the anti-human Tie2 antibody or the antigen-binding fragment thereof comprises four heavy chain variable regions and four light chain variable regions, the heavy chain variable region consists of the amino acid sequence of the amino acid numbers 1 to 122 of SEQ ID NO: 2, the light chain variable region consists of the amino acid sequence of the amino acid numbers 1 to 113 of SEQ ID NO: 4, the one heavy chain variable region and the one light chain variable region constitute one antigen-binding site, and the antibody or the antigen-binding fragment thereof comprises four antigen-binding sites, and an antibody or an antigen-binding fragment thereof derived from posttranslational modification of the antibody or the antigen-binding fragment thereof.

In one embodiment, the pharmaceutical composition comprising the anti-human Tie2 antibody of the present invention includes the pharmaceutical composition as described below.

A pharmaceutical composition comprising an anti-human Tie2 antibody which is an anti-human Tie2 antibody and an antibody formed by posttranslational modification of the antibody, comprising two heavy chains and four light chains, in which each heavy chain comprises two structures consisting of a heavy chain variable region consisting of the amino acid sequence of the amino acid numbers 1 to 122 of SEQ ID NO: 2 and a CH1 region, a CH2 region, and a CH3 region, and the C terminus of one of the structures is linked to the N terminus of the other structure through a linker, and each light chain comprises a light chain variable region consisting of the amino acid sequence of the amino acid numbers 1 to 113 of SEQ ID NO: 4, and a light chain constant region, and the antibody comprises four antigen-binding sites, and an antibody derived from posttranslational modification of the antibody.

The pharmaceutical compositions of the present invention also include a pharmaceutical composition comprising an antibody in which lysine of the C terminus of the heavy chain is deleted, an antibody or an antigen-binding fragment thereof with post-translational modification to N terminal, an antibody in which lysine of the C terminus of the heavy chain is deleted and posttranslation modification to N terminal is made, and/or an antibody which has lysine in the C terminus of the heavy chain and does not have post-translational modification to N terminal.

In one embodiment, the pharmaceutical composition of the present invention comprising an anti-human Tie2 antibody includes a pharmaceutical composition comprising at least two kinds of anti-human Tie2 antibodies selected from (1) to (4) below.

(1) An anti-human Tie2 antibody comprising two heavy chains consisting of the amino acid sequence of the amino acid numbers 1 to 678 of SEQ ID NO: 2 and four light chains consisting of the amino acid sequence shown by SEQ ID NO: 4.

(2) An anti-human Tie2 antibody comprising two heavy chains consisting of the amino acid sequence of SEQ ID NO: 2 in which glutamic acid of amino acid number 1 is modified to pyroglutamic acid and four light chains consisting of the amino acid sequence shown by SEQ ID NO: 4.

(3) An anti-human Tie2 antibody comprising two heavy chains consisting of the amino acid sequence of the amino acid numbers 1 to 678 of SEQ ID NO: 2 in which glutamic acid of amino acid number 1 is modified to pyroglutamic acid and four light chains consisting of the amino acid sequence shown by SEQ ID NO: 4.

(4) An anti-human Tie2 antibody comprising two heavy chains consisting of the amino acid sequence shown by SEQ ID NO: 2 and four light chains consisting of the amino acid sequence shown by SEQ ID NO: 4.

In one embodiment, the pharmaceutical composition of the present invention comprising an anti-human Tie2 antibody includes a pharmaceutical composition comprising at least two kinds of anti-human Tie2 antibodies selected from (1) to (4) below.

(1) An anti-human Tie2 antibody comprising two heavy chains consisting of the amino acid sequence of the amino acid numbers 1 to 678 of SEQ ID NO: 6 and four light chains consisting of the amino acid sequence shown by SEQ ID NO: 4.

(2) An anti-human Tie2 antibody comprising two heavy chains consisting of the amino acid sequence of SEQ ID NO: 6 in which glutamic acid of amino acid number 1 is modified to pyroglutamic acid and four light chains consisting of the amino acid sequence shown by SEQ ID NO: 4.

(3) An anti-human Tie2 antibody comprising two heavy chains consisting of the amino acid sequence of the amino acid numbers 1 to 678 of SEQ ID NO: 6 in which glutamic acid of amino acid number 1 is modified to pyroglutamic acid and four light chains consisting of the amino acid sequence shown by SEQ ID NO: 4.

(4) An anti-human Tie2 antibody comprising two heavy chains consisting of the amino acid sequence shown by SEQ ID NO: 6 and four light chains consisting of the amino acid sequence shown by SEQ ID NO: 4.

In one embodiment, the pharmaceutical composition of the present invention comprising an anti-human Tie2 antibody includes a pharmaceutical composition comprising at least two kinds of anti-human Tie2 antibodies selected from (1) to (4) below.

(1) An anti-human Tie2 antibody comprising two heavy chains consisting of the amino acid sequence of the amino acid numbers 1 to 678 of SEQ ID NO: 8 and four light chains consisting of the amino acid sequence shown by SEQ ID NO: 4.

(2) An anti-human Tie2 antibody comprising two heavy chains consisting of the amino acid sequence of SEQ ID NO: 8 in which glutamic acid of amino acid number 1 is modified to pyroglutamic acid and four light chains consisting of the amino acid sequence shown by SEQ ID NO: 4.

(3) An anti-human Tie2 antibody comprising two heavy chains consisting of the amino acid sequence of the amino acid numbers 1 to 678 of SEQ ID NO: 8 in which glutamic acid of amino acid number 1 is modified to pyroglutamic acid and four light chains consisting of the amino acid sequence shown by SEQ ID NO: 4.

(4) An anti-human Tie2 antibody comprising two heavy chains consisting of the amino acid sequence shown by SEQ ID NO: 8 and four light chains consisting of the amino acid sequence shown by SEQ ID NO: 4.

In one embodiment, the pharmaceutical composition of the present invention comprising an anti-human Tie2 antibody includes a pharmaceutical composition comprising at least two kinds of anti-human Tie2 antibodies selected from (1) to (4) below.

(1) An anti-human Tie2 antibody comprising two heavy chains consisting of the amino acid sequence of the amino acid numbers 1 to 675 of SEQ ID NO: 10 and four light chains consisting of the amino acid sequence shown by SEQ ID NO: 4.

(2) An anti-human Tie2 antibody comprising two heavy chains consisting of the amino acid sequence of SEQ ID NO: 10 in which glutamic acid of amino acid number 1 is modified to pyroglutamic acid and four light chains consisting of the amino acid sequence shown by SEQ ID NO: 4.

(3) An anti-human Tie2 antibody comprising two heavy chains consisting of the amino acid sequence of the amino acid numbers 1 to 675 of SEQ ID NO: 10 in which glutamic acid of amino acid number 1 is modified to pyroglutamic acid and four light chains consisting of the amino acid sequence shown by SEQ ID NO: 4.

(4) An anti-human Tie2 antibody comprising two heavy chains consisting of the amino acid sequence shown by SEQ ID NO: 10 and four light chains consisting of the amino acid sequence shown by SEQ ID NO: 4.

In one embodiment, the pharmaceutical composition of the present invention comprising an anti-human Tie2 antibody or an antigen-binding fragment thereof also includes the pharmaceutical composition as described below.

A pharmaceutical composition comprising an anti-human Tie2 antibody comprising two heavy chains consisting of the amino acid sequence shown by SEQ ID NO: 2 and four light chains consisting of the amino acid sequence shown by SEQ ID NO: 4, an anti-human Tie2 antibody comprising two heavy chains consisting of the amino acid sequence of the amino acid numbers 1 to 678 of SEQ ID NO: 2 and four light chains consisting of the amino acid sequence shown by SEQ ID NO: 4, and a pharmaceutically acceptable excipient.

The amount of the anti-human Tie2 antibody or the antigen-binding fragment thereof of the present invention added in formulation varies depending on the degree of symptoms and the age of a patient, a dosage form of a preparation to be used, the binding titer of an antibody, or the like, and for example, an amount added of approximately 0.001 mg/kg to 100 mg/kg can be used.

The pharmaceutical composition of the present invention can be used as an agent for preventing or treating blood vessel-related diseases, for example, diabetic retinopathy, diabetic macular edema, sepsis, acute hepatic disorders, acute renal disorders, acute pulmonary disorders, systemic inflammatory reaction syndrome, peripheral arterial occlusive disease, or critical limb ischemia.

The present invention includes a pharmaceutical composition for preventing or treating diabetic macular edema, diabetic retinopathy, or critical limb ischemia, comprising the anti-human Tie2 antibody of the present invention. Further, the present invention includes a method for preventing or treating diabetic macular edema, diabetic retinopathy, or critical limb ischemia, comprising administering a therapeutically effective amount of the anti-human Tie2 antibody of the present invention. Further, the present invention includes the anti-human Tie2 antibody of the present invention for use in preventing or treating diabetic macular edema, diabetic retinopathy, or critical limb ischemia. In addition, the present invention includes use of the anti-human Tie2 antibody of the present invention for preparation of a pharmaceutical composition for preventing or treating diabetic macular edema, diabetic retinopathy, or critical limb ischemia.

<Fusion Antibody and Modification Antibody>

Any person skilled in the art can prepare a fusion antibody in which an antibody or an antigen-binding fragment thereof is fused with another peptide or protein, and can also prepare a modification antibody to which a modifying agent is bound, using a known method in the field. The anti-human Tie2 antibody or the antigen-binding fragment thereof of the present invention includes the antibody and the antigen-binding fragment thereof in the form of such a fusion or a modification. For example, the anti-human Tie2 antibody or an antigen-binding fragment thereof, comprising four heavy chain variable regions and four light chain variable regions, in which the heavy chain variable region consists of the amino acid sequence of the amino acid numbers 1 to 122 of SEQ ID NO: 2, the light chain variable region consists of the amino acid sequence of the amino acid numbers 1 to 113 of SEQ ID NO: 4, the one heavy chain variable region and the one light chain variable region constitute one antigen-binding site, and the antibody or the antigen-binding fragment thereof comprises four antigen-binding sites, includes an anti-human Tie2 antibody or an antigen-binding fragment thereof fused with another peptide or protein, and an anti-human Tie2 antibody or an antigen-binding fragment thereof having a modifying agent bound thereto. The other peptide or protein for use in the fusion is not particularly limited as long as the antibody or the antigen-binding fragment thereof of the present invention as a fusion has binding activity to a human Tie2, and examples thereof include human serum albumin, various tag peptides, artificial helix motif peptides, maltose-binding protein, a glutathione S transferase, various toxins, and other peptides or proteins capable of promoting multimerization. The modifying agent for use in the modification is not particularly limited as long as the antibody or an antigen-binding fragment thereof of the present invention as a modification antibody has binding activity to a human Tie2, and examples thereof include polyethylene glycol, sugar chains, phospholipids, liposomes, and low-molecular compounds.

The present invention has been described and specific examples referred to for better understanding will be provided, but these are merely examples and the present invention is not limited thereto.

EXAMPLES

With regard to parts using commercially available kits or reagents, the experiments were carried out according to the described protocol unless specifically otherwise noted. For the sake of convenience, a concentration in mol/L is represented by M. For example, a 1 M aqueous sodium oxide solution means a 1 mol/L aqueous sodium oxide solution.

Example 1: Preparation of Hybridoma Producing Anti-Human Tie2 Antibody

Antibody was prepared by using the "VelocImmune" (VelocImmune antibody technology: Regeneron, Inc. (U.S. Pat. No. 6,596,541))—human monoclonal antibody developing technology—mouse. A recombinant human Tie2-Fc chimeric protein (R&D, 313-TI-100) was injected into the VelocImmune mouse, together with an adjuvant for causing an immune reaction, so as to perform immunization. According to an ordinary method, the lymph node of the immunized mouse was extracted, and the lymphocytes were collected and cell-fused with mouse-derived myeloma cell SP2/0 (ATCC: CRL-1581), thereby preparing a hybridoma. The hybridoma was monocloned and each clone was cultured in a CD Hybridoma Medium (Invitrogen) which is a serum-free culture medium. The antibody was purified from the obtained culture supernatant using a Protein G Column (GE Healthcare). The antibody obtained by using the VelocImmune technology is an antibody having a variable region of the human antibody and a constant region of the mouse antibody (also referred to a chimeric antibody).

Example 2: Cell ELISA Assay

In order to measure the antigen-binding activity of the antibody, the bindings of the antibody to a human Tie2, a monkey Tie2, a rat Tie2, and a mouse Tie2 were each evaluated by cell ELISA assay using a human Tie2-expressing CHO cell, a monkey Tie2-expressing CHO cell, a rat Tie2-expressing CHO cell, and a mouse Tie2-expressing CHO cell.

Example 3: Evaluation of Competitive Activity Using Modified Ang-1

In order to evaluate the Ang-2 competitive activity of the antibody, the inhibition of the binding of a modified Ang-1 (Proc. Natl. Acad. Sci., 2004, Vol. 101, pp. 5547-5552, also referred to as COMP-Ang1.) to Tie2 was evaluated. The COMP-Ang1 is a modified Ang-1 in which a site not involved in the binding to Tie2 is modified, and its competitive action against Ang-2 can be evaluated by evaluating the competitive action against COMP-Ang1 from the viewpoints that the binding capacity of COMP-Ang1 to Tie2 is maintained (Proc. Natl. Acad. Sci. 2004, Vol. 101, pp. 5547-5552), and Ang-1 and Ang-2 bind to the same site of Tie2 with the same level of affinity (Science, 1997, Vol. 277, pp. 55-60).

An expression vector of COMP-Ang1 was introduced into an HEK293 cell. The COMP-Ang1 was purified from a culture supernatant of the HEK293 cell, and biotin-labeled. The biotin-labeled COMP-Ang1 and the purified antibody obtained in Example 1 were mixed, and the mixture was added to a plate immobilized with a recombinant human Tie2-Fc chimeric protein. For the detection of the biotin-labeled COMP-Ang1 thus bound, a streptavidin-labeled HRP was used. A TMB color developing reagent (Dako, 51599) was added thereto and left to stand. Further, a 2 M sulfuric acid was then added thereto to stop the reaction and an absorbance at 450 nm was measured. In this manner, the competitive action of the antibody against the COMP-Ang1 was evaluated.

Example 4: Evaluation of Anti-Apoptotic Activity Using Human Tie2-Expressing BaF3 Cell A mouse pro-B cell strain BaF3 cell which stably expresses a human Tie2 (hereinafter also referred to as a human Tie2-expressing BaF3 cell) was prepared by introducing a plasmid containing a human Tie2 gene shown by SEQ ID NO: 21 to the cell by electroporation according to the method described in Immunity, 1998, Vol. 9, pp. 677-686. Thereafter, the anti-apoptotic activity of the antibody was evaluated using the same cell.

The human Tie2-expressing BaF3 cell was suspended in an RPMI1640 medium (Life Technologies) supplemented with 0.05% fetal bovine serum albumin at $2\times10^5$ cells/mL, and distributed in the amount of 80 μL per well in a 96-well plate for floating cells (Sumitomo Bakelite Co., Ltd., MS-8096R). Thereafter, 20 μL of the purified antibody obtained in Example 1 or Ang-1 was added thereto. After culturing for 72 hours in a $CO_2$ incubator set to 37° C., 50 μL of the cell suspension was transferred to a white 96-well plate (Nunc, 236108). According to an intracellular ATP quantification reagent CellTiter Glo Luminescent Cell Viability Kit (Promega), by adding 50 μL of a substrate solution diluted with an attached buffer to the cell suspension, the viability of the cell was measured, thereby evaluating anti-apoptotic activity.

From the results of Examples 2 to 4, antibodies having a binding activity to a human Tie2, a monkey Tie2, a rat Tie2, and a mouse Tie2, a COMP-Ang1 competitive activity, and anti-apoptotic activity to a human Tie2 were found. The purified antibody solution comprising an anti-human Tie2 antibody nominated as 2-16 which will be described later exhibited substantially the same anti-apoptotic activity as Ang-1 in Example 4, but the purified antibody solution comprising the mouse anti-human Tie2 antibody 15B8 (Patent Document 1) exhibited only approximately 60% of the maximum activity of the Ang-1.

Example 5: Analysis of Purified Antibody Solution Using Size Exclusion Chromatography and Electrophoresis The purified antibody solutions identified in Examples 2 to 4 above were analyzed by size exclusion chromatography. As a result, three fractions were detected from the respective purified antibody solutions. As a result of the analysis of the respective fraction solutions by electrophoresis, it was found that the respective fractions include monomers, dimers, trimers or higher-valent multimers of the antibodies, respectively.

Next, the respective fraction solutions were evaluated regarding the anti-apoptotic activity by the method shown in Example 4. As a result, in the fractions comprising the dimers and the fractions comprising the trimers or higher-valent multimers, potent anti-apoptotic activity was recognized. On the other hand, in the fraction comprising monomers from the respective antibodies, anti-apoptotic activity was substantially unrecognized. 15B8 was also analyzed by size exclusion chromatography as described above, and as a result, fractions showing dimers or higher-valent multimers were detected, but fractions comprising monomers were substantially undetected.

From the above, it was found that in any antibody identified in Examples 2 to 4, the fractions comprising the antibodies formed into dimers or higher-order multimers pertained potent anti-apoptotic activities. It is suggested that antibodies having four or higher valences have the strong anti-apoptotic activity through Tie2 activation as a dimer is a tetravalent antibody.

Example 6: Evaluation of Anti-Apoptotic Activity by Cross-Linking Antibody

From the investigations in Example 5, it is considered that the valence of the anti-human Tie2 antibody adjusted to be 4 or higher is important to induce the anti-apoptotic activity through Tie2. Thus, the anti-apoptotic activity of the anti-human Tie2 antibody which was multimerized by performing cross-linking with an anti-mouse IgG antibody was evaluated. As a cell, a human Tie2-expressing BaF3 cell and a human vascular endothelial cell HUVEC that endogenously expresses a human Tie2 were used.

The human Tie2-expressing BaF3 cell and HUVEC were cultured in an RPMI1640 medium and an EBM-2 serum-free medium (Lonza), respectively, to which an antibody solution comprising the anti-human Tie2 antibodies identified in Examples 2 to 4 had been added. An anti-mouse IgG antibody was added thereto to cross-link the antibodies. By employing CellTiter Glo Luminescent Cell Viability Assay, the viability of the cells was measured. By measuring the viability, the anti-apoptotic activity was evaluated.

As a result, it was found that the cross-linking antibody of the anti-human Tie2 antibody (chimeric antibody) nominated as 2-16 has a potent anti-apoptotic activity on the human Tie2.

Example 7: Sequencing of Bivalent Anti-Human Tie2 Antibody

A gene encoding the heavy and light chains of the antibody was cloned from a hybridoma producing the anti-human Tie2 antibody 2-16, and sequenced.

After sequencing the antibody, the framework region (FR) of the light and heavy chains of 2-16 was replaced with the FR of another human antibody in order to improve the physical properties and the stability of the antibody, thereby preparing a modified variable region of anti-human Tie2 antibody 2-16A2.

A gene encoding a signal sequence (Protein Engineering, 1987, Vol. 1, No. 6, pp. 499-505) and a human Igγ1 constant region gene (consisting of the base sequence of base numbers 367 to 1356 of SEQ ID NO: 11) were linked to the 5' side and the 3' side, respectively, of the heavy chain variable region gene of 2-16A2, and the heavy chain gene was inserted into a GS vector pEE6.4. Further, a gene encoding a signal sequence (Protein Engineering, 1987, Vol. 1, No. 6, pp. 499-505) and a constant region gene (consisting of the base sequence of base numbers 340 to 657 of SEQ ID NO: 3) of a human κ chain were connected to the 5' side and the 3' side, respectively, of the light chain variable region gene. This light chain gene was inserted into GS vector pEE12.4. The heavy chain gene sequence and the light chain gene sequence of the prepared antibody were analyzed using a sequencer.

The base sequence of the heavy chain of the fully human antibody of 2-16A2 (fully human 2-16A2) and the amino acid sequence encoded by the base sequence are shown by SEQ ID NOS: 11 and 12, respectively. Further, the base sequence of the light chain of the antibody and the amino acid sequence encoded by the base sequence are shown by SEQ ID NOS: 3 and 4, respectively. The variable region of the heavy chain shown by SEQ ID NO: 12 consists of the amino acid sequence of the amino acid numbers 1 to 122 of SEQ ID NO: 12, and the variable region of the light chain shown by SEQ ID NO: 4 consists of the amino acid sequence of the amino acid numbers 1 to 113 of SEQ ID NO: 4.

By using the GS vector as described above, into which the genes of the heavy chain and the light chain of the fully human 2-16A2 had each been inserted, the antibody expression was performed by using two types of methods, that is, transient expression and stably expression. With regard to transient expression, FreeStyle 293 cells (Invitrogen) cultured in a FreeStyle 293 Expression medium (Invitrogen) at about 1,000,000 cells/mL were transfected with both expression vectors of the heavy chain and the light chain as described above using a transfection kit, 293 Fectin (Invitrogen), and cultured for 5 days. Alternatively, Expi 293 cells (Invitrogen) cultured in an Expi 293 Expression medium (Invitrogen) at about 3,000,000 cells/mL were transfected by both expression vectors of the heavy chain and the light chain as described above using a transfection kit, Expi-Fectamine 293 Transfection kit (Invitrogen), and cultured for 7 days. Alternatively, CHO-K1SV cells (Lonza) cultured in a CD-CHO medium (Invitrogen) at about 10,000,000 cells/mL were transfected both expression vectors of the heavy chain and the light chain as described above using an electroporation method, and cultured for 7 days. The fully human antibody was purified from each of the culture supernatants using a Protein A column or a Protein G column (GE HealthCare). With regard to stable expression, the GS vector as described above, into which the genes of the heavy chain and the light chain of the antibody had been each inserted, was digested with restriction enzymes of NotI and PvuI, and ligated using a Ligation-Convenience Kit (NIPPONGENE) as a kit for ligation or a ligation reagent, Ligation high Ver. 2 (TOYOBO), thereby constructing a GS vector, into which both genes of the heavy chain and the light chain had been inserted. The antibody was expressed by transfection of the expression vector into the CHO-K1SV cells. The fully human antibody was purified from culture supernatant by a Protein A column, a Protein G column, or a MabSelect SuRe (GE Healthcare, 17-5438-02).

Example 8: Preparation of Tetravalent Anti-Human Tie2 Antibody

A tetravalent anti-human Tie2 antibody was prepared. The tetravalent antibody prepared in the present Example includes two heavy chains and four light chains. Each heavy chain comprises two structures consisting of a heavy chain variable region and a CH1 region, and further comprises a CH2 region, and a CH3 region, in which the C terminus of one structure consisting of the heavy chain variable region and the CH1 region is linked to the N terminus of the other structure through a linker. Each light chain comprises a light chain variable region and a light chain constant region. The format of the present tetravalent antibody is shown in FIG. 1.

A gene encoding a tetravalent anti-human Tie2 antibody heavy chain, in which the C terminus of a structure (consisting of the amino acid sequence of the amino acid numbers 1 to 220 of SEQ ID NO: 12) consisting of the heavy chain variable region and the CH1 region of the fully human 2-16A2 was linked to the N terminus of the fully human 2-16A2 heavy chain through a linker consisting of the amino acid sequence shown by SEQ ID NO: 13, was prepared. A gene encoding a signal sequence (Protein Engineering, 1987, Vol. 1, No. 6, pp. 499-505) was linked to the 5' side of the prepared heavy chain gene, and inserted into a GS vector pEE6.4. The above heavy chain vector and the GS vector pEE12.4, into which the light chain gene of the fully human antibody 2-16A2 prepared in Example 7 had been inserted, were combined to prepare a tetravalent anti-human Tie2 antibody using the same antibody expression and purification method as described in Example 7. The tetravalent anti-human Tie2 antibody is referred to as TIE-1-Igγ1-WT.

A gene encoding a tetravalent anti-human Tie2 antibody heavy chain having a constant region of the heavy chain of TIE-1-Igγ1-WT substituted with a human Igγ4 constant region (consisting of the amino acid sequence of the amino acid numbers 123 to 220 of SEQ ID NO: 10, and consisting of the amino acid sequence of the amino acid numbers 350 to 676 of SEQ ID NO: 10) with amino acid mutations of S228P and L235E, was prepared. A gene encoding a signal sequence (Protein Engineering, 1987, Vol. 1, No. 6, pp. 499-505) was linked to the 5' side of the prepared heavy chain gene and inserted into a GS vector pEE6.4. The above heavy chain vector and the GS vector pEE12.4, into which the light chain gene of the fully human 2-16A2 prepared in Example 7 had been inserted, were combined to prepare a tetravalent anti-human Tie2 antibody using the same antibody expression and purification method as described in Example 7. The tetravalent anti-human Tie2 antibody with IgG4 is referred to as TIE-1-Igγ4-PE.

The base sequence of the heavy chain of TIE-1-Igγ1-WT and the amino acid sequence encoded by the base sequence are shown by SEQ ID NOS: 7 and 8, respectively. The base sequence of the heavy chain of TIE-1-Igγ4-PE and the amino acid sequence encoded by the base sequence are shown by SEQ ID NOS: 9 and 10, respectively. The light chain of both the antibodies are the same as the light chain of the fully human antibody 2-16A2, and the base sequence of the light chain and the amino acid sequence encoded by the base sequence of the antibody are shown by SEQ ID NOS: 3 and 4, respectively.

By using the same method, a tetravalent anti-human Tie2 antibody, in which amino acid variations of L234A, L235A, and P331S had been introduced to the constant region of the heavy chain of TIE-1-Igγ1-WT (referred to as TIE-1-Igγ1-LALA), and a tetravalent anti-human Tie2 antibody, in which amino acid variations of L234A, L235A, P331S, and I253A had been introduced to the constant region of the heavy chain of TIE-1-Igγ1-WT (referred to as TIE-1-Igγ1-I253A), were prepared.

The base sequence of the heavy chain and the amino acid sequence encoded by the base sequence of TIE-1-Igγ1-LALA are shown by SEQ ID NOS: 1 and 2, respectively. The base sequence of the heavy chain and the amino acid sequence encoded by the base sequence of TIE-1-Igγ1-I253A are shown by SEQ ID NOS: 5 and 6, respectively. The light chains of both the antibodies were the same as the light chain of the fully human 2-16A2, and the base sequence of the light chain and the amino acid sequence encoded by the base sequence of the antibody were shown by SEQ ID NOS: 3 and 4, respectively.

The variable regions of the heavy chains of four kinds of the tetravalent anti-human Tie2 antibodies shown by SEQ ID NOS: 2, 6, 8, and 10 are common and consist of the amino acid sequence of the amino acid numbers 1 to 122 of SEQ ID NO: 2. The CDR1, CDR2, and CDR3 of the heavy chain variable regions each consist of the amino acid sequence of the amino acid numbers 31 to 35, 50 to 66, and 99 to 111 of SEQ ID NO: 2.

The variable regions of the light chains of four kinds of the tetravalent anti-human Tie2 antibodies shown by SEQ ID NO: 4 each consist of the amino acid sequence of the amino acid numbers 1 to 113 of SEQ ID NO: 4. The CDR1, CDR2, and CDR3 of the light chain variable regions consist of the amino acid sequence of the amino acid numbers 24 to 39, 55 to 61, and 94 to 102 of SEQ ID NO: 4, respectively.

As a result of the analysis of the amino acid modifications of the purified TIE-1-Igγ1-LALA, it was found that in most of the purified antibodies, deletion of lysine at the C terminus of the heavy chain occurred.

In addition, by using the same method, tetravalent anti-human Tie2 antibodies, in which with respect to TIE-1-Igγ1-WT and TIE-1-Igγ4-PE, the linker (consisting of the amino acid sequence shown by SEQ ID NO: 13) was substituted with other linkers (four kinds of linkers consisting of the amino acid sequences shown by SEQ ID NOS: 17 to 20 with respect to TIE-1-Igγ1-WT, and seven kinds of linkers consisting of the amino acid sequences shown by SEQ ID NOS: 14 to 20 with respect to TIE-1-Igγ4-PE), were prepared (total 11 kinds). A linker having a length of 7 amino acids (a linker consisting of the amino acid sequence shown by SEQ ID NO: 13) to a linker having a length of 64 amino acids (a linker consisting of the amino acid sequence shown by SEQ ID NO: 20) were investigated.

As a result of the investigations on TIE-1-Igγ1-WT, TIE-1-Igγ4-PE and 11 kinds of antibodies in which the linker were substituted, it was found that all of the anti-human Tie2 antibodies had substantially the same anti-apoptotic activities in accordance with the method of Example 4.

Example 9: Evaluation of Anti-Apoptotic Action of Bivalent Anti-Human Tie2 Antibody and Tetravalent Anti-Human Tie2 Antibody From the results of Example 5, it was suggested that a tetravalent or higher-valent antibody has a potent anti-apoptotic activity through a human Tie2 activation. Thus, the efficacy of the bivalent anti-human Tie2 antibody was compared with that of the tetravalent anti-human Tie2 antibody by measuring the anti-apoptotic action on the human Tie2-expressing BaF3 cell as an index.

According to the method of Example 4, the anti-apoptotic action of the fully human 2-16A2 which is a bivalent antibody and TIE-1-Igγ1-WT which is a tetravalent antibody was evaluated by using the human Tie2-expressing BaF3 cell. The fully human 2-16A2 and TIE-1-Igγ1-WT which were tested antibodies were purified by MabSelect SuRe and fractionized into monomer fractions by size exclusion chromatography, thereby acquiring monomer purities of 99.98% and 99.74%, respectively. The respective antibodies were diluted with phosphate buffer saline (PBS) to from 5 ng/mL to 5000 ng/mL at an about 3-fold common ratio through seven steps, and added in the amount of 20 μL per well. As a control, PBS, or Ang-1 diluted with PBS (R&D, 923-AN-025/CF, a final concentration of 1 ng/mL to 1000 ng/mL, diluted at an about 3-fold common ratio through 7 steps) had been added instead of the test antibodies, were prepared, respectively. For calculation of the anti-apoptotic activity at each of the concentrations of the test antibodies, the measured value of the well to which PBS had been added instead of the test antibody was set to 0%, and the average value of the measured values of the wells to which Ang-1 had been added at the concentration of 300 ng/mL and 1000 ng/mL, respectively, instead of the test antibodies, was set to 100%. The $EC_{50}$ value of the test antibody was calculated by analyzing the calculated anti-apoptotic activity using Sigmoid-Emax model non-linear regression analysis.

TABLE 1

Anti-Apoptotic Activities of Bivalent Anti-Human Tie2 Antibody and Tetravalent Anti-Human Tie2 Antibody

|  | $EC_{50}$ value | Maximum activity of anti-apoptotic activities |
| --- | --- | --- |
| TIE-1-Igγ1-WT | 7.10 ng/mL | 104% |
| Fully human 2-16A2 | 37.6 ng/mL | 22% |

As a result, it was found that TIE-1-Igγ1-WT which is a tetravalent antibody has potent anti-apoptotic action. From the above, it was found that the tetravalent antibody has a superior anti-apoptotic activity, as compared with the bivalent antibody.

Example 10: Evaluation of Vascular Permeability Inhibitory Action of Bivalent Anti-Human Tie2 Antibody and Tetravalent Anti-Human Tie2 Antibody in Rat A mustard oil-induced vascular permeability model is a model with a modification applied to a Miles assay (J. Physiol., 1952, Vol. 118, pp. 228-257) which has been widely used as a plasma leakage evaluation system, and it has been reported that Ang-1 inhibits the vascular hyperpermeability in the present model (Nature Medicine, 2000, Vol. 6, pp. 460-463). Accordingly, in order to compare the vascular permeability inhibitory action of the bivalent anti-human Tie2 antibody with that of the tetravalent anti-human Tie2 antibody, the fully human 2-16A2 and TIE-1-Igγ1-WT were evaluated using the present model.

The fully human 2-16A2 or TIE-1-Igγ1-WT diluted with PBS was subcutaneously administered to an SD rat (Male, 4-5-week-old, Charles River Laboratories Japan, Inc.). The treated groups were set as follows.

[Treated Group (6 Rats Per Group)]
Vehicle Group:
Group to which PBS instead of the antibody was administered
Fully human 2-16A2 administration group:
Group to which the fully human 2-16A2 was administered (0.3 mg/kg)
TIE-1-Igγ1-WT administration group:
Group to which TIE-1-Igγ1-WT was administered (0.3 mg/kg)

At 48 hours after the administration of the antibody, an Evans Blue dye dissolved in physiological saline (45 mg/kg, Sigma-Aldrich Corporation, E2129) was intravenously administered, immediately allyl isothiocyanate (also referred to as a mustard oil, Nacalai Tesque, Inc., 01415-92) diluted with a mineral oil (Sigma-Aldrich Corporation, M8410) of 5% was applied onto one ear, while the mineral oil was applied onto the contralateral ear, in the amount of 20 μL. After 30 minutes, both of the ears were sampled, weighed, then immersed in 1 mL of formamide, and incubated at 70° C. overnight to extract the Evans Blue dye in the ear tissue. The Evans Blue dye concentration was determined from the absorbance (a measurement wavelength of 620 nm and a control wavelength of 740 nm) of the extract to calculate the amount of the Evans Blue dye in the extract. Thereafter, by dividing the amount of the Evans Blue dye by the weight of the ear, the dye leakage amount per weight of the ear was calculated. A value obtained by subtracting the leakage amount of the Evans Blue dye of the ear having the mineral oil applied thereon from the leakage amount of the Evans Blue dye of the ear having the mustard oil applied thereon in the same individual was calculated as a final leakage amount of the Evans Blue dye of each individual. The leakage amount of the Evans Blue dye was used as an index of vascular permeability. The results are shown in FIG. 2.

The mean value and the standard error of each group were determined. A Student t-test was used to determine a significant difference between the vehicle group and each group to which an antibody had been administered. A case with $p<0.05$ was intended to indicate that there was a significant difference.

Figure 2:
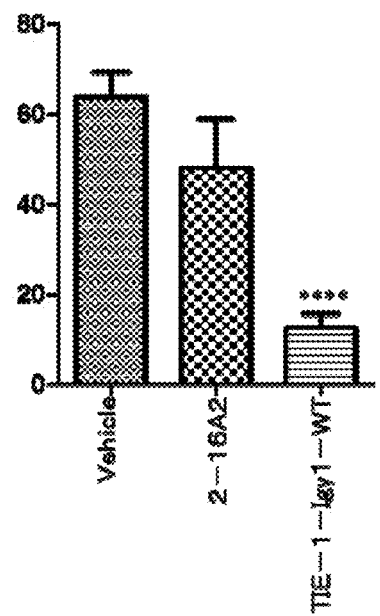
FIG. 2 shows the vascular permeability inhibitory action of the fully human 2-16A2 and TIE-1-Igγ1-WT in a rat model with vascular permeability. The vertical axis indicates the amount of leakage of an Evans Blue dye (****: $p<0.0001$ vs a vehicle group).

As shown in FIG. 2, compared with a vehicle group, the fully human 2-16A2 which is a bivalent antibody did not inhibit the dye leakage, whereas TIE-1-Igγ1-WT which is a tetravalent antibody significantly inhibited the dye leakage. It was found that TIE-1-Igγ1-WT which is a tetravalent antibody inhibited vascular hyperpermeability. From above, it was found that the tetravalent antibody has a superior vascular hyperpermeability inhibitory action, as compared with the bivalent antibody.

From the results of Examples 9 and 10, it was found that the tetravalent anti-Tie2 antibody strongly induced an action through Tie2.

(Example 11: Evaluation of Anti-Apoptotic Action of Tetravalent Anti-Human Tie2 Antibody (2))

For TIE-1-Igγ1-LALA and TIE-1-Igγ1-I253A, according to the method of Example 9, the anti-apoptotic activity of the antibody on the human Tie2-expressing BaF3 cell was evaluated. In the same concentration range as in Example 9, evaluation of each tetravalent anti-human Tie2 antibody was carried out. In this regard, when the average value of the measured values of the wells, to which each of 100 ng/mL, 300 ng/mL, and 1000 ng/mL of Ang-1 had been added, was taken as 100%, the $EC_{50}$ value and the maximum activity of the anti-apoptotic activity of each antibody were evaluated.

TABLE 2

Anti-Apoptotic Activity of Each Tetravalent Anti-Human Tie2 Antibody

|  | $EC_{50}$ value | Maximum activity of anti-apoptotic activities |
| --- | --- | --- |
| TIE-1-Igγ1-LALA | 3.65 ng/mL | 88% |
| TIE-1-Igγ1-I253A | 5.06 ng/mL | 94% |

As a result, it was found that both the TIE-1-Igγ1-LALA and the TIE-1-Igγ1-I253A exhibited substantially equivalent anti-apoptotic activity as Ang-1.

Reference Example 1: Evaluation of Anti-Apoptotic Action of 15B8

For 15B8, according to the method of Example 9, the anti-apoptotic activity on the human Tie2-expressing BaF3 cell was evaluated. Evaluation of 15B8 (Patent Document 1) was carried out in the same antibody concentration range as in Example 9. Evaluation of Ang-2 (R&D, 623-AN-025) was carried out in the same manner as that for Ang-1. In this regard, when the average value of the measured values of the wells, to which 1000 ng/mL of Ang-1 had been added, was taken as 100%, the $EC_{50}$ value and the maximum activity of the anti-apoptotic activity were evaluated.

TABLE 3

| Anti-Apoptotic Activity of 15B8 | | |
|---|---|---|
| | $EC_{50}$ value | Maximum activity of anti-apoptotic activities |
| 15B8 | 26.6 ng/mL | 64% |
| Ang-2 | 39.3 ng/mL | 67% |

As a result, it was found that the anti-apoptotic activity of 15B8 was about 64% of Ang-1 and had substantially equivalent anti-apoptotic activity as Ang-2.

As combined with the results of Example 11, it was found that TIE-1-Igγ1-LALA exhibited substantially equivalent anti-apoptotic activity as Ang-1, whereas 15B8 exhibited substantially equivalent partial anti-apoptotic activity as Ang-2.

Example 12: Evaluation of Binding Activity of TIE-1-Igγ1-LALA to Tie2

For TIE-1-Igγ1-LALA, the binding activities to each species Tie2 proteins were evaluated. A recombinant human Tie2-Fc chimeric protein (R&D, 313-TI-100), a recombinant monkey Tie2-Fc chimeric protein (Sino Biological Inc., 90292-C02H), a recombinant rat Tie2-Fc chimeric protein (R&D, 3874-T2-100), or a recombinant mouse Tie2-Fc chimeric protein (R&D, 762-T2-100) was prepared in PBS at 1 µg/mL, added to a white Maxisorp 384-well plate (Nunc, 460372) in the amount of 20 µL per well, and incubated at 4° C. overnight to perform immobilization. The next day, the immobilized solution was removed, and 20% Blocking One (Nacalai Tesque Inc., 03953-95)-containing Tris Buffer Saline (TBS)—0.05% Tween (Wako, 310-7375) (hereinafter referred to as a TBS-T solution) was added thereto in the amount of 50 µL per well, and left to stand at room temperature for 1 hour. TIE-1-Igγ1-LALA as a test antibody was diluted with a TBS-T solution containing 5% Blocking One from 0.03 ng/mL to 100 ng/mL at an about 3-fold common ratio through 8 steps, and added in the amount of 20 µL per well. As a control, a well to which a TBS-T solution had been added instead of the test antibody was prepared. The resultant was incubated at room temperature for 1.5 hours, and then washed with a TBS-T solution. As a secondary antibody, a biotin-labeled anti-human kappa light chain antibody (Immuno-Biological Laboratories Co., Ltd., 17249), which had been diluted to 0.1 µg/mL with a TBS-T solution containing 5% Blocking One, was added thereto in the amount of 20 µL per well. The resultant was incubated at room temperature for 1 hour and then washed with a TBS-T solution, and alkaline phosphatase-labeled streptavidin (Thermo Fisher Scientific Inc., 21324), which had been diluted to 0.1 µg/mL with 5% Blocking One-containing TBS-T solution, was added thereto in the amount of 20 µL per well. The resultant was incubated at room temperature for 1 hour and then washed with a TBS-T solution, and Chemiluminescent Ultra Sensitive AP Microwell and/or Membrane Substrate (450 nm) (BioFX, APU4-0100-01), which had been 5-fold diluted with 1 mM $MgCl_2$-containing 20 mM TBS (pH 9.8) as a substrate, was added thereto in the amount of 20 µL. The resultant was incubated at room temperature for 30 minutes, and then the chemiluminescence thereof was measured by an EnVision multi-label counter (PerkinElmer, Inc.). The $EC_{50}$ value of the test antibody was calculated by analyzing the calculated binding activity using Sigmoid-Emax model non-linear regression.

TABLE 4

| Binding Activity of TIE-1-Igγ1-LALA | | | | |
|---|---|---|---|---|
| | $EC_{50}$ value (ng/mL) | | | |
| | Human | Monkey | Rat | Mouse |
| TIE-1-Igγ1-LALA | 0.565 | 0.545 | 0.633 | 0.696 |

As a result, it was found that TIE-1-Igγ1-LALA has substantially the same high binding activity as a human Tie2, a monkey Tie2, a rat Tie2, and a mouse Tie2.

Reference Example 2: Evaluation of Binding Activity of 15B8 to Tie2

According to the method of Examples 12, the binding activities of 15B8 to each species Tie2 proteins were evaluated. In this regard, the absorbance at 450 nm was measured using an HRP-labeled anti-mouse kappa light chain antibody (SouthernBiotech, 1050-05) as a second antibody, a TMB color development reagent as a substrate, and an ARVO multi-label reader (PerkinElmer Inc.) as a measuring apparatus. In addition, 15B8 antibody concentration was adjusted to be from 1000 ng/mL to 0.3 ng/mL at an about 3-fold common ratio (diluted through eight steps), as a test antibody. The $EC_{50}$ value of the test antibody was calculated by analyzing the calculated binding activity using Sigmoid-Emax model non-linear regression (Table 5).

TABLE 5

| Binding Activity of 15B8 | | | | |
|---|---|---|---|---|
| | $EC_{50}$ value (ng/mL) | | | |
| | Human | Monkey | Rat | Mouse |
| 15B8 | 218.7 | 224.3 | >1000 | >1000 |

As a result, it was observed that 15B8 had binding activity to a human Tie2 and a monkey Tie2, but it was found that 15B8 has low binding activity to a rat Tie2 and a mouse Tie2.

From the results of Example 12, it was observed that TIE-1-Igγ1-LALA had high binding activity to a human Tie2, a monkey Tie2, a rat Tie2, and a mouse Tie2 without a species difference therein. On the other hand, it was observed that 15B8 had a species difference in the binding activity. From the above, it was suggested that the human Tie2 epitope of TIE-1-Igγ1-LALA was different from the epitope of 15B8.

Example 13: Evaluation of Vascular Permeability Inhibitory Action of TIE-1-Igγ1-LALA in Rat According to the method of Example 10, the vascular permeability inhibitory action of TIE-1-Igγ1-LALA in rats was evaluated. In this regard, TIE-1-Igγ1-LALA was used as a test antibody, and the antibody dose was adjusted to be 0.1 mg/kg and 0.3 mg/kg. The results are shown in FIG. 3.

The mean value and the standard error of each group were determined. A Dunnett multiple comparison test was employed to determine a significant difference between the vehicle group and each group to which the antibody had been administrated. A case in which p<0.05 was intended to indicate that there was a significant difference.

Figure 3:
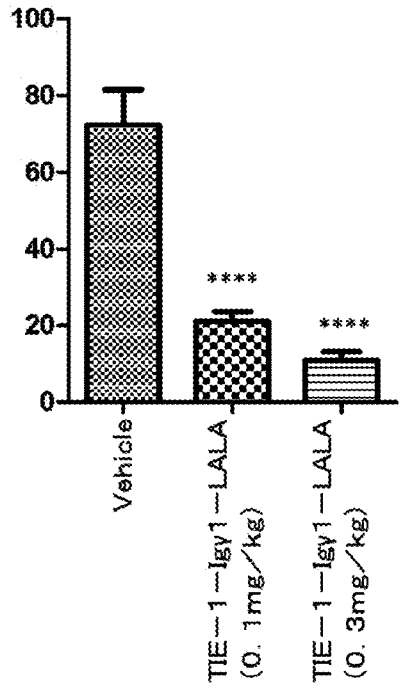
FIG. 3 shows the vascular permeability inhibitory action of TIE-1-Igγ1-LALA in a rat model with vascular permeability. The vertical axis indicates the amount of leakage of an Evans Blue dye (****: $p<0.0001$ vs a vehicle group).

As shown in FIG. 3, compared to the vehicle group, TIE-1-Igγ1-LALA significantly inhibited the dye leakage. From the above, it was found that TIE-1-Igγ1-LALA inhibited the vascular hyperpermeability.

Example 14: Retinal Edema Inhibitory Action in Mouse with Loss of Pericytes

In the retinal blood vessels of a patient with diabetic retinopathy, the loss of pericytes is one of characteristic lesions (Retina, 2013, Fifth edition, pp. 925-939). Although rat models with Streptozotocin-induced diabetes are widely used on diabetic retinopathy studies, there is a limitation in the usefulness of the models in the following aspects: a period of several months is taken until the loss of pericytes is observed, retinal microaneurysm which is thought to be caused by the loss of pericytes is not observed, the ratio of the pericytes to the endothelial cells is different from that of a human (Retina, 2013, Fifth edition, pp. 925-939), and apparent retinal edema is not observed (Diabetes Metab. J., 2013, Vol. 37, pp. 217-224). On the other hand, in a mouse having the retinal blood vessels with the loss of pericytes by administration of an anti-PDGF receptor β (PDGFR β) antibody, the lesions similar to those seen in diabetic retinopathy and diabetic macular edema, such as expansion of retinal blood vessel, retinal edema, and bleeding are observed, suggesting that the blood vessels are weakened like diabetic retinopathy and diabetic macular edema due to the loss of pericytes, although hyperglycemia is not observed (J. Clin. Invest., 2002, Vol. 110, pp. 1619-1628). Therefore, evaluation of the inhibitory action on retinal edema using a model with a condition showing the loss of pericytes, which is a characteristic lesion in a patient with diabetic retinopathy, is useful to evaluate the effectiveness on diabetic retinopathy and diabetic macular edema.

The retinal edema induced by loss of pericytes was prepared with a slight modification to the method reported in J. Clin. Invest., 2002, Vol. 110, pp. 1619-1628. That is, anti-PDGFR β monoclonal antibody 1B3 (WO 2008/130704) diluted with PBS was subcutaneously administered at 25 mg/kg to C57BL/6J mouse (Charles River Laboratories Japan, Inc.) on the $2^{nd}$ day after birth to induce the loss of pericytes in the retinal blood vessels.

[Treated Group]
Control Group (also referred to as Cont. group): 17 mice
Group to which an anti-PDGFR β antibody was not administered and PBS was administered
Vehicle group (also referred to as Veh. group): 24 mice
Group to which an anti-PDGFR β antibody was administered and PBS was administered, instead of TIE-1-Igγ1-LALA
TIE-1-Igγ1-LALA Group (0.1 mg/kg, 0.3 mg/kg, and 1 mg/kg): each 23 mice, 21 mice, and 21 mice
Group to which an anti-PDGFR β antibody was administered and each dose of TIE-1-Igγ1-LALA was administered At 90 minutes before administration of the anti-PDGFR β antibody, TIE-1-Igγ1-LALA diluted with PBS was subcutaneously administered at 0.1 mg/kg, 0.3 mg/kg and 1 mg/kg. At 1 week after administration of the antibody, retinal edema was evaluated. Specifically, the eyeball was extracted and fixed with 1% glutaraldehyde and 2.5% formalin containing solutions, and then a paraffin-embedded slice graft was prepared. Hematoxylin-eosin stained specimens were scanned to convert image data using a virtual slide scanner (NanoZoomer XR, Hamamatsu Photonics K. K.). In this model, retinal edema in the retinal nerve fiber layer (NFL) is reported (J. Clin. Invest., 2002, Vol. 110, pp. 1619-1628), thereby quantification of retinal edema was carried out by measuring the areas of NFL and adjacent retinal ganglion cell layer with an NPD view 2 (Hamamatsu Photonics K. K.). The results are shown in FIG. 4.

The mean value and the standard error of each group were determined. A Dunnett multiple comparison test was employed as an assay for determining a significant difference between the vehicle group and each group to which TIE-1-Igγ1-LALA had been administrated. A Student t-test was used as an assay for determining a significant difference between the Cont. group and the Veh. group. A case in which p<0.05 was intended to indicate that there was a significant difference in each case.

Figure 4:
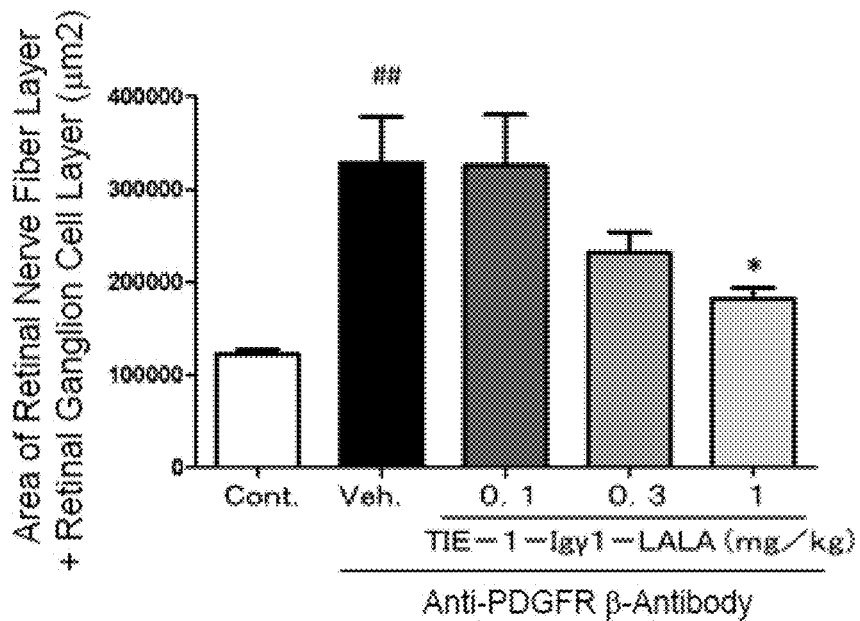
FIG. 4 shows the retinal edema inhibitory action of TIE-1-Igγ1-LALA in a mouse model with the loss of pericytes in the retinal blood vessel. The vertical axis indicates a sum of a retinal nerve fiber layer and a retinal ganglion cell layer (##: $p<0.005$ vs Cont. group, *: $p<0.05$ vs Veh. group).

As shown in FIG. 4, it was found that the TIE-1-Igγ1-LALA group (1 mg/kg) significantly inhibited the retinal edema having retinal blood vessels with the loss of pericytes as compared with the vehicle group. From the viewpoint that TIE-1-Igγ1-LALA inhibited the retinal edema caused by the retinal blood vessels with the loss of pericytes, it was suggested that TIE-1-Igγ1-LALA is effective on diabetic macular edema and diabetic retinopathy.

Example 15: Ischemia Limb Blood Flow Improving Action in Mouse with Hindlimb Ischemia The model with hindlimb ischemia is a model having ischemia in the hindlimb tissue induced by ligation and excision of the blood vessel in the hindlimb on one side, and is also a representative model for evaluating the improving the ischemia symptoms (J. Vasc. Surg., 2012, Vol. 56, pp. 1669-1679).

The inguinal region of the femoral artery and vein and the saphenous artery and vein on the left hindlimb were ligated in a 10-week C57BL/6J mouse (CLEA Japan, Inc.). Further, after the branch vessel therebetween was ligated, and the blood vessel between the ligated points was excised. Surgery was carried out under anesthesia with pentobarbital sodium (60 mg/kg, Tokyo Chemical Industry Co., Ltd.). At one week after excision of the vessel, the blood flow in the hindlimb was measured by using a laser Doppler perfusion imager MoorLDI2 (Moor Instruments Inc.) under anesthesia with pentobarbital. After confirming a decrease in the blood flow in the limb to be treated, the treated group was set as follows.

[Treated Group (10 Mice Per Group)]
Control Group:
Group to which PBS was Administered Instead of an Antibody
TIE-1-Igγ1-LALA Group (1 mg/kg):
Group to which TIE-1-Igγ1-LALA was Administered
TIE-1-Igγ1-LALA diluted with PBS was subcutaneously administered at 1 mg/kg, and the amount of skin blood flow of the normal limb and the ischemic limb at one week after administration of the antibody were measured. Specifically, pentobarbital sodium (60 mg/kg) was intraperitoneally administered, followed by placing on a heating plate, so as to measure the skin blood flow of the foot at 15 minutes after administration of anesthesia. The results of the blood flow measured by taking the bottom part of the foot as a region of interest (ROI), are shown in FIG. 5.

The mean value and the standard error of each group were determined. A Student t-test was used to determine a significant difference between the control group and the TIE-1-Igγ1-LALA group. A case in which p<0.05 is intended to indicate that there was a significant difference.

Figure 5:
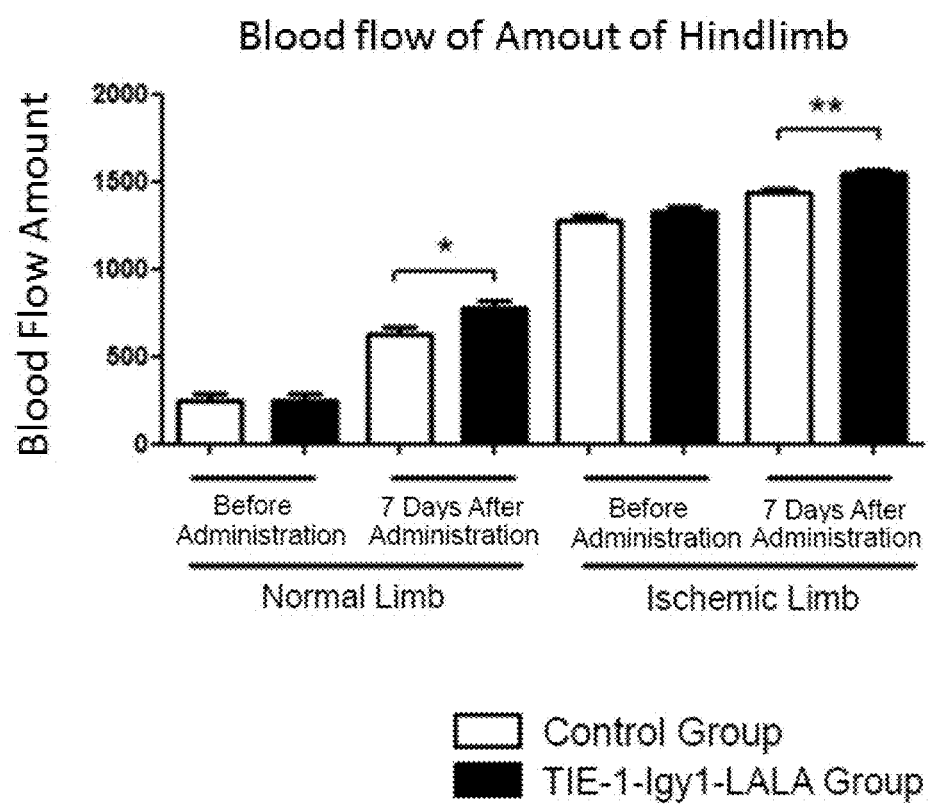
FIG. 5 shows the blood flow improving action of TIE-1-Igγ1-LALA in a mouse model with hindlimb ischemia. The vertical axis indicates the amount of blood flow. (*: $p<0.05$ vs control group, **: $p<0.01$ vs control group).

As shown in FIG. 5, it was found that compared with the control group, the TIE-1-Igγ1-LALA group significantly improved the amount of blood flow of the normal limb and the ischemic limb. Accordingly, the effectiveness of TIE-1-Igγ1-LALA on peripheral arterial diseases such as critical limb ischemia was suggested.

Example 16: Evaluation of Epitope of TIE-1-Igγ1-LALA: Hydrogen Deuterium Exchange Mass Spectrometry In order to identify the recognition epitope of TIE-1-Igγ1-LALA, Fab of the fully human 2-16A2 in Example 7 (hereinafter referred to as fully human 2-16A2-Fab) was prepared. Since the fully human 2-16A2-Fab has the same variable region as TIE-1-Igγ1-LALA, these antibodies recognize the same epitope. As an antigen, a human Tie2 protein consisting of the amino acid numbers 1 to 452 of Accession No. NP_000450.2 (hereinafter referred to as a human Tie2 (1-452)) was prepared. The amino acid sequence is the same site used when the Tie2 binding site of Ang-2 was indentified (Nat. Struct. Mol. Biol., Vol. 13, pp. 524-532).

Specifically, the fully human 2-16A2-Fab was prepared by combining a GS vector pEE6.4 in which a heavy chain gene encoding a structure (consisting of the amino acid sequence of the amino acid numbers 1 to 221 of SEQ ID NO: 12) consisting of the heavy chain variable region and the CH1 region of the fully human 2-16A2 was inserted, and the GS vector pEE12.4 in which a light chain gene of the fully human 2-16A2 was inserted, and using the same method as the expression method and the purification method for the antibody described in Example 7.

In order to obtain human Tie2 (1-452), first, human Tie2 (1-452) obtained by fusing human Fc (consisting of the amino acid sequence shown by SEQ ID NO: 23) with a thrombin recognition sequence (consisting of the amino acid sequence shown by SEQ ID NO: 22) as a linker (hereinafter referred to as a human Tie2 (1-452)-Fc chimeric protein) was prepared. Specifically, by inserting a gene encoding the human Tie2 (1-452)-Fc chimeric protein into a GS vector pEE12.4, and using the same expression method and the purification method described in Example 7, the human Tie2 (1-452)-Fc chimeric protein was prepared. Next, the prepared human Tie2 (1-452)-Fc chimeric protein was incubated with thrombin (GE Healthcare, 27-0846-01) at 22° C. for 16 hours to cut the Fc portion, and thrombin and human Fc were removed by Benzamidine Sepharose 4 Fast Flow (high sub) (GE Healthcare) and MabSelect SuRe, thereby preparing a human Tie2 (1-452).

For the purpose of indentifying the epitope site, hydrogen/deuterium exchange mass spectrometry (hereinafter referred to as H/D exchange mass spectrometry, Anal. Bioanal. Chem., 2010, Vol. 397, pp. 967-979) was carried out by using NanoAQUITY UPLC HDX Systems (Waters).

Specifically, the fully human 2-16A2-Fab and human Tie2 (1-452) mixed liquid (final concentration of 50 μM and 25 μM, respectively) was prepared using a 20 mM citric acid buffer (pH 6) containing 120 mM sodium chloride, and incubated at 37° C. overnight. As a control, a solution with only human Tie2 (1-452) was prepared using 20 mM citric acid buffer (pH 6) containing 120 mM sodium chloride. Thereafter, the solution was added to a PBS buffer solution prepared using deuterium water (Kanto Chemical Co., Inc.), and incubated for 20 seconds, 1 minute, 10 minutes, 60 minutes, and 120 minutes, respectively, and deuteration was carried out. Then, an aqueous solution (pH 2.5) containing 100 mM dithiothreitol (Nacalai Tesque) and 4 M guanidine hydrochloride (Wako Pure Chemical Industries, Ltd.) was added thereto at 0° C., and then digestion was carried out using a Pepsin Column (Proszyme (registered trademark) Immobilized Pepsin Cartridge, Applied Biosystems), and the peptide digested with a trap column (ACQUITY UPLC BEH C18 1.7 μm VanGuard Pre-Column, Waters) was captured. Then, separation was carried out by reverse phase chromatography using C18 column (AQUITY UPLC BEH C18 1.7 μm, Waters) and the molecular weight was measured with a mass spectrometer (SynaptG2-Si, Waters). The centroid value of the isotopic distribution of all the detected peptides was calculated, and compared with centroid value of the isotopic distribution of only human Tie2 (1-452) which had undergone deuterium exchange, and the change amount with occurrence of deuterium substitution was calculated in terms of each deuteration period.

As a result of the H/D exchange mass spectrometry, it was demonstrated the peptides of the amino acid numbers 27 to 37, 29 to 37, 29 to 38, 43 to 60, 82 to 100, 98 to 107, 111 to 124, 116 to 125, 116 to 129, 119 to 129, 189 to 198 and 190 to 198 of Accession No. NP_000450.2 have inhibited deuteration in the coexistence of the antibody. The redundant domains of these peptides are arranged, further, the information of the peptides having not inhibited deuteration was added thereof and taking into consideration that two amino acids on the N-terminal side easily undergo reverse change (Proteins, 1993, Vol. 17, 75-86), five regions having inhibited deuterium substitution, that is, amino acid numbers 29 to 38, 84 to 102, 113 to 120, 126 to 129, and 191 to 198 of Accession No. NP_000450.2 as the epitope candidate sites were found. Further, as a result of the H/D exchange mass spectrometry, it was found that in the case where TIE-1-Igγ1-LALA interacts with a region consisting of these five amino acid segments or where a change in the steric structure or an allosteric effect by the antibody binding occurs, these residues are protected from hydrogen/deuterium exchange.

Example 17: Evaluation of Epitope of TIE-1-Igγ1-LALA: Surface Plasmon Resonance Analysis and ELISA An epitope candidate for human Tie2 of TIE-1-Igγ1-LALA was identified from H/D exchange mass spectrometry of Example 16. In order to predict the epitope portion in detail, amino acid mutants of the human Tie2 (1-452)-Fc chimeric protein were prepared, and the binding activity was evaluated using surface plasmon resonance analysis (SPR analysis) and ELISA.

Based on the result of the H/D exchange mass spectrometry and the report of a region in which Ang-1 and Ang-2 bind to Tie2 (Nat. Struct. Mol. Biol., 2006, Vol. 13, pp.

524-532. Proc. Natl. Acad. Sci. USA, 2013, Vol. 110, 7205-7210), 23 amino acid mutant proteins in which one to four amino acids were substituted with alanine (in one case, glutamic acid) of the human Tie2 (1-452) in the human Tie2 (1-452)-Fc chimeric protein as amino acid mutant proteins of the human Tie2 (1-452) were prepared (Table 6). Various mutants were prepared by the same preparation method for the human Tie2 (1-452)-Fc chimeric protein prepared in Example 16.

TABLE 6

Mutant human Tie2 (1-452)-Fc chimeric proteins

| Name of Mutant | Amino acid variation site |
|---|---|
| Human Tie2 (1-452)r1-Fc | R167A, H168A, E169A |
| Human Tie2 (1-452)r2-Fc | D172A, I173A |
| Human Tie2 (1-452)r3-Fc | R167A |
| Human Tie2 (1-452)r4-Fc | H168A |
| Human Tie2 (1-452)r5-Fc | E169A |
| Human Tie2 (1-452)r6-Fc | D172A |
| Human Tie2 (1-452)r7-Fc | I173A |
| Human Tie2 (1-452)g1-Fc | I194A, N197A, L198A |
| Human Tie2 (1-452)g2-Fc | R192A |
| Human Tie2 (1-452)g3-Fc | I194A |
| Human Tie2 (1-452)g4-Fc | G195E |
| Human Tie2 (1-452)g5-Fc | N197A |
| Human Tie2 (1-452)g6-Fc | L198A |
| Human Tie2 (1-452)m1-Fc | W82A, K84A |
| Human Tie2 (1-452)m3-Fc | S94A, K95A |
| Human Tie2 (1-452)y1-Fc | D37A |
| Human Tie2 (1-452)c1-Fc | R50A, H52A, E53A, P54A |
| Human Tie2 (1-452)A1-Fc | E151A |
| Human Tie2 (1-452)A2-Fc | V154A |
| Human Tie2 (1-452)A3-Fc | Y156A |
| Human Tie2 (1-452)A4-Fc | F161A |
| Human Tie2 (1-452)A5-Fc | S164A |
| Human Tie2 (1-452)A6-Fc | P166A |

SPR analysis was carried out in order to evaluate the binding activity of the human Tie2 (1-452)-Fc chimera protein and 23 mutant proteins thereof to the fully human 2-16A2-Fab.

Figure 6A:
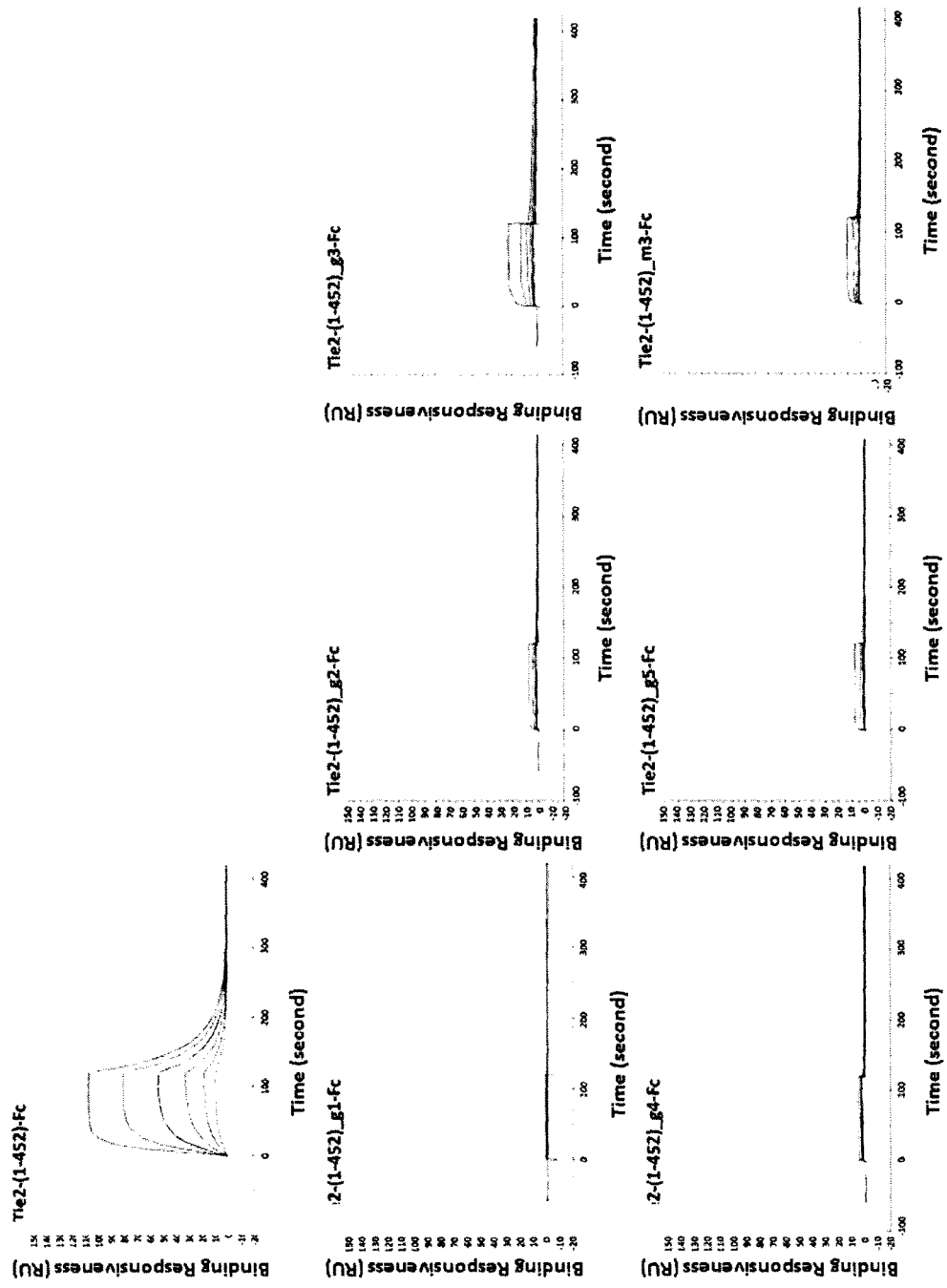
FIGS. 6A and 6B show a representative example of the results of a surface plasmon resonance phenomenon as epitope analysis of TIE-1-Igγ1-LALA. The vertical axis indicates a binding responsiveness (Resonance Unit: RU) and the horizontal axis indicates time (seconds).
Figure 6B:
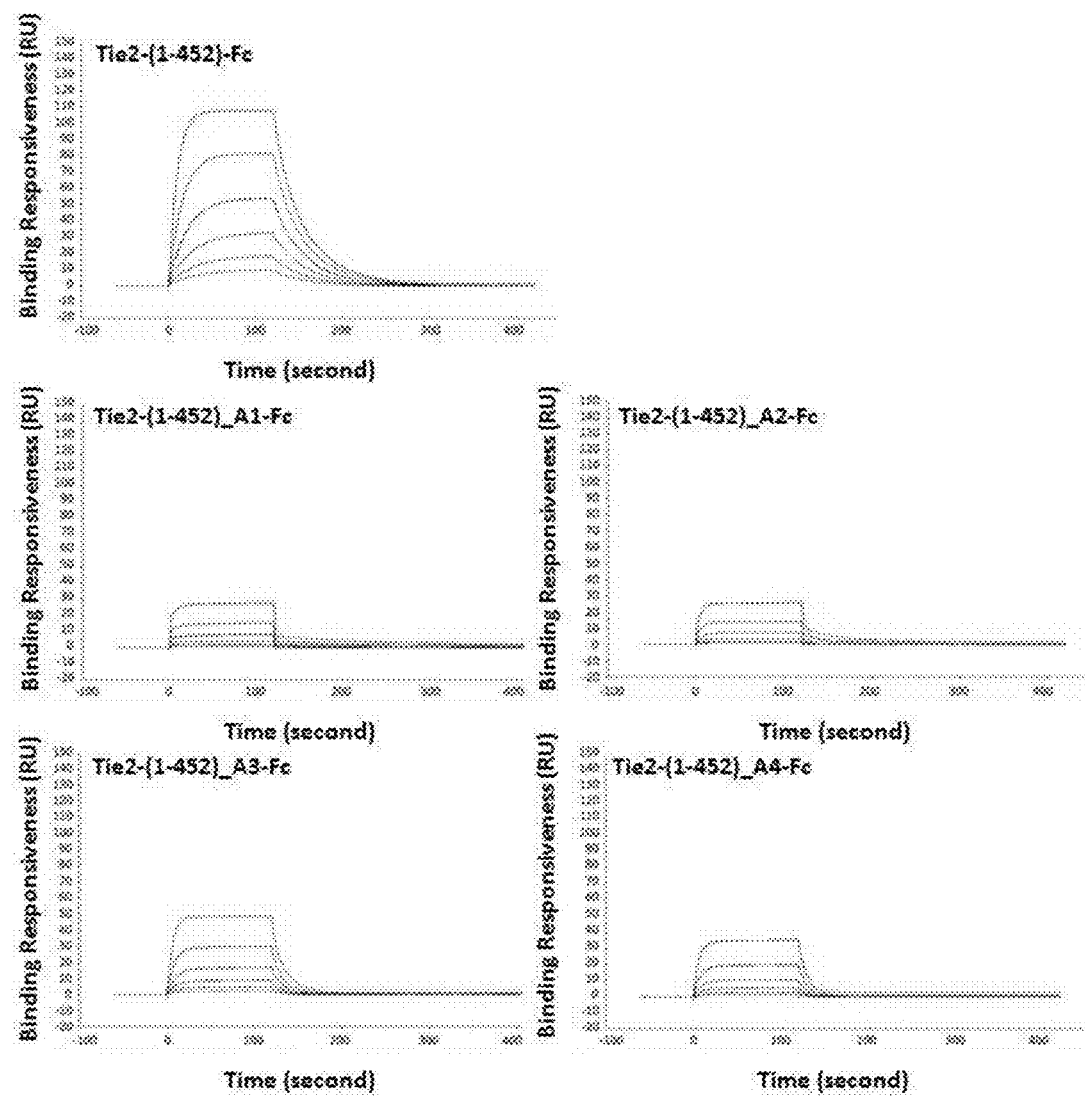

For SPR analysis, Biacore T200 (GE Healthcare) was used. An anti-human IgG (Fc) antibody (Human Antibody Capture Kit, GE Healthcare) was fixed onto a CM5 sensor chip. The human Tie2 (1-452)-Fc chimeric protein and 23 mutant proteins thereof, diluted with HBS-EP (GE Healthcare) at 5 µg/mL, were each allowed for immobilization, and the capture-amount was measured. Thereafter, the fully human 2-16A2-Fab diluted with HBS-EP to 50 nM, the binding amount thereof to the human Tie2 (1-452)-Fc chimeric protein and 23 mutant proteins thereof were measured. Further, by dividing the binding amount with the capture-amount, the binding amount of the antibody in the unit immobilized antigen (hereinafter referred to as a binding ratio) was calculated. The arithmetic mean of three experiments and the relative value of the binding ratio of each mutant proteins when the binding ratio of the human Tie2 (1-452)-Fc chimeric protein was taken as 100% are shown in Table 7. Further, the representative measurement data is shown in FIGS. 6A and 6B. The method for relative comparison of the binding amounts in Biacore is described in, for example, Analytical Biochemistry, 2003, Vol. 312, pp. 113-124.

As a result, it was found that the binding of the fully human 2-16A2-Fab was decreased in the human Tie2 (1-452)g1-Fc, the human Tie2 (1-452)g2-Fc, the human Tie2 (1-452)g3-Fc, the human Tie2 (1-452)g4-Fc, the human Tie2 (1-452)g5-Fc, the human Tie2 (1-452)m3-Fc, the human Tie2 (1-452)A1-Fc, the human Tie2 (1-452)A2-Fc, the human Tie2 (1-452)A3-Fc and the human Tie2 (1-452)A4-Fc, compared with the human Tie2 (1-452)-Fc chimeric protein.

TABLE 7

Results of SPR Analysis

| | Binding ratio | Relative value (%) |
|---|---|---|
| Human Tie2 (1-452)-Fc chimeric protein | 0.29 | 100 |
| Human Tie2 (1-452)r1-Fc | 0.29 | 102 |
| Human Tie2 (1-452)r2-Fc | 0.28 | 98 |
| Human Tie2 (1-452)r3-Fc | 0.34 | 119 |
| Human Tie2 (1-452)r4-Fc | 0.33 | 113 |
| Human Tie2 (1-452)r5-Fc | 0.29 | 99 |
| Human Tie2 (1-452)r6-Fc | 0.29 | 100 |
| Human Tie2 (1-452)r7-Fc | 0.30 | 106 |
| Human Tie2 (1-452)g1-Fc | 0.00 | 0 |
| Human Tie2 (1-452)g2-Fc | 0.03 | 9 |
| Human Tie2 (1-452)g3-Fc | 0.06 | 23 |
| Human Tie2 (1-452)g4-Fc | 0.02 | 7 |
| Human Tie2 (1-452)g5-Fc | 0.03 | 9 |
| Human Tie2 (1-452)g6-Fc | 0.38 | 131 |
| Human Tie2 (1-452)m1-Fc | 0.31 | 107 |
| Human Tie2 (1-452)m3-Fc | 0.04 | 12 |
| Human Tie2 (1-452)y1-Fc | 0.25 | 87 |
| Human Tie2 (1-452)c1-Fc | 0.54 | 189 |
| Human Tie2 (1-452)A1-Fc | 0.10 | 34 |
| Human Tie2 (1-452)A2-Fc | 0.08 | 29 |
| Human Tie2 (1-452)A3-Fc | 0.17 | 59 |
| Human Tie2 (1-452)A4-Fc | 0.13 | 44 |
| Human Tie2 (1-452)A5-Fc | 0.39 | 135 |
| Human Tie2 (1-452)A6-Fc | 0.31 | 109 |

ELSA was carried out by the method as in Example 12 in order to evaluate the binding activity of TIE-1-Igγ1-LALA to the human Tie2 (1-452)-Fc chimeric protein and 23 mutant proteins thereof.

Figure 7:
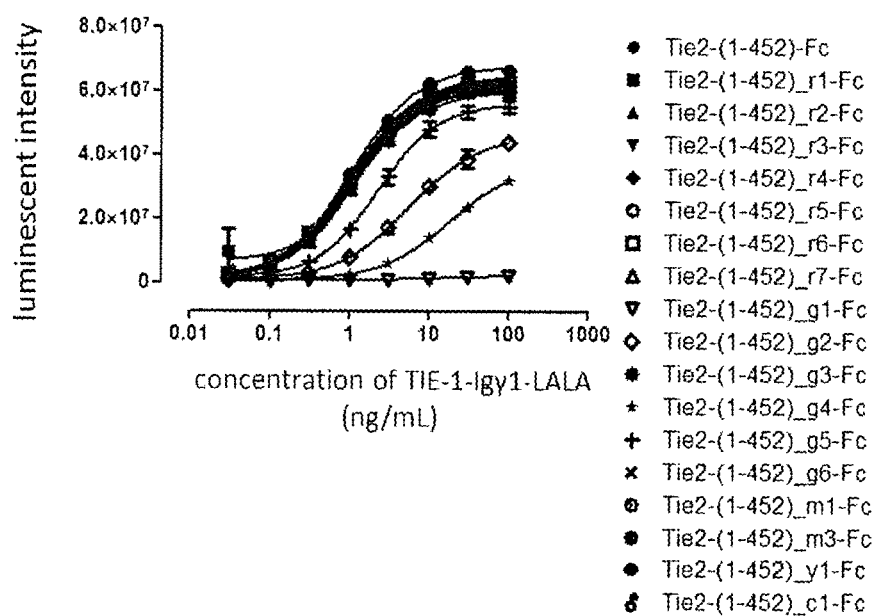
FIG. 7 shows the results of ELISA as epitope analysis of TIE-1-Igγ1-LALA. The vertical axis indicates a luminescent intensity and the horizontal axis indicates a concentration of TIE-1-Igγ1-LALA (ng/mL).
Figure 7:
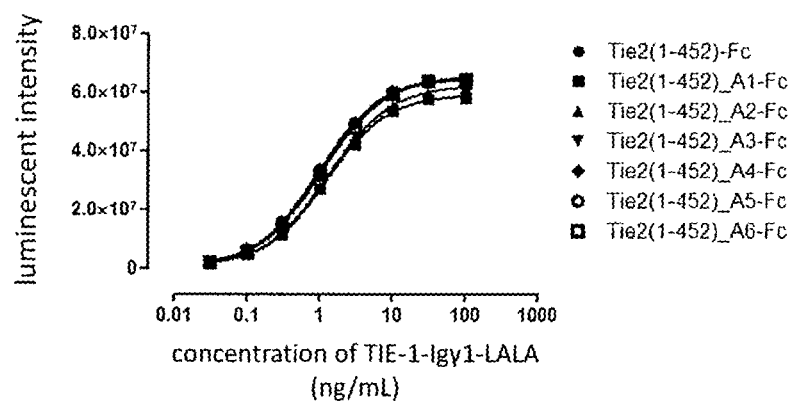

The human Tie2 (1-452)-Fc chimeric protein and 23 mutant proteins thereof were diluted with PBS to 1 µg/mL, added to a white Maxisorp 384-well plate in the amount of 20 µL per well, and incubated at 4° C. overnight to perform immobilization. The next day, the immobilized solution was removed, and the plate was washed with a TBS-T solution, and incubated for 60 minutes by the addition of 50 µL of a Blocker™ Casein in TBS (Thermo Fisher Scientific Inc., 37532) to perform blocking. The resultant was washed with a TBS-T solution, and TIE-1-Igγ1-LALA, diluted with 0.05% Tween 20 (Nacalai Tesque Inc., 28353-85)-containing Blocker™ Casein in TBS from 0.03 ng/mL to 100 ng/mL through eight steps, was added thereto in the amount of 20 µL per well. The resultant was incubated at room temperature for 90 minutes and then washed with a TBS-T solution three times, and 20 µL of a biotin-labeled anti-human kappa light chain antibody, which had been diluted to 0.1 µg/mL with 0.05% Tween 20-containing Blocker™ Casein in TBS, was added thereto. The resultant was incubated at room temperature for 60 minutes and then washed with a TBS-T solution three times, and 20 µL of alkaline phosphatase-labeled streptavidin, which had been diluted to 0.1 µg/mL with 0.05% Tween 20-containing Blocker™ Casein in TBS, was added thereto. The resultant was incubated at room temperature for 60 minutes and then washed with a TBS-T solution three times, and 50 µL of Chemiluminescent Ultra Sensitive AP Microwell and/or Membrane Substrate (450 nm), which had been 5-fold diluted with 1 mM MgCl$_2$-containing 20 mM TBS (pH 9.8) as a substrate, was added thereto. The resultant was incubated at room temperature under light-shielding for 40 minutes, and then luminescent intensity thereof was measured with an EnVision™ multi-label counter. The $EC_{50}$ value of TIE-1-Igγ1-LALA with respect to the human Tie2 (1-452)-Fc chimeric protein and 23 mutant proteins thereof were calculated. The relative value of luminescent intensity of 100 ng/mL TIE-1-Igγ1-LALA as maximum concentration point with respect to human Tie2 (1-452)-Fc chimeric protein and 23 mutant proteins thereof when the convergence value of the sigmoid curve of TIE-1-Igγ1-LALA binding to the human Tie2 (1-452)-Fc chimeric protein which was taken as 100% was calculated (Table 8 and Table 9). Further, the $EC_{50}$ value and the convergence value were calculated by Sigmoid-Emax model non-linear regression analysis. The results of ELISA are shown in FIG. 7.

As a result, it has been found that compared with the human Tie2 (1-452)-Fc chimeric protein, TIE-1-Igγ1-LALA had a remarkably decreased relative value with respect to Tie2 (1-452)g1-Fc, Tie2 (1-452)g2-Fc and Tie2 (1-452)g4-Fc, which are mutant proteins. Further, it has been found that compared with the human Tie2 (1-452)-Fc chimeric protein, TIE-1-Igγ1-LALA had a decreased relative value and an increased $EC_{50}$ value with respect to Tie2 (1-452)g5-Fc, which is a mutant protein. From the result, it was found that TIE-1-Igγ1-LALA had a decreased binding activity to Tie2 (1-452)g1-Fc, Tie2 (1-452)g2-Fc, Tie2 (1-452)g4-Fc, and Tie2 (1-452)g5-Fc, unlike the human Tie2 (1-452)-Fc chimeric protein. Since TIE-1-Igγ1-LALA had a decreased relative value and similar $EC_{50}$ value with respect to Tie2 (1-452)A1-Fc, it was determined that TIE-1-Igγ1-LALA had no change in the binding activity to Tie2 (1-452)A1-Fc.

TABLE 8

Results of ELISA

| | Relative value (%) of luminescent intensity | $EC_{50}$ value (ng/mL) |
|---|---|---|
| Human Tie2 (1-452)-Fc chimeric protein | 97 | 1.1 |
| Human Tie2 (1-452)r1-Fc | 97 | 1.1 |
| Human Tie2 (1-452)r2-Fc | 96 | 0.9 |
| Human Tie2 (1-452)r3-Fc | 102 | 1.0 |
| Human Tie2 (1-452)r4-Fc | 101 | 1.0 |
| Human Tie2 (1-452)r5-Fc | 102 | 1.0 |
| Human Tie2 (1-452)r6-Fc | 100 | 1.0 |
| Human Tie2 (1-452)r7-Fc | 100 | 1.1 |
| Human Tie2 (1-452)g1-Fc | 3 | 12.3 |
| Human Tie2 (1-452)g2-Fc | 72 | 5.5 |
| Human Tie2 (1-452)g3-Fc | 96 | 1.1 |
| Human Tie2 (1-452)g4-Fc | 53 | 18 |
| Human Tie2 (1-452)g5-Fc | 91 | 2.2 |
| Human Tie2 (1-452)g6-Fc | 105 | 1.3 |
| Human Tie2 (1-452)m1-Fc | 104 | 1.0 |
| Human Tie2 (1-452)m3-Fc | 103 | 1.0 |
| Human Tie2 (1-452)y1-Fc | 109 | 1.0 |
| Human Tie2 (1-452)c1-Fc | 104 | 1.0 |

TABLE 9

Results of ELISA

| | Relative value (%) of luminescent intensity | $EC_{50}$ value (ng/mL) |
|---|---|---|
| Human Tie2 (1-452)-Fc chimeric protein | 98 | 1.0 |
| Human Tie2 (1-452)A1-Fc | 90 | 1.3 |
| Human Tie2 (1-452)A2-Fc | 95 | 1.3 |
| Human Tie2 (1-452)A3-Fc | 98 | 1.0 |
| Human Tie2 (1-452)A4-Fc | 100 | 1.0 |
| Human Tie2 (1-452)A5-Fc | 98 | 0.9 |
| Human Tie2 (1-452)A6-Fc | 99 | 1.1 |

From the results of the two independent experiments, the ELISA and the SPR analysis, Tie2 (1-452)g1-Fc, Tie2 (1-452)g2-Fc, Tie2 (1-452)g4-Fc, and Tie2 (1-452)g5-Fc were identified as the mutant proteins to which the binding activity of TIE-1-Igγ1-LALA or the fully human 2-16A2-Fab was decreased in both experiments. It was found that the amino acids numbers 192, 194, 195, 197 and 198 in four mutant proteins are very important epitope candidates for TIE-1-Igγ1-LALA to bind to human Tie2. Herein, the binding activity of Tie2 (1-452)g1-Fc, which has the amino acid variations of I194A, N197A and L198A, decreased in ELISA assay, while the binding activity of Tie2 (1-452)g3-Fc which has the amino acid variation of I194A to TIE-1-Igγ1-LALA did not altered in ELISA assay. The binding activity of Tie2 (1-452)g6-Fc which has the amino acid variation of L198A altered neither in ELISA assay nor in SPR analysis. These results indicated that the mutation of amino acid number 197 in Tie2 (1-452)g1-Fc was the most critical amino acid as epitope. Finally, it was found that TIE-1-Igγ1-LALA binds to amino acid numbers 192, 195 and 197 of Accession No. NP_000450.2 as the epitopes.

INDUSTRIAL APPLICABILITY

The anti-human Tie2 antibody of the present invention is useful for preventing or treating various blood vessel-related diseases. Further, the polynucleotide, the expression vectors, the transformed host cell, and the methods for producing the antibody of the present invention are useful for producing the anti-human Tie2 antibody.

Sequence List Free Text

In the number heading <223> of the sequence list below, description of "Artificial Sequence" is made. Specifically, the base sequence shown by SEQ ID NO: 1 in the sequence list is the base sequence of the heavy chain of TIE-1-Igγ1-LALA and the amino acid sequence shown by SEQ ID NO: 2 is the amino acid sequence of the heavy chain encoded by SEQ ID NO: 1. The base sequence shown by SEQ ID NO: 3 in the sequence list is the base sequence of the light chain of TIE-1-Igγ1-LALA, TIE-1-Igγ1-I253A, TIE-1-Igγ1-WT, TIE-1-Igγ4-PE, and fully human 2-16A2, and the amino acid sequence shown by SEQ ID NO: 4 is the amino acid sequence of the light chain encoded by SEQ ID NO: 3. The base sequence shown by SEQ ID NO: 5 in the sequence list is the base sequence of the heavy chain of TIE-1-Igγ1-I253A and the amino acid sequence shown by SEQ ID NO: 6 is the amino acid sequence of the heavy chain encoded by SEQ ID NO: 5. The base sequence shown by SEQ ID NO: 7 in the sequence list is the base sequence of the heavy chain of TIE-1-Igγ1-WT, and the amino acid sequence shown by SEQ ID NO: 8 is the amino acid sequence of the heavy chain encoded by SEQ ID NO: 7. The base sequence shown by SEQ ID NO: 9 in the sequence list is the base sequence of the heavy chain of TIE-1-Igγ4-PE, and the amino acid sequence shown by SEQ ID NO: 10 is the amino acid sequence of the heavy chain encoded by SEQ ID NO: 9. The base sequence shown by SEQ ID NO: 11 in the sequence list is the base sequence of the heavy chain of the fully human 2-16A2, and the amino acid sequence shown by SEQ ID NO: 12 is the amino acid sequence of the heavy chain encoded by SEQ ID NO: 11. The amino acid sequences shown by SEQ ID NOS: 13 to 20 in the sequence list are the amino acid sequences of the linker. The amino acid sequence shown by SEQ ID NO: 22 in the sequence list is a thrombin recognition site.

The invention claimed is:

1. A polynucleotide selected from the group consisting of (a) and (b):
   (a) a polynucleotide comprising a base sequence encoding a heavy chain variable region consisting of the amino acid sequence of the amino acid numbers 1 to 122 of SEQ ID NO: 2; and
   (b) a polynucleotide comprising a base sequence encoding a light chain variable region consisting of the amino acid sequence of the amino acid numbers 1 to 113 of SEQ ID NO: 4.

2. A polynucleotide selected from the group consisting of (a) and (b):
   (a) a polynucleotide comprising a base sequence encoding a heavy chain consisting of the amino acid sequence shown by SEQ ID NO: 2; and
   (b) a polynucleotide comprising a base sequence encoding a light chain consisting of the amino acid sequence shown by SEQ ID NO: 4.

3. An expression vector comprising:
   (i) a polynucleotide comprising a base sequence encoding a heavy chain variable region consisting of the amino acid sequence of the amino acid numbers 1 to 122 of SEQ ID NO: 2 and/or (ii) a polynucleotide comprising a base sequence encoding a light chain variable region consisting of the amino acid sequence of the amino acid numbers 1 to 113 of SEQ ID NO: 4.

4. An expression vector comprising;
   (i) a polynucleotide comprising a base sequence encoding a heavy chain consisting of the amino acid sequence of the amino acid numbers shown by SEQ ID NO: 2 and/or (ii) a polynucleotide comprising a base sequence encoding a light chain consisting of the amino acid sequence shown by SEQ ID NO: 4.

5. A host cell selected from the group consisting of (a) to (d) below:
   (a) a host cell transformed with an expression vector comprising a polynucleotide comprising a base sequence encoding a heavy chain variable region consisting of the amino acid sequence of the amino acid numbers 1 to 122 of SEQ ID NO: 2 and a polynucleotide comprising a base sequence encoding a light chain variable region consisting of the amino acid sequence of the amino acid numbers 1 to 113 of SEQ ID NO: 4;
   (b) a host cell transformed with an expression vector comprising a polynucleotide comprising a base sequence encoding a heavy chain variable region consisting of the amino acid sequence of the amino acid numbers 1 to 122 of SEQ ID NO: 2 and an expression vector comprising a polynucleotide comprising a base sequence encoding a light chain variable region consisting of the amino acid sequence of the amino acid numbers 1 to 113 of SEQ ID NO: 4;
   (c) a host cell transformed with an expression vector comprising a polynucleotide comprising a base sequence encoding a heavy chain variable region consisting of the amino acid sequence of the amino acid numbers 1 to 122 of SEQ ID NO: 2; and
   (d) a host cell transformed with an expression vector comprising a polynucleotide comprising a base sequence encoding a light chain variable region consisting of the amino acid sequence of the amino acid numbers 1 to 113 of SEQ ID NO: 4.

6. A host cell selected from the group consisting of (a) to (d) below:
   (a) a host cell transformed with an expression vector comprising a polynucleotide comprising a base sequence encoding a heavy chain consisting of the amino acid sequence shown by SEQ ID NO: 2 and a polynucleotide comprising a base sequence encoding a light chain consisting of the amino acid sequence shown by SEQ ID NO: 4;
   (b) a host cell transformed with an expression vector comprising a polynucleotide comprising a base sequence encoding a heavy chain consisting of the amino acid sequence shown by SEQ ID NO: 2 and an expression vector comprising a polynucleotide comprising a base sequence encoding a light chain consisting of the amino acid sequence shown by SEQ ID NO: 4;
   (c) a host cell transformed with an expression vector comprising a polynucleotide comprising a base sequence encoding a heavy chain consisting of the amino acid sequence shown by SEQ ID NO: 2; and
   (d) a host cell transformed with an expression vector comprising a polynucleotide comprising a base sequence encoding a light chain consisting of the amino acid sequence shown by SEQ ID NO: 4.

7. A method for producing an anti-human Tie2 antibody or an antigen-binding fragment thereof, comprising culturing host cell(s) selected from the group consisting of (a) to (c) below to express a tetravalent anti-human Tie2 antibody or an antigen-binding fragment thereof:
   (a) a host cell transformed with an expression vector comprising a polynucleotide comprising a base sequence encoding a heavy chain variable region consisting of the amino acid sequence of the amino acid numbers 1 to 122 of SEQ ID NO: 2 and a polynucleotide comprising a base sequence encoding a light chain variable region consisting of the amino acid sequence of the amino acid numbers 1 to 113 of SEQ ID NO: 4;
   (b) a host cell transformed with an expression vector comprising a polynucleotide comprising a base sequence encoding a heavy chain variable region consisting of the amino acid sequence of the amino acid numbers 1 to 122 of SEQ ID NO: 2 and an expression vector comprising a polynucleotide comprising a base sequence encoding a light chain variable region consisting of the amino acid sequence of the amino acid numbers 1 to 113 of SEQ ID NO: 4; and
   (c) a host cell transformed with an expression vector comprising a polynucleotide comprising a base sequence encoding a heavy chain variable region consisting of the amino acid sequence of the amino acid numbers 1 to 122 of SEQ ID NO: 2 and a host cell transformed with an expression vector comprising a polynucleotide comprising a base sequence encoding a light chain variable region consisting of the amino acid sequence of the amino acid numbers 1 to 113 of SEQ ID NO: 4.

8. A method for producing an anti-human Tie2 antibody, comprising culturing host cell(s) selected from the group consisting of (a) to (c) below to express an anti-human Tie2 antibody:

(a) a host cell transformed with an expression vector comprising a polynucleotide comprising a base sequence encoding a heavy chain consisting of the amino acid sequence shown by SEQ ID NO: 2 and a polynucleotide comprising a base sequence encoding a light chain consisting of the amino acid sequence shown by SEQ ID NO: 4;

(b) a host cell transformed with an expression vector comprising a polynucleotide comprising a base sequence encoding a heavy chain consisting of the amino acid sequence shown by SEQ ID NO: 2 and an expression vector comprising a polynucleotide comprising a base sequence encoding the light chain consisting of the amino acid sequence shown by SEQ ID NO: 4; and (c) a host cell transformed with an expression vector comprising a polynucleotide comprising a base sequence encoding a heavy chain consisting of the amino acid sequence shown by SEQ ID NO: 2 and a host cell transformed with an expression vector comprising a polynucleotide comprising a base sequence encoding a light chain consisting of the amino acid sequence shown by SEQ ID NO: 4.

\* \* \* \* \*